United States Patent [19]

Wakimasu et al.

[11] Patent Number: 5,616,684
[45] Date of Patent: Apr. 1, 1997

[54] CYCLIC PEPTIDES AND USE THEREOF

[75] Inventors: Mitsuhiro Wakimasu; Takashi Kikuchi; Akira Kawada, all of Ibaraki; Hideo Shirafuji, Kyoto, all of Japan

[73] Assignee: Takeda Chemical Industries, Ltd., Osaka, Japan

[21] Appl. No.: 231,449

[22] Filed: Apr. 20, 1994

Related U.S. Application Data

[63] Continuation of Ser. No. 927,205, Aug. 7, 1992, abandoned.

[30] Foreign Application Priority Data

Aug. 13, 1991 [JP] Japan ................................. 3-203032
Nov. 19, 1991 [JP] Japan ................................. 3-303635
Feb. 21, 1992 [JP] Japan ................................. 4-35436
Apr. 30, 1992 [JP] Japan ................................. 4-111792

[51] Int. Cl.$^6$ ................................................ C07K 7/64
[52] U.S. Cl. ........................ 530/317; 530/328; 530/321
[58] Field of Search .................... 514/11, 9, 2; 530/317, 530/328, 321; 930/270

[56] References Cited

U.S. PATENT DOCUMENTS 5,114,918  5/1992  Ishikawa et al. ........................... 514/11
5,260,276  11/1993  Cody et al. ............................... 530/317

FOREIGN PATENT DOCUMENTS

0436189A1  7/1991  European Pat. Off. .
9202546  10/1992  WIPO .

OTHER PUBLICATIONS

Japanese Patent Unexamined Publication No. 3-94692/91.
Japanese Patent Unexamined Publication No. 3-130299/91.
Japanese Patent Unexamined Publication No. 3-17098/91.
Japanese Patent Unexamined Publication No. 3-141295/91.
Editors: Smith et al., "Peptides – Proceedings of the 12th American Peptide Proceedings of the 12th American Peptide Symposium", Jun. 1991, Cambridge, USA' 1992, Escom, Leiden, Holland & Ishikawa, et al., Endothelin antagonistic cyclic pentapeptides with high selectivity for ETa receptor; pp. 812–813.

Masaki Ihara et al.; Biochemical and Biophysical Research Communications, vol. 178, No. 1, 1991 pp. 132–137, Jul. 15, 1991 "An Endothelin Receptor ($ET_A$) Antagonist Isolated From Streptomyces Misakiensis".

K. Ishikawa et al.; Peptides, Chemistry and Biology, pp. 812–813, Jun. 16–21, 1991, "Endothelin antagonistic cyclic pentapeptides with high selectivity for $ET_A$ receptor".

Himata et al, Biochem. and Biophys. Research Commun., vol. 160, pp. 228–234, (Apr. 14, 1989).

Ihara et al, Life Sciences, vol. 50, pp. 247–255, (1991).

Nakajima et al, Biochem. and Biophys. Research Commun., vol. 163(1), (Aug. 30, 1989), pp. 424–429.

Kimura et al, Biochem. and Biophys. Research Commun., vol. 156(3), (Nov. 15, 1988), pp. 1182–1186.

Doherty, Journal of Medicinal Chemistry, vol. 35(9), pp. 1493–1508, (1992).

Saeki et al, Biochemical and Biophysical Res. Comm., vol. 179, No. 1, pp. 286–292, (Aug. 30, 1991).

Primary Examiner—Christina Y. Chan
Assistant Examiner—T. D. Wessendorf
Attorney, Agent, or Firm—David G. Conlin; George W. Neuner; Cara Z. Lowen

[57] ABSTRACT

Cyclic peptides and their salts have antagonistic activity on endothelin receptors and antagonistic activity on NK2 receptors. The peptides have the formula

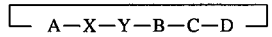

[I]

wherein X and Y each represent α-amino acid residues, A represents a D-acidic-α-amino acid residue, B represents a neutral α-amino acid residue, C represents an L-α-amino acid residue and D represents a D-α-amino acid residue having an aromatic ring group; wherein hydroxy, thiol, amino, imino and carboxyl groups can be substituted or unsubstituted. Pharmaceutical compositions containing such peptides are also described.

1 Claim, No Drawings

SEQUENCE LISTING ( 1 ) GENERAL INFORMATION:

( i i i ) NUMBER OF SEQUENCES: 3

( 2 ) INFORMATION FOR SEQ ID NO:1:

( i ) SEQUENCE CHARACTERISTICS:
( A ) LENGTH: 21 amino acids
( B ) TYPE: amino acid
( D ) TOPOLOGY: linear ( i i ) MOLECULE TYPE: protein ( x i ) SEQUENCE DESCRIPTION: SEQ ID NO:1:

```
     Cys   Ser   Cys   Ser   Ser   Leu   Met   Asp   Lys   Glu   Cys   Val   Tyr   Phe   Cys   His
     1                       5                             10                            15

Leu   Asp   Ile   Ile   Trp
                       20
```

( 2 ) INFORMATION FOR SEQ ID NO:2:

( i ) SEQUENCE CHARACTERISTICS:
        ( A ) LENGTH: 21 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

```
     Cys   Ser   Cys   Ser   Ser   Trp   Leu   Asp   Lys   Glu   Cys   Val   Tyr   Phe   Cys   His
     1                       5                             10                            15

Leu   Asp   Ile   Ile   Trp
                       20
```

( 2 ) INFORMATION FOR SEQ ID NO:3:

( i ) SEQUENCE CHARACTERISTICS:
        ( A ) LENGTH: 21 amino acids
        ( B ) TYPE: amino acid
        ( D ) TOPOLOGY: linear ( i i ) MOLECULE TYPE: protein ( x i ) SEQUENCE DESCRIPTION: SEQ ID NO:3:

```
     Cys   Thr   Cys   Phe   Thr   Tyr   Lys   Asp   Lys   Glu   Cys   Val   Tyr   Tyr   Cys   His
     1                       5                             10                            15

Leu   Asp   Ile   Ile   Trp
                       20
```

CYCLIC PEPTIDES AND USE THEREOF

This is a continuation of application Ser. No. 07/927,205 filed on Aug. 7, 1992, now abandoned.

BACKGROUND OF THE INVENTION

The present invention relates to novel cyclic peptides having antagonistic activity on endothelin receptors and antagonistic activity on NK2 receptors. These cyclic peptides are useful as prophylactic and therapeutic drugs for hypertension, cardiac or cerebral circulatory diseases, renal diseases and asthma, anti-inflammatory drugs, antarthritics and the like. The present invention further relates to the use thereof.

Endothelin (ET) is a vasoconstrictive peptide composed of 21 amino acid residues. Endothelin was isolated from the culture supernatant of the endothelial cells of porcine aortas. Its structure was determined by M. Yanagisawa et al. in 1988 [M. Yanagisawa et al., Nature 332, 411–412 (1988)]. More recently, the research on genes coding for endothelin revealed the presence of peptides similar to endothelin in structure. These peptides are named endothelin-1 (ET-1), endothelin-2 (ET-2) and endothelin-3 (ET-3), respectively. Their structures are as follows:

H—Cys—A1—Cys-A2-A3-A4-A5-
Asp—Lys—Glu—Cys—Val—Tyr-A6-
Cys—His—Leu—Asp—Ile—Ile—Trp—OH

|      |           | A1  | A2  | A3  | A4  | A5  | A6  |
|------|-----------|-----|-----|-----|-----|-----|-----|
| ET-1 | SEQ ID NO 1 | Ser | Ser | Ser | Leu | Met | Phe |
| ET-2 | SEQ ID NO 2 | Ser | Ser | Ser | Trp | Leu | Phe |
| ET-3 | SEQ ID NO 3 | Thr | Phe | Thr | Tyr | Lys | Tyr |

All of the amino acids constituting ET-1, ET-2 and ET-3 take the L-form [Inoue et al., Proc. Natl. Acad. Sci. U.S.A. 86, 2863–2867 (1989)].

The above-mentioned peptides of the endothelin family exist in vivo and have vasopressor activity. For this reason, these peptides are anticipated to be intrinsic factors responsible for the control of circulatory systems, and deduced to be related to hypertension, cardiac or cerebral circulatory diseases such as cardiac infarction and renal diseases such as acute renal insufficiency. In addition, these peptides also have bronchial smooth muscle constrictor activity, and therefore deduced to be related to asthma.

If antagonists to the receptors of the above-mentioned peptides of the endothelin family are obtained, they are not only considered to be useful for elucidation of the functional mechanism of these peptides, but also likely to be used as effective therapeutic drugs for the above-mentioned diseases. We already filed applications for patents with respect to fermentation product-derived cyclic pentapeptides having the antagonistic activity on the endothelin receptors (Japanese Patent Application Nos. 2-413828/1990 and 3-126160/1991). It is therefore an object of the present invention to provide novel peptides which are effective similarly or more than the peptides previously filed.

SUMMARY OF THE INVENTION

The present inventors prepared novel cyclic peptides having the antagonistic activity on the endothelin receptors, and further discovered that a certain group of the peptides thus obtained had the antagonistic activity on the NK2 receptors, completing the present invention by further studies.

Namely, the present invention provides (1) a cyclic hexapeptide represented by formula [I] or a salt thereof:

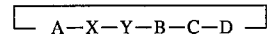

wherein X and Y each represents α-amino acid residues, A represents a D-acidic-α-amino acid residue, B represents a neutral-α-amino acid residue, C represents an L-α-amino acid residue and D represents a D-α-amino acid residue having an aromatic ring group; and (2) a pharmaceutical composition comprising the peptide represented by formula [I] or a pharmaceutically acceptable salt thereof as an active ingredient, in for example, an endothelin receptor antagonist effective amount or an NK2 receptor antagonist effective amount.

DESCRIPTION OF THE PREFERRED EMBODIMENTS

The hexapeptide represented by formula [I] has 6 amide bonds including a bond between A and D, thereby showing that the molecule forms a ring as a whole. In this specification, this hexapeptide is sometimes referred to as cyclo[-A-X-Y-B-C-D-].

In formula [I], an amino acid which forms the α-amino acid residue represented by X or Y may be any amino acid as long as it is an α-amino acid. Examples thereof include alanine, arginine, asparagine, aspartic acid, cysteine, glutamine, glutamic acid, 2-aminomalonic acid, 2-aminoadipic acid, glycine, histidine, isoleucine, leucine, lysine, ornithine, 2,4-diaminobutyric acid, methionine, phenylalanine, proline, 4-hydroxyproline, thioproline, azetidine-2-carboxylic acid, pipecolic acid (piperidine-2-carboxylic acid), indoline-2-carboxylic acid, tetrahydroisoquinoline-3-carboxylic acid, serine, threonine, tryptophan, 5-methyltryptophan, tyrosine, valine, alloisoleucine, norvaline, norleucine, tertiary leucine, γ-methylleucine, phenylglycine, 2-aminobutyric acid, cysteic acid, homocysteic acid, 1-naphthylalanine, 2-naphthylalanine, 2-thienylglycine, 3-thienylglycine, 3-benzothienyl-alanine, 4-biphenylalanine, pentamethylphenylalanine, 1-aminocyclopropane-1-carboxylic acid, 1-aminocyclobutane-1-carboxylic acid, 1-aminocyclopentane-1-carboxylic acid, 1-aminocyclohexane-1-carboxylic acid and 1-aminocycloheptane-1-carboxylic acid. When these α-amino acids have functional groups such as hydroxyl, thiol, amino, imino and carboxyl, these functional groups may be substituted.

The substituted hydroxyl groups include esters such as $C_{1-6}$ fatty acid esters (for example, formates, acetates and propionates), $C_{4-9}$ alicyclic carboxylic acid esters (for example, cyclopentanecarboxylates and cyclohexanecarboxylates), $C_{7-15}$ arylcarboxylic acid esters (for example, benzoates and 4-methylbenzoates), $C_{8-16}$ aralkylcarboxylic acid esters (for example, phenylacetates, 2-phenylpropionates, 3-phenylpropionates and diphenylacetates) and aromatic heterocycle-alkylcarboxylic acid esters (for example, indole-2-ylacetates and indole-3-ylacetates); and ethers such as $C_{1-6}$ alkyl ethers (for example, methyl ethers, ethyl ethers, n-propyl ethers and t-butyl ethers), $C_{3-8}$ cycloalkyl ethers (for example, cyclopentyl ethers and cyclohexyl ethers), $C_{6-12}$ aryl ethers (for example, phenyl ethers and 4-methylphenyl ethers) and $C_{7-15}$ aralkyl ethers (for example, benzyl ethers, phenethyl ethers and diphenylmethyl ethers). Examples of the α-amino acids whose hydroxyl groups are substituted include O-acetylserine, O-acetylthreonine, 4-acetoxyproline, O-benzoylserine, O-benzoylthreonine, 4-benzoyloxyproline, O-phenylacetylserine, O-phenylacetylthreonine, 4-phenylacetoxyproline, O-ethylserine, O-ethylthreonine, 4-ethoxyproline, O-cyclohexylserine, O-cyclohexylthreonine, 4-cyclohexyloxyproline, O-phenylserine, O-phenylthreonine, 4-phenoxyproline, O-benzylserine, O-benzylthreonine, 4-benzyloxyproline, O-diphenylmethylserine, O-diphenylmethylthreonine and 4-diphenylmethoxyproline.

The substituted thiol groups include thiol esters such as $C_{1-6}$ fatty acid thiol esters (for example, formic acid thiol esters, acetic acid thiol esters and propionic acid thiol esters), $C_{4-9}$ alicyclic carboxylic acid thiol esters (for example, cyclopentanecarboxylic acid thiol esters and cyclohexanecarboxylic acid thiol esters), $C_{7-15}$ arylcarboxylic acid thiol esters (for example, benzoic acid thiol esters and 4-methylbenzoic acid thiol esters) and $C_{8-16}$ aralkylcarboxylic acid thiol esters (for example, phenylacetic acid thiol ester, 2-phenylpropionic acid thiol esters, 3-phenylpropionic acid thiol esters and diphenylacetic acid thiol esters); and thioether forms such as $C_{1-6}$ alkyl thioethers (for example, methyl thioethers, ethyl thioethers, n-propyl thioethers and t-butyl thioethers), $C_{3-8}$ cycloalkyl thioethers (for example, cyclopentyl thioethers and cyclohexyl thioethers), $C_{6-12}$ aryl thioethers (for example, phenyl thioethers and 4-methylphenyl thioethers) and $C_{7-15}$ aralkyl thioethers (for example, benzyl thioethers, phenethyl thioethers and diphenylmethyl thioethers). Examples of the α-amino acids whose thiol groups are substituted include S-acetyl-cysteine, S-benzoylcysteine, S-phenylacetylcysteine, S-ethylcysteine, S-cyclohexylcysteine, S-phenylcysteine and S-benzylcysteine.

The substituted amino groups (or imino groups) include substituted amino or imino groups such as $C_{1-6}$ alkylamino (or imino) [for example, N-methylamino (or imino), N-ethylamino (or imino) and N-t-butylamino (or imino)], $C_{3-8}$ cycloalkyl-amino (or imino) [for example, N-cyclopentylamino (or imino) and N-cyclohexylamino (or imino)], $C_{6-12}$ arylamino (or imino) [for example, N-phenylamino (or imino) and N-{4-methylphenyl}amino (or imino)], $C_{7-15}$ aralkylamino (or imino) [for example, N-benzylamino (or imino), N-phenethyl-amino (or imino), N-{2-chlorobenzyl}amino (or imino), N-{3-chlorobenzyl}amino (or imino), N-{4-chlorobenzyl}amino (or imino), N-{2-methylbenzyl}amino (or imino), N-{3-methylbenzyl}amino (or imino), N-{4-methylbenzyl}amino (or imino), N-{2-methoxybenzyl}amino (or imino), N-{3-methoxy-benzyl}amino (or imino) and N-{4-methexybenzyl}amino (or imino)] and aromatic heterocycle-$C_{1-5}$ alkylamino (or imino) [for example, 2-furylmethylamino (or imino), 3-furyl-methylamino (or imino), 2-thienylmethylamino (or imino), 3-thienylmethylamino (or imino), indole-2-ylmethylamino (or imino) and indole-3-ylmethylamino (or imino)]; and substituted amido (or imido) groups such as $C_{1-6}$ aliphatic acylamido (or imido) [for example, formamido (or imido), acetamido (or imido) and propionamido (or imido)], $C_{4-9}$ alicyclic acylamido (or imido) [for example, cyclopentanecarbonylamido (or imido) and cyclohexanecarbonylamido (or imido)], $C_{7-15}$ arylacylamido (or imido) [for example, benzamido (or imido) and 4-methylbenzamido (or imido)], $C_{8-16}$ aralkylacylamido (or imido) [for example, phenylacetamido (or imido), 2-phenylpropionamido (or imido), 3-phenylpropionamido (or imido), diphenylacetamido (or imido), 1-naphthylacetamido (or imido) and 2-naphthylacetamido (or imido)], aromatic heterocycle-carbonylamido (or imido) [for example, indole-2-ylcarbonylamido (or imido) and indole-3-ylcarbonylamido (or imido)], aromatic heterocycle-alkylcarbonylamido (or imido) [for example, indole-2-ylacetamido (or imido) and indole-3-ylacetamido (or imido)], and sulfonylamido (or imido) [for example, benzenesulfonylamido (or imido), p-toluenesulfonylamido (or imido) and 4-methoxy-2,3,6-trimethylbenzenesulfonylamido (or imido)]. Examples of the α-amino acids whose amino (or imino) groups are substituted include N-methylglycine (sarcosine), N-ethylglycine, N-methylleucine, N-ethylleucine, N-methylphenylalanine, N-ethylphenylalanine, N(α)-methyltryptophan, N(α)-ethyltryptophan, N-cyclopentylglycine, N-cyclohexylglycine, N-phenylglycine, N-phenylleucine, N-benzylglycine, N-benzylleucine, N(π)-benzylhistidine, N(τ)-benzylhistidine, N(π)-phenacylhistidine, N(π)-benzyloxymethylhistidine, $N^g$-benzenesulfonylarginine, $N^g$-p-toluenesulfonylarginine, $N^g$-(4-methoxy-2,3,6-trimethylbenzenesulfonyl)arginine, N(∈)-benzenesulfonyllysine, N(∈)-p-toluenesulfonyllysine, N(∈)-(4-methoxy-2,3,6-trimethylbenzenesulfonyl)lysine, $N^{in}$-methyltryptophan, $N^{in}$-ethyltryptophan, $N^{in}$-formyltryptophan, $N^{in}$-acetyltryptophan, N(∈)-benzyllysine, N(∈)-(2-furylmethyl)lysine, N(∈)-(2-thienylmethyl)lysine, N(∈)-(indole-3-ylmethyl)lysine, N(∈)-phenylacetyllysine, N(∈)-({2-furyl}acetyl)lysine, N(∈)-({2-thienyl}acetyl)lysine, N(∈)-({indole-3-yl}acetyl)lysine, N(∈)-benzoyllysine, N(∈)-(3-phenylpropionyl)lysine, N(δ)-benzylornithine, N(δ)-(2-furylmethyl)ornithine, N(δ)-(2-thienylmethyl)ornithine, N(δ)-(indole-3-ylmethyl)ornithine, N(δ)-benzoylornithine, N(δ)-phenylacetylornithine, N(δ)-(3-phenylpropionyl)ornithine, N(δ)-({2-methylphenyl}acetyl)ornithine, N(δ)-({3-methylphenyl}acetyl)ornithine, N(δ)-({4-methylphenyl}acetyl)ornithine, N(δ)-({2-chlorophenyl}acetyl)ornithine, N(δ)-({3-chlorophenyl}acetyl)ornithine, N(δ)-({4-chlorophenyl}acetyl)ornithine, N(δ)-({2-methoxyphenyl}acetyl)ornithine, N(δ)-({3-methoxyphenyl}acetyl)ornithine, N(δ)-({4-methoxyphenyl}acetyl)ornithine, N(δ)-(4-biphenylacetyl)ornithine, N(γ)-benzyl-2,4-diaminobutyric acid, N(γ)-(2-furylmethyl)-2,4-diaminobutyric acid, N(γ)-(2-thienylmethyl)-2,4-diaminobutyric acid, N(γ)-(indole-3-ylmethyl)-2,4-diaminobutyric acid, N(γ)-benzoyl-2,4-diaminobutyric acid, N(γ)-phenylacetyl-2,4-diaminobutyric acid, N(γ)-(3-phenylpropionyl)-2,4-diaminobutyric acid, N(γ)-(2-furylacetyl)-2,4-diaminobutyric acid, N(γ)-(2-thienylacetyl)-2,4-diaminobutyric acid and N(γ)-({inole-3-yl}acetyl)-2,4-diaminobutyric acid.

The substituted carboxyl groups include amido groups such as carboxylic acid amido (—$CONH_2$), N—$C_{1-6}$ alkylamido (for example, N-methylamido, N-ethylamido, N-{n-propyl}amido and N-t-butylamido), N—$C_{3-8}$ cycloalkylamido (for example, N-cyclopentylamido and N-cyclohexylamido), N—$C_{6-12}$ arylamido (for example, N-phenylamido and N-{4-methylphenyl}amido), N—$C_{7-15}$ aralkylamido (for example, N-benzylamido, N-phenethylamido, N-{1,2-diphenylethyl}amido), N-{aromatic heterocycle-$C_{1-6}$ alkyl}amido (for example, N-[2-{indole-2-yl}ethyl]amido and N-[2-{indole-3-yl}ethyl]amido), piperidineamido, piperazineamido, $N^4$—$C_{1-6}$ alkylpiperazineamido (for example, $N^4$-methylpiperazineamido and $N^4$-ethylpiperazineamido), $N^4$—$C_{3-8}$ cycloalkylpiperazineamido (for example, $N^4$-cyclopentylpiperazineamido and $N^4$-cyclohexylpiperazineamido), $N^4$-(5 to 7 membered heterocyclicpiperazineamido (for example $N^4$-pyridylpiperazineamido, $N^4$-furylpiperazineamido, $N^4$-thienylpiperazineamido), $N^4$—$C_{6-12}$ arylpiperazineamido (for example, N⁴-phenylpiperazineamido and N⁴-{4-methylphenyl}piperazineamido), N⁴—C₇₋₁₅ aralkylpiperazineamido (for example, N⁴-benzylpiperazineamido, N⁴-phenetylpiperazineamido, N⁴-{1,2-diphenylethyl}piperazineamido), N⁴-{aromatic heterocycle-C₁₋₆ alkyl}piperazineamido (for example, N⁴-[2-{indole-2-yl}ethyl]piperazineamido and N⁴-[2-{indole-3-yl}ethyl]piperazineamido), N⁴—C₁₋₆ aliphatic acylpiperazineamido (for example, N⁴-acetylpiperazineamido and N⁴-propionylpiperazineamido), N⁴—C₄₋₉ alicyclic acylpiperazineamido (for example, N⁴-cyclopentanecarbonylpiperazineamido and N⁴-cyclohexanecarbonylpiperazineamido), N⁴—C₇₋₁₅ arylacylpiperazineamido (for example, N⁴-benzoylpiperazineamido and N⁴-{4-methylbenzoyl}piperazineamido), N⁴—C₈₋₁₆ aralkylacylpiperazineamido (for example, N⁴-phenylacetylpiperazineamido N⁴-{2-phenylpropion}piperazineamido, N⁴-{3-phenylpropionyl}piperazineamido, N⁴-diphenylacetyl piperazineamido), N⁴-{1-naphthylacetyl}piperazineamido and N⁴-{2-naphthylacetyl}piperazineamido), N⁴-{aromatic heterocycle-carbonyl}piperazineamido (for example, N⁴-{indole-2-ylcarbonyl}piperazineamido and N⁴-{indole-3-ylcarbonyl}piperazineamido), and N⁴-{aromatic heterocyclicalkylcarbonyl}piperazineamido (for example, N⁴-{indole-2-ylacetyl}piperazineamido and N⁴-{indole-3-ylacetyl}piperazineamido); and esters such as C₁₋₆ alkyl esters (for example, methyl esters, ethyl esters and n-propyl esters), C₃₋₈ cycloalkyl esters (for example, cyclopentyl esters and cyclohexyl esters) and C₇₋₁₅ aralkyl esters (for example, benzyl esters, phenetyl esters, 1-phenylethyl esters and diphenylmethyl esters). The above-mentioned amido forms also include amido groups with α-amino acids and amido groups with oligopeptides (for example, dipeptides, tripeptides and tetrapeptides). The α-amino acids whose carboxyl groups are substituted include, for example, N⁴-methylasparagine, N⁴-phenylasparagine, N⁴-benzylasparagine, N⁴-phenethylasparagine, N⁴-(2-{indole-3-yl}ethyl)asparagine, N⁵-methylglutamine, N⁵-phenylglutamine, N⁵-benzylglutamine, N⁵-phenethylglutamine, N⁵-(2-{indole-3-yl}ethyl)glutamine, aspartic acid β-methyl ester, aspartic acid β-cyclopropyl ester, aspartic acid β-benzyl ester, aspartic acid β-phenethyl ester, aspattic acid β-N⁴-phenylpiperazineamide, aspartic acid β-N⁴-(2-methylphenyl)piperazineamide, aspartic acid β-N⁴-(3-methylphenyl)piperazineamide, aspartic acid β-N⁴-(4-methylphenyl)piperazineamide, aspartic acid β-N⁴-(2-methoxyphenyl)piperazineamide, aspartic acid β-N⁴-(3-methoxyphenyl)piperazineamide, aspartic acid β-N⁴-(4-methoxyphenyl)piperazineamide, aspartic acid β-N⁴-(2-chlorophenyl)piperazineamide, aspartic acid β-N⁴-(3-chlorophenyl)piperazineamide, aspartic acid β-N⁴-(4-chlorophenyl)piperazineamide, aspartic acid β-N⁴-(4-nitrophenyl)piperazineamide, aspartic acid β-N⁴-(4-fluorophenyl)piperazineamide, aspartic acid β-N⁴-(3-trifluoromethylphenyl)piperazineamide, aspartic acid β-N⁴-(2,3-dimethylphenyl)piperazineamide, aspartic acid β-N⁴-(2-pyridyl)piperazineamide, aspartic acid β-N⁴-(2-pyrimidyl)piperazineamide, glutamic acid γ-methyl ester, glutamic acid γ-cyclopropyl ester, glutamic acid γ-benzyl ester and glutamic acid γ-phenethyl ester.

The α-amino acid which forms the amino acid residue represented by X or Y in formula [I] may be any of the L-, D- and DL-forms. The L-form is, however, more preferred in each case.

An amino acid which forms the D-acidic-α-amino acid residue represented by A in formula [I] is, for example, an amino acid with an acidic group such as carboxyl, sulfonyl or tetrazolyl as a side chain. Examples of such amino acids include D-glutamic acid, D-aspartic acid, D-cysteic acid, D-homocysteic acid, D-β-(5-tetrazolyl)alanine and D-2-amino-4-(5-tetrazolyl)butyric acid. In particular, D-glutamic acid, D-aspartic acid and D-cysteic acid are preferred.

An amino acid which forms the neutral-α-amino acid residue represented by B in formula [I] is an α-amino acid. Examples of such α-amino acids include alanine, valine, norvaline, leucine, isoleucine, alloisoleucine, norleucine, tertiary leucine, γ-methylleucine, phenylglycine, phenylalanine, 1-naphthylalanine, 2-naphthylalanine, proline, 4-hydroxyproline, azetidine-2-carboxylic acid, pipecolic acid (piperidine-2-carboxylic acid), 2-thienylalanine, 2-thienylglycine, 3-thienylglycine, 1-aminocyclopropane-1-carboxylic acid, 1-aminocyclobutane-1-carboxylic acid, 1-aminocyclopentane-1-carboxylic acid, 1-aminocyclohexane-1-carboxylic acid, 1-aminocycloheptane-1-carboxylic acid, 2-cyclopentylglycine and 2-cyclohexylglycine. When the above-mentioned neutral-α-amino acid exists in the L- and D-forms, the D-form is preferred. D-Leucine, D-alloisoleucine, D-tertiary leucine, D-γ-methylleucine, D-phenylglycine, D-2-thienylalanine, D-2-thienylglycine, D-3-thienylglycine and D-2-cyclopentylglycine are preferred among others. α-Imino groups of these neutral-α-amino acids may be substituted by C₁₋₆ alkyl groups (for example, methyl, ethyl, n-propyl and t-butyl). Examples of such α-amino acids include N-methylleucine, N-methylalloisoleucine, N-methyl tertiary leucine, N-methyl γ-methylleucine and N-methylphenyl-glycine. Also for these α-amino acids, the D-form is preferred.

As an amino acid which forms the L-α-amino acid residue represented by C in formula [I], used is an L-α-amino acid usually known in the art. Examples of such L-α-amino acids include glycine, L-alanine, L-valine, L-norvaline, L-leucine, L-isoleucine, L-tertiary leucine, L-norleucine, L-methionine, L-2-aminobutyric acid, L-serine, L-threonine, L-phenylalanine, L-aspartic acid, L-glutamic acid, L-asparagine, L-glutamine, L-lysine, L-tryptophan, L-arginine, L-tyrosine and L-proline. In particular, L-leucine, L-norleucine and L-tryptophan are preferred. α-Imino groups of these L-α-amino acids may be substituted by C₁₋₆ alkyl groups (for example, methyl, ethyl, n-propyl and t-butyl). Examples of such L-α-amino acids include L-N-methylleucine, L-N-methylnorleucine and L-N(α)-methyltryptophan.

As an amino acid which forms the D-α-amino acid residue with the aromatic ring group represented by D in formula [I], used is a D-α-amino acid having an aromatic ring group as a side chain. Preferred examples thereof include D-tryptophan, D-5-methyltryptophan, D-phenylalanine, D-tyrosine, D-1-naphthylalanine, D-2-naphthylalanine, D-3-benzothienylalanine, D-4-biphenylalanine and D-pentamethylphenylalanine. D-Tryptophan and D-5-methyltryptophan are preferred, and particularly, D-tryptophan is more preferred. The α-imino groups of the D-α-amino acids having the aromatic rings may be substituted by C₁₋₆ alkyl groups (for example, methyl, ethyl, n-propyl and t-butyl). Further, the imino group of the indole ring of D-tryptophan may be substituted by a hydrocarbon group such as a C₁₋₆ alkyl group (for example, methyl, ethyl, n-propyl or t-butyl), a C₃₋₈ cycloalkyl group (for example, cyclopentyl or cyclohexyl), a C₆₋₁₂ aryl group (for example, phenyl, or 4-methylphenyl) or C₇₋₁₅ aralkyl (for example, benzyl or phenethyl), or an acyl group such as a C₁₋₆ aliphatic acyl group (for example, formyl, acetyl or propionyl), a C₄₋₉ alicyclic acyl group (for example, cyclopentanecarbonyl or cyclohexanecarbonyl), a C₇₋₁₅ arylacyl group (for example, benzoyl or 4-methylbenzoyl), a C₈₋₁₆ aralkylacyl group (for example, phenylacetyl, 2-phenylpropionyl, 3-phenylpropionyl or diphenylacetyl) or a $C_{1-6}$ alkoxycarbonyl group (for example, methoxycarbonyl or ethoxycarbonyl). Examples of such α-amino acids include D-N(α)-methyltryptophan, D-N-methylphenylalanine, D-N-methyltyrosine, D-$N^{in}$-methyltryptophan, D-$N^{in}$-ethyltryptophan, D-$N^{in}$-formyltryptophan and D-$N^{in}$-acetyltryptophan. D-$N^{in}$-methyltryptophan, D-$N^{in}$-formyltryptophan and D-$N^{in}$-acetyltryptophan are preferred among others.

In the hexapeptide represented by formula [I], the preferable embodiments of each parameter are as follows:

X has L-configuration.

Y has L-configuration.

A is selected from the group consisting of D-glutamic acid, D-aspartic acid, D-cysteic acid and D-β-(5-tetrazolyl)alanine residue.

B has D-configuration.

B is selected from the group consisting of 1-aminocyclopropane-1-carboxylic acid, 1-aminocyclobutane-1-carboxylic acid, 1-aminocyclopentane-1-carboxylic acid, 1-aminocyclohexane-1-carboxylic acid and 1-aminocycloheptane-1-carboxylic acid residue.

B is selected from the group consisting of D-leucine, D-alloisoleucine, D-tertiaryleucine, D-gammamethylleucine, D-phenylglycine, D-2-thienylglycine, D-3-thienylglycine, D-cyclopentylglycine, D-phenylalanine, D-2-thienylalanine, D-valine, D-2-furylhglycine and D-3-furylglycine residue.

C is selected from the group consisting of L-leucine, L-isoleucine, L-valine, L-norleucine and L-α-amino acid residue having aromatic moiety.

C is selected from the group consisting of L-leucine, L-phenylalanine and L-tryptophan.

D is D-tryptophan, or a derivative thereof, D-1-naphthylalanine, D-2-naphthylalanine, D-benzothienylalanine, D-4-bisphenylalanine and D-pentamethylphenylalanine residue.

The derivative of tryptophan is selected from the group consisting of D-$N^{in}$-methyltryptophan, D-$N^{in}$-formyltryptophan and D-$N^{in}$-acetyltryptophan residue.

Preferable combinations of each parameter include such as those in which A is D-aspartic acid residue; X is tryptophan, L-(β-4-phenylpiperazine amide)aspartic acid, L-($N^δ$-phenylacetyl)ornithine, L-($N^4$-[indol-3-yl]ethyl)ornithine, L-(4-benzyloxy)proline, L-($N^5$-benzyl)glutamine or L-($N^δ$-[indol-3-yl]acetyl)asparagine residue; Y is L-leucine, L-aspartic acid, L-O-benzylserine, tryptophan, serine or proline residue; B is D-leucine, D-2-thienylglycine or D-3-thienylglycine residue; C is L-leucine residue; and D is D-tryptophan residue.

All the cyclic peptides represented by formula [I] of the present invention (hereinafter referred to as the cyclic peptides [I]) have the antagonistic activity on endothelin receptors. In addition, the peptides having amino acid residues such as aspartic acid and tryptophan as X and amino acid residues such as leucine, tryptophan and O-benzylserine as Y further also have the antagonistic activity on NK2 receptors.

The salts of the cyclic peptides [I] include metal salts (for example, sodium salts, potassium salts, calcium salts and magnesium salts), salts of bases or basic compounds (for example, ammonium salts and arginine salts), addition salts of inorganic acids (for example, hydrochlorides, sulfates and phosphates), and salts of organic acids (for example, acetates, propionates, citrates, tartaratates, malates and oxalates).

As described in the working examples of the specification, the cyclic peptides [I] of the present invention can be produced by methods for peptide synthesis known in the art, which may be either solid phase synthesis methods or liquid phase synthesis methods. In some cases, the liquid phase synthesis methods are preferred. Examples of such methods for peptide synthesis include methods described in M. Bodansky and M. A. Ondetti, *Peptide Synthesis.*, Interscience, New York (1966); F. M. Finn and K. Hofmann, *The Proteins*, Vol. 2, edited by H. Nenrath and R. L. Hill, Academic Press, New York, (1976); N. Izumiya et al., *Peptide Gosei no Kiso to Jikken (Fundamentals and Experiments of Peptide Synthesis)*, Maruzen (1985); H. Yazima, S. Sakakibara et al., *Seikagaku Jikken Koza (Course of Biochemical Experiments)*, 1, edited by Biochemical Society of Japan, Tokyo Kagaku Dojin (1977); H. Kimura et al., *Zoku Seikagaku Jikken Koza (Course of Biochemical Experiments, second series)*, 2, edited by Biochemical Society of Japan, Tokyo Kagaku Dojin (1987); and J. M. Stewart and J. D. Young, *Solid Phase Peptide Synthesis*, Pierce Chemical Company, Illinois (1984), which describe azide methods, chloride methods, acid anhydride methods, mixed acid anhydride methods, DCC methods, active ester methods, methods using Woodward reagent K, carbodiimidazole methods, oxidation-reduction methods, DCC/HONB methods and methods using BOP reagents.

The cyclic peptide [I] of the present invention can be produced by condensing a first starting material having a reactive carboxyl group corresponding to one of two kinds of fragments which are separated at any position of its peptide bond with a second starting material having a reactive amino group corresponding to the other fragment, subsequently eliminating protective groups of the C-terminal α-carboxyl group and the N-terminal α-amino group of the resulting compound concurrently or stepwise, thereafter conducting intramolecular condensation of both by methods known in the art to obtain a cyclic compound, and then, eliminating protective groups by methods known in the art, if the resulting condensed product has any protective groups.

The above starting materials are usually amino acid and/or peptide fragments which, taken together, form the cyclic hexapeptide of the desired formula [I] or a salt thereof. They are usually linear or branched. The reactive carboxyl group means carboxyl group itself or an activated carboxyl group. The reactive amino group means amino group itself or an activated amino group. One of the two functional groups taking part in the condensation reaction is usually activated.

The carboxyl group and the amino group which do not take part in the condensation reaction are usually protected before the condensation reaction.

Protection of functional groups which should not affect the reaction of the starting materials, the protective groups and elimination of the protective groups, and activation of functional groups related to the reaction can also be suitably selected from groups or methods known in the art.

Examples of the protective groups for the amino groups of the starting materials include benzyloxycarbonyl, t-butyloxy-carbonyl, t-amyloxycarbonyl, isobornyloxycarbonyl, 4-methoxybenzyloxycarbonyl, 2-chlorobenzyloxycarbonyl, adamantyloxycarbonyl, trifluoroacetyl, phthalyl, formyl, 2-nitrophenylsulfenyl, diphenylphosphinothioyl and 9-fluorenylmethyloxycarbonyl. The protective groups for the carboxyl groups include, for example, alkyl esters (such as esters of methyl, ethyl, propyl, butyl, t-butyl, cyclo-pentyl, cyclohexyl, cycloheptyl, cyclooctyl and 2-adamantyl), benzyl esters, 4-nitrobenzyl esters, 4-methoxybenzyl esters, 4-chlorobenzyl esters, benzhydryl esters, phenacyl esters, benzyloxycarbonylhydrazide, t-butyloxycarbonylhydrazide and tritylhydrazide.

The hydroxyl group of serine can be protected, for example, by esterification or etherification. Examples of groups suitable for this esterification include lower aliphatic acyl groups such as acetyl, arylacyl groups such as benzoyl, and carbonic acid-derived groups such as benzyloxycarbonyl and ethyloxycarbonyl. Examples of groups suitable for the etherification include benzyl, tetrahydropyranyl and t-butyl. However, the hydroxyl group of serine is not always required to be protected.

Examples of the protective groups for the phenolic hydroxyl group of tyrosine include benzyl, 2,6-dichlorobenzyl, 2-nitrobenzyl, 2-bromobenzyloxycarbonyl and t-butyl. However, the phenolic hydroxyl group of tyrosine is not always required to be protected.

Methionine may be protected in the form of sulfoxides.

The protective groups for the imidazole ring of histidine include p-toluenesulfonyl, 4-methoxy-2,3,6-trimethylbenzenesulfonyl, 2,4-dinitrophenyl, benzyloxymethyl, t-butoxymethyl, t-butoxycarbonyl, trityl and 9-fluorenylmethyloxycarbonyl. However, the imidazole ring is not always required to be protected.

The protective groups for the indole ring of tryptophan include formyl, 2,4,6-trimethylbenzensulfonyl, 2,4,6-trimethoxybenzenesulfonyl, 4-methoxy-2,3,6-trimethylbenzenesulfonyl, 2,2,2-trichloroethyloxycarbonyl and diphenylphosphinothioyl. However, the indole ring is not always required to be protected.

Examples of the activated carboxyl groups of the starting materials include the corresponding acid anhydrides, azides and active esters (esters of alcohols such as pentachlorophenol, 2,4,5-trichlorophenol, 2,4-dinitrophenol, cyano-methyl alcohol, p-nitrophenol, N-hydroxy-5-norbornene-2,3-dicarboxyimide, N-hydroxysuccinimide, N-hydroxyphthalimide and N-hydroxybenzotriazole. Examples of the activated amino acid groups of the raw materials include the corresponding phosphoric acid amides.

Condensation reaction can be conducted in the presence of a solvent(s). The solvent(s) can be appropriately selected from the solvents commonly used in peptide condensation reactions. Examples of the solvents include anhydrous or hydrous dimethylformamide, dimethyl sulfoxide, pyridine, chloroform, dioxane, dichloromethane, tetrahydrofuran, acetonitrile, ethyl acetate, N-methylpyrrolidone and appropriate mixtures thereof.

The reaction temperature is appropriately selected from the temperature range commonly used in peptide bond-forming reactions, usually from the range of about −20° to about 30° C.

Intramolecular cyclization reaction can be conducted at any position of the peptide by methods known in the art. For example, the protective group of the C-terminal α-carboxyl group of the protected peptide is first eliminated by methods known in the art, and then, the carboxyl group is activated by methods known in the art, followed by elimination of the protective group of the N-terminal α-amino group by methods known in the art and intramolecular cyclization. The protective groups of the C-terminal α-carboxyl group and the N-terminal α-amino group of the protected peptide may be concurrently eliminated, followed by intramolecular cyclization according to known condensation reaction. In some cases, intramolecular cyclization reaction is preferably conducted in a highly diluted state.

Examples of methods for eliminating the protective groups include catalytic reduction in the presence of a catalyst such as palladium black or Pd-carbon in a stream of hydrogen, acid treatment with anhydrous hydrogen fluoride, methanesulfonic acid, trifluoromethanesulfonic acid, trifluoroacetic acid or mixtures thereof, and reduction with sodium in liquid ammonia. The elimination reaction by the above-mentioned acid treatment is generally conducted at a temperature between −20° and 40° C. In the acid treatment, it is effective to add a cation trapping agent such as anisole, phenol, thioanisole, m-cresol, p-cresol, dimethylsulfide, 1,4-butanedithiol or 1,2-ethanedithiol. The 2,4-dinitrophenyl group used as the protective group for the imidazole ring of histidine is eliminated by thiophenol treatment. The formyl group used as the protective group for the indole ring of tryptophan may be eliminated by either (i) alkali treatment using dilute sodium hydroxide, dilute ammonia or the like, or (ii) the above-mentioned elimination by the acid treatment in the presence of 1,2-ethanedithiol, 1,4-butanedithiol or the like.

After completion of the reaction, the cyclic peptide [I] thus obtained is collected by conventional separation and purification methods of peptides such as extraction, distribution, reprecipitation, recrystallization, column chromatography and high performance liquid chromatography.

The cyclic peptides [I] of the present invention can be obtained by methods known in the art as the metal salts, the salts of bases or basic compounds, the inorganic acid addition salts, the organic acid salts and the like, and particularly as pharmaceutically acceptable acid addition salts such as the salts of inorganic acids (for example, hydrochloric acid, sulfuric acid and phosphoric acid) or organic acids (for example, acetic acid, propionic acid, citric acid, tartaric acid, malic acid, oxalic acid and methanesulfonic acid).

In this specification, amino acids and peptides are indicated by the abbreviations commonly used in the art or adopted by the IUPAC-IUB Commission on Biochemical Nomenclature. For example, the following abbreviations are used:

| | |
|---|---|
| Gly | Glycine |
| Sar | Sarcosine (N-methylglycine) |
| Ala | Alanine |
| Val | Valine |
| Nva | Norvaline |
| Ile | Isoleucine |
| aIle | Alloisoleucine |
| Nle | Norleucine |
| Leu | Leucine |
| N-MeLeu | N-Methylleucine |
| tLeu | t-Leucine |
| γMeLeu | γ-Methylleucine |
| Met | Methionine |
| Arg | Arginine |
| Arg(Tos) | $N^g$-p-Toluenesulfonylarginine |
| Lys | Lysine |
| Lys(Mtr) | $N(\epsilon)$-(4-Methoxy-2,3,6-trimethylbenzenesulfonyl)lysine |
| Orn | Ornithine |
| Orn(COPh) | $N(\delta)$-Benzoylornithine |
| Orn(COCH$_2$Ph) | $N(\delta)$-Phenylacetylornitine |
| Orn(COCH$_2$CH$_2$Ph) | $N(\delta)$-(3-Phenylpropionyl)ornithine |
| Orn(COCH$_2$—Ind) | $N(\delta)$-({Indole-3-yl}acetyl)ornithine |
| His | Histidine |
| His(Bom) | $N(\pi)$-Benzyloxymethylhistidine |
| His(Bzl) | $N(\tau)$-Benzylhistidine |
| Asp | Aspartic acid |
| Asn(CH$_2$Ph) | $N^4$-Benzylasparagine |
| Asn(CH$_2$CH$_2$Ph) | $N^4$-Phenethylasparagine |
| Asn(CH$_2$CH$_2$—Ind) | $N^4$-(2-{Indole-3-yl}ethyl)asparagine |
| Asn(Me.CH$_2$CH$_2$Ph) | $N^4$-Methyl-$N^4$-phenethylasparagine |
| Asn(CH$_2$CHMePh) | $N^4$-({2-phenyl}propyl)asparagine |
| Asp(R1) | Aspartic acid β-4-phenylpiperazineamide |
| Asp(R2) | Aspartic acid β-4-phenylpiperidineamide |
| Asp(R3) | Aspartic acid β-indolineamide |
| Asp(R4) | Aspartic acid β-1-aminoindanamide |

| | |
|---|---|
| Asp(R5) | Aspartic acid β-1-aminotetrahydro-naphthaleneamide |
| Asp(R6) | Aspartic acid β-4-acetylpiperazine-amide |
| Glu | Glutamic acid |
| Gln(CH$_2$Ph) | N$^5$-Benzylglutamine |
| Gln(CH$_2$CH$_2$Ph) | N$^5$-Phenethylglutamine |
| Gln(CH$_2$CH$_2$—Ind) | N$^5$-(2-{Indole-3-yl}ethyl)glutamine |
| Glu(R3) | Glutamic acid γ-indolineamide |
| Glu(R4) | Glutamic acid γ-1-aminoindanamide |
| Glu(R5) | Glutamic acid γ-1-aminotetrahydro-naphthaleneamide |
| Cys | Cysteine |
| Cta | Cysteic acid |
| Ser | Serine |
| Ser(Bzl) | O-Benzylserine |
| Thr | Threonine |
| Thr(Bzl) | O-Benzylthreonine |
| Pro | Proline |
| Tpr | Thioproline |
| Hys | 4-Hydroxyproline |
| Hys(Bzl) | 4-Benzyloxyproline |
| Azc | Azetidine-2-carboxylic acid |
| Pip | Pipecolic acid (piperidine-2-carboxylic acid) |
| Phe | Phenylalanine |
| N-MePhe | N-Methylphenylalanine |
| Tyr | Tyrosine |
| Trp | Tryptophan |
| mTrp | 5-Methyltryptophan |
| N-MeTrp | N(α)-Methyltryptophan |
| Trp(Me) | N$^{in}$-Methyltryptophan |
| Trp(For) | N$^{in}$-Formyltryptophan |
| Trp(Ac) | N$^{in}$-Acetyltryptophan |
| Phg | Phenylglycine |
| Nal(1) | 1-Naphthylalanine |
| Nal(2) | 2-Naphthylalanine |
| Thi | 2-Thienylalanine |
| Thg(2) | 2-Thienylglycine |
| Thg(3) | 3-Thienylglycine |
| Acpr | 1-Aminocyclopropane-1-carboxylic acid |
| Acbu | 1-Aminocyclobutane-1-carboxylic acid |
| Acpe | 1-Aminocyclopentane-1-carboxylic acid |
| Achx | 1-Aminocyclohexane-1-carboxylic acid |
| Achp | 1-Aminocycloheptane-1-carboxylic acid |
| Tic | Tetrahydroisoquinoline-2-carboxylic acid |

| | |
|---|---|
| AcOEt | Ethyl acetate |
| Boc | t-Butoxycarbonyl |
| Bzl | Benzyl |
| BrZ | 2-Bromobenzyloxycarbonyl |
| Clz | 2-Chlorobenzyloxycarbonyl |
| Tos | p-Toluenesulfonyl |
| For | Formyl |
| OBzl | Benzyl ester |
| OPac | Phenacyl ester |
| ONB | HONB ester |
| TFA | Trifluoroacetic acid |
| TEA | Triethylamine |
| IBCF | Isobutyl chloroformate |
| DMF | N,N-Dimethylformamide |
| DCC | N,N'-Dicyclohexylcarbodiimide |
| DCU | N,N'-Dicyclohexylurea |
| HONB | N-Hydroxy-5-norbornene-2,3-dicarboxy-imide |
| HOBt | 1-Hydroxybenzotriazole |
| DCM | Dichloromethane |
| THF | Tetrahydrofuran |

The cyclic peptides of the present invention have the following pharmacological activity. Namely, the novel cyclic peptides [I] of the present invention or the pharmaceutically acceptable salts thereof have the antagonistic activity on endothelin receptors as shown in the experimental examples described below. Further, the certain group of cyclic peptides [I] or pharmaceutically acceptable salt thereof also have the antagonistic activity on NK2 receptors.

The cyclic peptides [I] or pharmaceutically acceptable salt thereof can be used as prophylactic and therapeutic drugs for hypertension, cardiac or cerebral circulatory diseases, renal diseases, asthma and the like, because they have the antagonistic activity on endothelin receptors. Further, the cyclic peptides [I] or pharmaceutically acceptable salt thereof having the antagonistic activity on NK2 receptors in addition can also be used as anti-inflammatory drugs and antarthritics.

Recent investigations on the endothelin receptors revealed that the endothelin receptors have two subtypes ($ET_A$ and $ET_B$) [for example, the Twelfth Medicinal Chemistry Symposium-the First Annual Meeting of the Medical Chemistry Section, Okayama, Dec. 4 to 6, 1991, Summaries of Lectures, page 82 (Lecture No. P-20); the Third Endothelin Symposium, Tsukuba, Dec. 13 and 14, 1991, Summaries of Lectures, (Lecture No. P-05); and *Nature*, 348, 730–735 (1990)]. Preferred novel cyclic peptides [I] of the present invention strongly bind not only to $ET_A$, but also to $ET_B$ to act as the antagonists on endothelin receptors, as shown in the experimental examples described below. Further, the certain group of the novel cyclic peptides [I] of the present invention have the antagonistic activity on NK2 receptors, one of tachykinin peptide receptors, in addition. As the tachykinin family, substance P, neurokinin A and neurokinin B are known [Y. Yokoto et al., *J. Biol. Chem.*, 264, 17649 (1989); A. D. Hershey et al., *Science*, 247, 958 (1990); Y. Sasai et al., *Biochem. Biophys. Res. Commun.*, 165, 695 (1989); R. Shigemoto et al., *J. Biol. Chem.*, 265, 623 (1990); and A. Graham et al., *Biochem. Biophys. Res. Commun.*, 177, 8 (1991)], and NK1, NK2 and NK3 are known respectively, as receptors corresponding to ligands thereof. Antagonists on NK receptors are described in Japanese Patent Unexamined Publication Nos. 2197/1991, 17098/1991 and 141295/1991. However, the compounds disclosed therein are different from the cyclic hexapeptides [I] of the present invention in structure.

The novel cyclic peptides [I] of the present invention have the remarkable effect of suppressing the vasopressor activity of endothelin as the antagonists on endothelin receptors, and some of them also have the strong activity as the antagonists on NK2 receptors. For this reason, the novel cyclic peptides of the present invention or the salts thereof can be used as prophylactic and therapeutic drugs for hypertension, cardiac or cerebral circulatory diseases (for example, cardiac infarction), renal diseases for example, acute renal insufficiency), asthma and the like. Further, the cyclic peptides having the antagonistic activity on NK2 receptors in addition can also be used as the anti-inflammatory drugs and the antarthritics.

The cyclic peptides of the present invention, when used as the above-mentioned prophylactic and therapeutic drugs, can be safely administered orally or parenterally in the form of powders, granules, tablets, capsules, injections, suppositories, ointments or sustained release preparations, alone or in combination with pharmaceutically acceptable carriers, excipients or diluents. The peptides of the present invention are typically administered parenterally, for example, by intravenous or subcutaneous injection, intraventricular or intraspinal administration, nasotracheal administration or intrarectal administration. In some cases, however, they are administered orally.

The cyclic peptides of the present invention are generally stable substances, and therefore, can be stored as physiological saline solutions. It is also possible to lyophilize the peptides, store them in ampules with mannitol or sorbitol, and dissolve them in a suitable carrier at the time of use. The cyclic peptides of the present invention can be given in their free forms, or in the form of base salts or acid addition salts thereof. All of the free cyclic peptides, the base salts and the acid addition salts thereof are generally given in a proper dose within the range of 1 μg to 100 mg of free peptide per kg of weight. More specifically, although the dosage varies depending on the type of disease to be treated, the symptom of the disease, the object to which the drugs are given and the route of administration, when given by injection to adult patients of hypertension, for example, it is advantageous that the active ingredients (the peptides [I] or pharmaceutically acceptable salt thereof) are normally given in one dose of about 1 μg to 100 mg/kg of weight, more preferably about 100 μg to 20 mg/kg of weight, most preferably 1 mg to 20 mg/kg of weight, about once to 3 times a day. In injection, the peptides [I] are usually given intravenously. Drip infusion is also effective. In this case, the total dosage is the same as with injection.

When the cyclic peptides of the present invention or the pharmaceutically acceptable salts thereof are used as the prophylactic or therapeutic drugs, they must be carefully purified so as to contain no bacteria and no pyrogens.

The present invention will be described in more detail with the following examples and experimental examples, in which all amino acid residues take the L-form unless otherwise specified, when they have the D- and L-forms.

In the following examples, SILICAGEL 60F-254 (Merck) was used as the plates of thin layer chromatography, and chloroform-methanol (19:1) and chloroform-methanol-acetic acid (9:1:0.5) were used as the developing solvents for $Rf_1$ and $Rf_2$, respectively.

EXAMPLE 1

Production of cyclo[-D-Asp-Ala-Asp-D-Leu-Leu-D-Trp-]

(1) Production of Boc-D-Leu-Leu-OBzl

H-Leu-OBzl.pTos (21.6 g) was dissolved in DMF (100 ml), and the solution was cooled with ice. TEA (7.7 ml) and Boc-D-Leu-ONB [prepared from Boc-D-Leu-OH.H$_2$O (12.5 g), HONB (9.86 g) and DCC (11.4 g) were added thereto, followed by stirring overnight. The resulting DCU was separated by filtration, and the filtrate was concentrated to obtain a residue. The residue was dissolved in AcOEt, and the resulting solution was washed with 4% aqueous NaHCO$_3$ and 10% aqueous citric acid. After washing with water, the solution was dried with Na$_2$SO$_4$ and concentrated. Ether was added to the resulting residue to separate out a precipitate, which was collected by filtration.

Yield: 19.8 g (91.3%), Melting point: 94°–95° C., $Rf_2$: 0.76 $[\alpha]_D^{25}$ +3.6° (c=1.06, in DMF)

Elemental analysis: As C$_{24}$H$_{38}$N$_2$O$_5$ Calculated: C, 66.33; H, 8.81; N, 6.45 Found: C, 66.38; H, 8.87; N, 6.53

(2) Production of Boc-D-Leu-Leu-OPac

Boc-D-Leu-Leu-OBzl (6.0 g) was dissolved in methanol (20 ml) and catalytically reduced in a stream of hydrogen using 10% Pd-carbon as a catalyst. After the catalyst was separated by filtration, the solution was concentrated to obtain a residue. The residue and Cs$_2$CO$_3$ (2.1 g) were dissolved in 90% aqueous methanol, and the solution was concentrated. The resulting residue was dissolved in DMF (60 ml), and phenacyl bromide (2.8 g) was added thereto, followed by stirring overnight. The resulting TEA hydrochloride was separated by filtration, and the filtrate was concentrated to obtain a residue. The residue was dissolved in AcOEt, and the resulting solution was washed with 4% aqueous NaHCO$_3$ and 10% aqueous citric acid. After washing with water, the solution was dried with Na$_2$SO$_4$ and concentrated. Ether was added to the resulting residue to separate out a precipitate, which was collected by filtration.

Yield: 5.48 g (85.8%), Melting point: 98°–99° C., $Rf_2$: 0.66 $[\alpha]_D^{25}$ −3.9° (c=1.09, in DMF)

Elemental analysis: As C$_{25}$H$_{38}$N$_2$O$_6$ Calculated: C, 64.91; H, 8.28; N, 6.06 Found: C, 65.21; H, 8.54; N, 6.24

(3) Production of Boc-Asp(OBzl)-D-Leu-Leu-OPac

TFA (20 ml) was added to Boc-D-Leu-Leu-OPac (1.85 g) to dissolve it, followed by concentration. 4% aqueous NaHCO$_3$ was added thereto to adjust the pH to 9–10, and then, extraction was conducted using AcOEt. The extract was dried with Na$_2$SO$_4$, concentrated and dried. The resulting product was dissolved in DMF (15 ml) and cooled with ice. Then, TEA (0.56 ml) was added thereto. Boc-Asp(OBzl)-ONB [prepared from Boc-Asp(OBzl)-OH (1.42 g), HONB (0.86 g) and DCC (0.99 g)] was added thereto, followed by stirring overnight. The resulting insoluble material was separated by filtration, followed by concentration. The residue was dissolved in AcOEt, and the solution was washed with water, 10% aqueous citric acid and 4% aqueous NaHCO$_3$. After washing with water, the solution was dried with Na$_2$SO$_4$ and concentrated. Ether was added to the resulting residue to separate out a precipitate, which was collected by filtration.

Yield: 2.31 g (86.5%), Melting point: 119°–121° C., $Rf_1$: 0.57, $Rf_2$: 0.79 $[\alpha]_D^{28}$ −40.8° (c=0.93, in DMF)

Elemental analysis: As C$_{36}$H$_{49}$N$_3$O$_9$ Calculated: C, 64.75; H, 7.40; N, 6.29 Found: C, 64.73; H, 7.41; N, 6.45

(4) Production of Boc-Ala-Asp(OBzl)-D-Leu-Leu-OPac

TFA (20 ml) was added to Boc-Asp(OBzl)-D-Leu-Leu-OPac (2.14 g) to dissolve it, followed by concentration. 8-N HCl/dioxane (1.00 ml) was added thereto, and ether was added to precipitate crystals. The crystals were separated by filtration and dried. The resulting product was dissolved in DMF (15 ml) and cooled with ice. Then, TEA (0.90 ml) was added thereto. Boc-Ala-ONB [prepared from Boc-Ala-OH (0.61 g), HONB (0.63 g) and DCC (0.73 g)] was added thereto, followed by stirring overnight. The resulting insoluble material was separated by filtration, followed by concentration. The residue was dissolved in AcOEt, and the solution was washed with water, 10% aqueous citric acid and 4% aqueous NaHCO$_3$. After washing with water, the solution was dried with Na$_2$SO$_4$ and concentrated. Ether was added to the resulting residue to separate out a precipitate, which was collected by filtration.

Yield: 2 28 g (96 4%), Melting point: 132°–133° C., $Rf_1$: 0.34, $Rf_2$: 0.66 $[\alpha]_D^{28}$ −46.6° (c=0.76, in DMF)

Elemental analysis: As C$_{39}$H$_{54}$N$_4$O$_{10}$ Calculated: C, 63.40; H, 7.37; N, 7.58 Found: C, 63.15; H, 7.44; N, 7.66

(5) Production of Boc-D-Asp(OBzl)-Ala-Asp(OBzl)-D-Leu-Leu-OPac

TFA (20 ml) was added to Boc-Ala-Asp(OBzl)-D-Leu-Leu-OPac (1.77 g) to dissolve it, followed by concentration. 8-N HCl/dioxane (0.75 ml) was added thereto, and ether was added to precipitate crystals. The crystals were separated by filtration and dried. The resulting product was dissolved in DMF (15 ml) and cooled with ice. Then, TEA (0.67 ml) was added thereto. Boc-D-Asp(OBzl)-ONB [prepared from Boc-D-Asp(OBzl)-OH (0.85 g), HONB (0.51 g) and DCC (0.60 g)] was added thereto, followed by stirring overnight. The resulting insoluble material was separated by filtration, followed by concentration. The residue was dissolved in AcOEt, and the solution was washed with water, 10% aqueous citric acid and 4% aqueous NaHCO$_3$. After washing with water, the solution was dried with Na$_2$SO$_4$ and concentrated. Ether was added to the resulting residue to separate out a precipitate, which was collected by filtration.

Yield: 2.08 g (91.8%), Melting point: 92°–94° C., $Rf_1$: 0.38, $Rf_2$: 0.70 $[\alpha]_D^{28}$ −21.0° (c=0.64, in DMF)

Elemental analysis: As $C_{50}H_{65}N_5O_{13}$ Calculated: C, 63.61; H, 6.94; N, 7.42 Found: C, 63.33; H, 6.98; N, 7.52

(6) Production of Boc-D-Trp-D-Asp(OBzl)-Ala-Asp(OBzl)-D-Leu-Leu-OPac

TFA (20 ml) was added to Boc-D-Asp(OBzl)-Ala-Asp(OBzl)-D-Leu-Leu-OPac (1.60 g) to dissolve it, followed by concentration. 8-N HCl/dioxane (0.53 ml) was added thereto, and ether was added to precipitate crystals. The crystals were separated by filtration and dried. The resulting product was dissolved in DMF (15 ml), and cooled with ice. Then, TEA (0.48 ml) was added thereto. Boc-D-Trp-ONB [prepared from Boc-D-Trp-OH (0.57 g), HONB (0.37 g) and DCC (0.42 g)] was added thereto, followed by stirring overnight. The resulting insoluble material was separated by filtration, followed by concentration. The residue was dissolved in AcOEt, and the solution was washed with water, 10% aqueous citric acid and 4% aqueous $NaHCO_3$. After washing with water, the solution was dried with $Na_2SO_4$ and concentrated. Ether was added to the resulting residue to separate out a precipitate, which was collected by filtration.

Yield: 1.61 g (83.8%), Melting point: 160°–162° C., $Rf_1$: 0.35, $Rf_2$: 0.68 $[\alpha]_D^{28}$ +17.5° (c=0.71, in DMF)

Elemental analysis: As $C_{61}H_{75}N_7O_{14}$ Calculated: C, 64.82; H, 6.69; N, 8.67 Found: C, 64.70; H, 6.72; N, 8.81

(7) Production of Boc-D-Trp-D-Asp(OBzl)-Ala-Asp(BOzl)-D-Leu-Leu-OH

Boc-D-Trp-D-Asp(OBzl)-Ala-Asp(OBzl)-D-Leu-Leu-OPac (1.47 g) was dissolved in 90% aqueous AcOH (20 ml), and Zn powder (4.26 g) was added thereto, followed by stirring for 3 hours. The Zn powder was separated by filtration, and the filtrate was concentrated. AcOEt was added to the residue to dissolve it, and the solution was washed with 10% aqueous citric acid. After washing with water, the solution was dried with $Na_2SO_4$ and concentrated. Ether was added to the resulting residue to separate out a precipitate, which was collected by filtration.

Yield: 1.23 g (93.5%), Melting point: 195°–196° C., $Rf_1$: 0.14, $Rf_2$: 0.67 $[\alpha]_D^{28}$ +27.1° (c=0.65, in DMF)

Elemental analysis: As $C_{53}H_{69}N_7O_{13}$ Calculated: C, 62.89; H, 6.87; N, 9.69 Found: C, 63.02; H, 6.57; N, 9.68

(8) Production of cyclo[-D-Asp-Ala-Asp-D-Leu-Leu-D-Trp-]

Boc-D-Trp-D-Asp(OBzl)-Ala-Asp(OBzl)-D-Leu-Leu-OH (0.51 g) was dissolved in DCM (20 ml), and the solution was cooled with ice. HONB (0.18 g) and DCC (0.21 g) were added thereto, followed by stirring for 3 hours. Then, the resulting DCU was separated by filtration, followed by concentration, and ether was added to the residue to separate out a precipitate, which was collected by filtration. Ethanedithiol (0.09 ml) and 8-N HCl/dioxane (20 ml) were added thereto under ice cooling to dissolve the precipitate. The resulting solution was stirred for 10 minutes and concentrated. Then, ether was added to the residue to separate out a precipitate, which was collected by filtration and dried. The precipitate was dissolved in DMF (10 ml), and the resulting solution was added dropwise to DMF (90 ml) containing TEA (0.7 ml) for 30 minutes, followed by stirring overnight and concentration. Acetonitrile was added to the resulting residue to separate out a precipitate, which was collected by filtration and dried. Of this precipitate, 89 mg was dissolved in DMF (15 ml), and catalytically reduced in a stream of hydrogen using palladium black as a catalyst. The catalyst was separated by filtration, and the filtrate was concentrated. The resulting residue was dissolved in a small amount of AcOH, and then, water was added thereto to conduct lyophilization. Finally, the lyophilized product was purified by liquid chromatography using a YMC-D-ODS-5 column (2 cm×25 cm) (Y.M.C.) to obtain a desired material. The yield was 13.6 mg (18.2%).

Anal. for amino acids [6-N HCl, 110° C., hydrolysis for 24 hours; figures in parentheses show theoretical values.]: Asp 2.00(2); Ala 1.06(1); Leu 2.11(2) LSIMS $(M+H^+)$=714, (theoretical value)=714

EXAMPLE 2

Production of cyclo[-D-Asp-Ala-D-Asp-D-Leu-Leu-D-Trp-]

(1) Production of Boc-D-Asp(OBzl)-D-Leu-Leu-OPac

TFA (20 ml) was added to Boc-D-Leu-Leu-OPac (1.85 g) prepared in EXAMPLE 1 (2) to dissolve it, followed by concentration. 4% aqueous $NaHCO_3$ was added thereto to adjust the pH to 9–10, and then, extraction was conducted using AcOEt. The extract was dried with $Na_2SO_4$ and concentrated. The resulting product was dissolved in DMF (15 ml) and cooled with ice. Then, TEA (0.56 ml) was added thereto. Boc-D-Asp(OBzl)-ONB [prepared from Boc-D-Asp(OBzl)-OH (1.42 g), HONB (0.86 g) and DCC (0.99 g)] was added thereto, followed by stirring overnight. The resulting insoluble material was separated by filtration, followed by concentration. The residue was dissolved in AcOEt, and the solution was washed with water, 10% aqueous citric acid and 4% aqueous $NaHCO_3$. After washing with water, the solution was dried with $Na_2SO_4$ and concentrated. Ether was added to the resulting residue to separate out a precipitate, which was collected by filtration.

Yield: 2.58 g (96.4%), Melting point: 113°–114° C., $Rf_1$: 0.51, $Rf_2$: 0.75 $[\alpha]_D^{28}$ +14.2° (c=1.23, in DMF)

Elemental analysis: As $C_{36}H_{49}N_3O_9$ Calculated: C, 64.75; H, 7.40; N, 6.29 Found: C, 64.78; H, 7.50; N, 6.47

(2) Production of Boc-Ala-D-Asp(OBzl)-D-Leu-Leu-OPac

TFA (20 ml) was added to Boc-D-Asp(OBzl)-D-Leu-Leu-OPac (2.14 g) to dissolve it, followed by concentration. 8N-HCl/dioxane (1.00 ml) was added thereto, and ether was added to precipitate crystals. The crystals were separated by filtration and dried. The resulting product was dissolved in DMF (15 ml) and cooled with ice. Then, TEA (0.90 ml) was added thereto. Boc-Ala-ONB [prepared from Boc-Ala-OH (0.61 g), HONB (0.63 g) and DCC (0.73 g)] was added thereto, followed by stirring overnight. The resulting insoluble material was separated by filtration, followed by concentration. The residue was dissolved in AcOEt, and the solution was washed with water, 10% aqueous citric acid and 4% aqueous $NaHCO_3$. After washing with water, the solution was dried with $Na_2SO_4$ and concentrated. Ether was added to the resulting residue to separate out a precipitate, which was collected by filtration.

Yield: 2.08 g (88.0%), Melting point: 167°–168° C., $Rf_1$: 0.36, $Rf_2$: 0.67 $[\alpha]_D^{28}$ +5.99° (c=0.94, in DMF)

Elemental analysis: As $C_{39}H_{54}N_4O_{10}$ Calculated: C, 63.40; H, 7.37; N, 7.58 Found: C, 63.32; H, 7.47; N, 7.74

(3) Production of Boc-D-Asp(OBzl)-Ala-D-Asp(BOzl)-D-Leu-Leu-OPac

TFA (20 ml) was added to Boc-Ala-D-Asp(OBzl)-D-Leu-Leu-OPac (1.77 g) to dissolve it, followed by concentration. 8N-HCl/dioxane (0.75 ml) was added thereto, and ether was added to precipitate crystals. The crystals were separated by filtration and dried. The resulting product was dissolved in DMF (15 ml) and cooled with ice. Then, TEA (0.67 ml) was added thereto. Boc-D-Asp(OBzl)-ONB [prepared from Boc-D-Asp(OBzl)-OH (0.85 g), HONB (0.51 g) and DCC (0.60 g)] was added thereto, followed by stirring overnight. The resulting insoluble material was separated by filtration, followed by concentration. The residue was dissolved in AcOEt, and the solution was washed with water, 10% aqueous citric acid and 4% aqueous NaHCO₃. After washing with water, the solution was dried with Na₂SO₄ and concentrated. Ether was added to the resulting residue to separate out a precipitate, which was collected by filtration.

Yield: 1.79 g (79 0%), Melting point: 120°–121° C., Rf₁: 0.37, Rf₂: 0.70 [α]$_D^{28}$ +34.2° (c=0.85, in DMF)

Elemental analysis: As $C_{50}H_{65}N_5O_{13}$ Calculated: C, 63.61; H, 6.94; N, 7.42 Found: C, 63.70; H, 6.89; N, 7.63

(4) Production of Boc-D-Trp-D-Asp(OBzl)-Ala-D-Asp-(BOzl)-D-Leu-Leu-OPac

TFA (20 ml) was added to Boc-D-Asp(OBzl)-Ala-D-Asp(OBzl)-D-Leu-Leu-OPac (1.60 g) to dissolve it, followed by concentration. 8N-HCl/dioxane (0.53 ml) was added thereto, and ether was added to precipitate crystals. The crystals were separated by filtration and dried. The resulting product was dissolved in DMF (15 ml) and cooled with ice. Then, TEA (0.48 ml) was added thereto. Boc-D-Trp-ONB [prepared from Boc-D-Trp-OH (0.57 g), HONB (0.37 g) and DCC (0.42 g)] was added thereto, followed by stirring overnight. The resulting insoluble material was separated by filtration, followed by concentration. The residue was dissolved in AcOEt, and the solution was washed with water, 10% aqueous citric acid and 4% aqueous NaHCO₃. After washing with water, the solution was dried with Na₂SO₄ and concentrated. Ether was added to the resulting residue to separate out a precipitate, which was collected by filtration.

Yield: 1 62 g (84 3%), Melting point: 178°–179° C., Rf₁: 0.37, Rf₂: 0.69 [α]$_D^{28}$ +41.1° (c=0.84, in DMF)

Elemental analysis: As $C_{61}H_{75}N_7O_{14}$ Calculated: C, 64.82; H, 6.69; N, 8.67 Found: C, 64.69; H, 6.74; N, 8.88

(5) Production of Boc-D-Trp-D-Asp(OBzl)-Ala-D-Asp-(BOzl)-D-Leu-Leu-OH

Boc-D-Trp-D-Asp(OBzl)-Ala-D-Asp(BOzl)-D-Leu-Leu-OPac (1.47 g) was dissolved in 90% aqueous AcOH (20 ml), and Zn powder (4.26 g) was added thereto, followed by stirring for 3 hours. The Zn powder was separated by filtration, and the filtrate was concentrated. AcOEt was added to the residue to dissolve it, and the solution was washed with 10% aqueous citric acid. After washing with water, the solution was dried with Na₂SO₄ and concentrated. Ether was added to the resulting residue to separate out a precipitate, which was collected by filtration.

Yield: 1.23 g (93.5%), Melting point: 165°–166° C., Rf₁: 0.17, Rf₂: 0.67 [α]$_D^{28}$ +54.5° (c=1.05, in DMF)

Elemental analysis: As $C_{53}H_{69}N_7O_{13}$ Calculated: C, 62.89; H, 6.87; N, 9.69 Found: C, 62.59; H, 7.05; N, 9.63

(6) Production of cyclo[-D-Asp-Ala-D-Asp-D-Leu-Leu-D-Trp-]

Boc-D-Trp-D-Asp(OBzl)-Ala-D-Asp(BOzl)-D-Leu-Leu-OH (0.51 g) was dissolved in DCM (20 ml), and the solution was cooled with ice. HONB (0.18 g) and DCC (0.21 g) were added thereto, followed by stirring for 3 hours. Then, the resulting DCU was separated by filtration, followed by concentration, and ether was added to the residue to separate out a precipitate, which was collected by filtration. Ethanedithiol (0.09 ml) and 8N-HCl/dioxane (20 ml) were added thereto under ice cooling to dissolve the precipitate. The resulting solution was stirred for 10 minutes and concentrated. Then, ether was added to the residue to separate out a precipitate, which was collected by filtration and dried. The precipitate was dissolved in DMF (10 ml), and the resulting solution was added dropwise to DMF (90 ml) containing TEA (0.7 ml) for 30 minutes, followed by stirring overnight and concentration. Acetonitrile was added to the resulting residue to separate out a precipitate, which was collected by filtration and dried. Of this precipitate, 89 mg was dissolved in DMF (15 ml) and catalytically reduced in a stream of hydrogen using palladium black as a catalyst. The catalyst was separated by filtration, and the filtrate was concentrated. The resulting residue was dissolved in a small amount of AcOH, and then, water was added thereto to conduct lyophilization. Finally, the lyophilized product was purified by liquid chromatography using a YMC-D-ODS-5 column (2 cm×25 cm) (Y.M.C.) to obtain a desired material. The yield was 23.4 mg (15.3%).

Anal. for amino acids [6N-HCl, 110° C., hydrolysis for 24 hours; figures in parentheses show theoretical values.]: Asp 2.00(2); Ala 1.04(1); Leu 2.07(2) LSIMS (M+H⁺)=714, (theoretical value)=714

EXAMPLE 3

Production of cyclo[-D-Asp-Ala-Glu-D-Leu-Leu-D-Trp-]

(1) Production of Boc-Glu(OBzl)-D-Leu-Leu-OPac

TFA (20 ml) was added to Boc-D-Leu-Leu-OPac (1.85 g) prepared in example 1 (2) to dissolve it, followed by concentration. 4% aqueous NaHCO₃ was added thereto to adjust the pH to 9–10, and then, extraction was conducted using AcOEt. The extract was dried with Na₂SO₄ and concentrated. The resulting product was dissolved in DMF (15 ml) and cooled with ice. Then, TEA (0.56 ml) was added thereto. Boc-Glu(OBzl)-ONB [prepared from Boc-Glu-(OBzl)-OH (1.48 g), HONB (0.86 g) and DCC (0.99 g)] was added thereto, followed by stirring overnight. The resulting insoluble material was separated by filtration, followed by concentration. The residue was dissolved in AcOEt, and the solution was washed with water, 10% aqueous citric acid and 4% aqueous NaHCO₃. After washing with water, the solution was dried with Na₂SO₄ and concentrated. Ether was added to the resulting residue to separate out a precipitate, which was collected by filtration.

Yield: 2.04 g (74.5%), Melting point: 118°–120° C., Rf₁: 0.41, Rf₂: 0.71 [α]$_D^{28}$ −23.8° (c=0.84, in DMF)

Elemental analysis: As $C_{37}H_{51}N_3O_9$ Calculated: C, 65.18; H, 7.54; N, 6.16 Found: C, 65.20; H, 7.73; N, 6.34

(2) Production of Boc-Ala-Glu(OBzl)-D-Leu-Leu-OPac

TFA (20 ml) was added to Boc-Glu(OBzl)-D-Leu-Leu-OPac (1.91 g) to dissolve it, followed by concentration. 8N-HCl/dioxane (0.88 ml) was added thereto, and ether was added to precipitate crystals. The crystals were separated by filtration and dried. The resulting product was dissolved in DMF (15 ml) and cooled with ice. Then, TEA (0.90 ml) was added thereto. Boc-Ala-ONB [prepared from Boc-Ala-OH (0.53 g), HONB (0.55 g) and DCC (0.64 g)] was added thereto, followed by stirring overnight. The resulting insoluble material was separated by filtration, followed by concentration. The residue was dissolved in ACOEt, and the solution was washed with water, 10% aqueous citric acid and 4% aqueous NaHCO₃. After washing with water, the solution was dried with Na₂SO₄ and concentrated. Ether was added to the resulting residue to separate out a precipitate, which was collected by filtration.

Yield: 2.00 g (94.9%), Melting point: 129°–130° C., Rf₁: 0.36, Rf₂: 0.67 [α]$_D^{28}$ −32.9° (c=1.03, in DMF)

Elemental analysis: As $C_{40}H_{56}N_4O_{10}$ Calculated: C, 63.81; H, 7.50; N, 7.44 Found: C, 63.70; H, 7.55; N, 7.62

(3) Production of Boc-D-Asp(OBzl)-Ala-Glu(BOzl)-D-Leu-Leu-OPac

TFA (20 ml) was added to Boc-Ala-Glu(OBzl)-D-Leu-Leu-OPac (1.81 g) to dissolve it, followed by concentration.

8N-HCl/dioxane (0.75 ml) was added thereto, and ether was added to precipitate crystals. The crystals were separated by filtration and dried. The resulting product was dissolved in DMF (15 ml) and cooled with ice. Then, TEA (0.67 ml) was added thereto. Boc-D-Asp(OBzl)-ONB [prepared from Boc-D-Asp(OBzl)-OH (0.85 g), HONB (0.51 g) and DCC (0.60 g)] was added thereto, followed by stirring overnight. The resulting insoluble material was separated by filtration, followed by concentration. The residue was dissolved in AcOEt, and the solution was washed with water, 10% aqueous citric acid and 4% aqueous $NaHCO_3$. After washing with water, the solution was dried with $Na_2SO_4$ and concentrated. Ether was added to the resulting residue to separate out a precipitate, which was collected by filtration.

Yield: 2 07 g (90 0%), Melting point: 149°–151° C., $Rf_1$: 0.34, $Rf_2$: 0.69 $[\alpha]_D^{28}$ +3.00° (c=1.14, in DMF)

Elemental analysis: As $C_{51}H_{67}N_5O_{13}$ Calculated: C, 63.93; H, 7.05; N, 7.31 Found: C, 64.01; H, 7.11; N, 7.48

(4) Production of Boc-D-Trp-D-Asp(OBzl)-Ala-Glu(BOzl)-D-Leu-Leu-OPac

TFA (20 ml) was added to Boc-D-Asp(OBzl)-Ala-Glu-(OBzl)-D-Leu-Leu-OPac (1.63 g) to dissolve it, followed by concentration. 8N-HCl/dioxane (0.53 ml) was added thereto, and ether was added to precipitate crystals. The crystals were separated by filtration and dried. The resulting product was dissolved in DMF (15 ml) and cooled with ice. Then, TEA (0.48 ml) was added thereto. Boc-D-Trp-ONB [prepared from Boc-D-Trp-OH (0.57 g), HONB (0.37 g) and DCC (0.42 g)] was added thereto, followed by stirring overnight. The resulting insoluble material was separated by filtration, followed by concentration. The residue was dissolved in AcOEt, and the solution was washed with water, 10% aqueous citric acid and 4% aqueous $NaHCO_3$. After washing with water, the solution was dried with $Na_2SO_4$ and concentrated. Ether was added to the resulting residue to separate out a precipitate, which was collected by filtration.

Yield: 1 91 g (98 2%), Melting point: 172°–174° C., $Rf_1$: 0.37, $Rf_2$: 0.69 $[\alpha]_D^{28}$ +28.8° (c=0.68, in DMF)

Elemental analysis: As $C_{62}H_{77}N_7O_{14}$ Calculated: C, 65.08; H, 6.78; N, 8.57 Found: C, 64.84; H, 6.83; N, 8.80

(5) Production of Boc-D-Trp-D-Asp(OBzl)-Ala-Glu(BOzl)-D-Leu-Leu-OH

Boc-D-Trp-D-Asp(OBzl)-Ala-Glu(BOzl)-D-Leu-Leu-OPac (1.49 g) was dissolved in 90% aqueous AcOH (20 ml), and Zn powder (4.26 g) was added thereto, followed by stirring for hours. The Zn powder was separated by filtration, and the filtrate was concentrated. AcOEt was added to the residue to dissolve it, and the solution was washed with aqueous citric acid. After washing with water, the solution was dried with $Na_2SO_4$ and concentrated. Ether was added to the resulting residue to separate out a precipitate, which was collected by filtration.

Yield: 1.30 g (97.5%), Melting point: 192°–194° C., $Rf_1$: 0.12, $Rf_2$: 0.66 $[\alpha]_D^{28}$ +37.7° (c=0.92, in DMF)

Elemental analysis: As $C_{54}H_{71}N_7O_{13}$ Calculated: C, 63.20; H, 6.97; N, 9.55 Found: C, 63.02; H, 6.96; N, 9.63

(6) Production of cyclo[-D-Asp-Ala-Glu-D-Leu-Leu-D-Trp-]

Boc-D-Trp-D-Asp(OBzl)-Ala-Glu(BOzl)-D-Leu-Leu-OH (0.51 g) was dissolved in DCM (20 ml), and the solution was cooled with ice. HONB (0.18 g) and DCC (0.21 g) were added thereto, followed by stirring for 3 hours: Then, the resulting DCU was separated by filtration, followed by concentration, and ether was added to the residue to separate out a precipitate, which was collected by filtration. Ethanedithiol (0.09 ml) and 8N-HCl/dioxane (20 ml) were added thereto under ice cooling to dissolve the precipitate. The resulting solution was stirred for 10 minutes and concentrated. Then, ether was added to the residue to separate out a precipitate, which was collected by filtration and dried. The precipitate was dissolved in DMF (10 ml), and the resulting solution was added dropwise to DMF (90 ml) containing TEA (0.7 ml) for 30 minutes, followed by stirring overnight and concentration. Acetonitrile was added to the resulting residue to separate out a precipitate, which was collected by filtration and dried. Of this precipitate, 91 mg was dissolved in DMF (15 ml) and catalytically reduced in a stream of hydrogen using palladium black as a catalyst. The catalyst was separated by filtration, and the filtrate was concentrated. The resulting residue was dissolved in a small amount of AcOH, and then, water was added thereto to conduct lyophilization. Finally, the lyophilized product was purified by liquid chromatography using a YMC-D-ODS-5 column (2 cm×25 cm) (Y.M.C.) to obtain a desired material. The yield was 17.7 mg (24.1%).

Anal. for amino acids [6N-HCl, 110° C., hydrolysis for 24 hours; figures in parentheses show theoretical values.]: Asp 1.00(1); Glu 1.04(1); Ala 1.05 (1); Leu 2.07(2) LSIMS ($M+H^+$)=728, (theoretical value)=728

EXAMPLE 4

Production of cyclo[-D-Asp-Ala-D-Glu-D-Leu-Leu-D-Trp-]

(1) Production of Boc-D-Glu(OBzl)-D-Leu-Leu-OPac

TFA (20 ml) was added to Boc-D-Leu-Leu-OPac (1.85 g) prepared in example 1 (2) to dissolve it, followed by concentration. 4% aqueous $NaHCO_3$ was added thereto to adjust the pH to 9–10, and then, extraction was conducted using AcOEt. The extract was dried with $Na_2SO_4$ and concentrated. The resulting product was dissolved in DMF (15 ml) and cooled with ice. Then, TEA (0.56 ml) was added thereto. Boc-D-Glu(OBzl)-ONB [prepared from Boc-D-Glu(OBzl)-OH (1.48 g), HONB (0.86 g) and DCC (0.99 g)] was added thereto, followed by stirring overnight. The resulting insoluble material was separated by filtration, followed by concentration. The residue was dissolved in AcOEt, and the solution was washed with water, 10% aqueous citric acid and 4% aqueous $NaHCO_3$. After washing with water, the solution was dried with $Na_2SO_4$ and concentrated. Ether was added to the resulting residue to separate out a precipitate, which was collected by filtration.

Yield: 2.21 g (81.0%), Melting point: 136°–137° C., $Rf_1$: 0.40, $Rf_2$: 0.68 $[\alpha]_D^{28}$ −3.33° (c=1.02, in DMF)

Elemental analysis: As $C_{37}H_{51}N_3O_9$ Calculated: C, 65.18; H, 7.54; N, 6.16 Found: C, 65.23; H, 7.65; N, 6.10

(2) Production of Boc-Ala-D-Glu(OBzl)-D-Leu-Leu-OPac

TFA (20 ml) was added to Boc-D-Glu(OBzl)-D-Leu-Leu-OPac (1.91 g) to dissolve it, followed by concentration. 8N-HCl/dioxane (0.88 ml) was added thereto, and ether was added to precipitate crystals. The crystals were separated by filtration and dried. The resulting product was dissolved in DMF (15 ml) and cooled with ice. Then, TEA (0.90 ml) was added thereto. Boc-Ala-ONB [prepared from Boc-Ala-OH (0.53 g), HONB (0.55 g) and DCC (0.64 g)] was added thereto, followed by stirring overnight. The resulting insoluble material was separated by filtration, followed by concentration. The residue was dissolved in AcOEt, and the solution was washed with water, 10% aqueous citric acid and 4% aqueous $NaHCO_3$. After washing with water, the solution was dried with $Na_2SO_4$ and concentrated. Ether was added to the resulting residue to separate out a precipitate, which was collected by filtration.

Yield: 1.92 g (91.1%), Melting point: 187°–188° C., $Rf_1$: 0.36, $Rf_2$: 0.68 $[\alpha]_D^{28}$ −15.2° (c=0.94, in DMF)

Elemental analysis: As $C_{40}H_{56}N_4O_{10}$ Calculated: C, 63.81; H, 7.50; N, 7.44 Found: C, 63.91; H, 7.59; N, 7.74

(3) Production of Boc-D-Asp(OBzl)-Ala-D-Glu(BOzl)-D-Leu-Leu-OPac

TFA (20 ml) was added to Boc-Ala-D-Glu(OBzl)-D-Leu-Leu-OPac (1.81 g) to dissolve it, followed by concentration. 8N-HCl/dioxane (0.75 ml) was added thereto, and ether was added to precipitate crystals. The crystals were separated by filtration and dried. The resulting product was dissolved in DMF (15 ml) and cooled with ice. Then, TEA (0.67 ml) was added thereto. Boc-D-Asp(OBzl)-ONB [prepared from Boc-D-Asp(OBzl)-OH (0.85 g), HONB (0.51 g) and DCC (0.60 g)] was added thereto, followed by stirring overnight. The resulting insoluble material was separated by filtration, followed by concentration. The residue was dissolved in AcOEt, and the solution was washed with water, 10% aqueous citric acid and 4% aqueous $NaHCO_3$. After washing with water, the solution was dried with $Na_2SO_4$ and concentrated. Ether was added to the resulting residue to separate out a precipitate, which was collected by filtration.

Yield: 1.83 g (79.6%), Melting point: 116°–117° C., $Rf_1$: 0.35, $Rf_2$: 0.69 $[\alpha]_D^{28}$ +17.40 (c=0.80, in DMF)

Elemental analysis: As $C_{51}H_{67}N_5O_{13}$ Calculated: C, 63.93; H, 7.05; N, 7.31 Found: C, 63.77; H, 7.01; N, 7.44

(4) Production of Boc-D-Trp-D-Asp(OBzl)-Ala-D-Glu-(OBzl)-D-Leu-Leu-OPac

TFA (20 ml) was added to Boc-D-Asp(OBzl)-Ala-D-Glu(OBzl)-D-Leu-Leu-OPac (1.63 g) to dissolve it, followed by concentration. 8N-HCl/dioxane (0.53 ml) was added thereto, and ether was added to precipitate crystals. The crystals were separated by filtration and dried. The resulting product was dissolved in DMF (15 ml) and cooled with ice. Then, TEA (0.48 ml) was added thereto. Boc-D-Trp-ONB [prepared from Boc-D-Trp-OH (0.57 g), HONB (0.37 g) and DCC (0.42 g)] was added thereto, followed by stirring overnight. The resulting insoluble material was separated by filtration, followed by concentration. The residue was dissolved in AcOEt, and the solution was washed with water, 10% aqueous citric acid and 4% aqueous $NaHCO_3$. After washing with water, the solution was dried with $Na_2SO_4$ and concentrated. Ether was added to the resulting residue to separate out a precipitate, which was collected by filtration.

Yield: 1.64 g (84.3%), Melting point: 149°–150° C., $Rf_1$: 0.38, $Rf_2$: 0.70 $[\alpha]_D^{28}$ +24.2° (c=0.66, in DMF)

Elemental analysis: As $C_{62}H_{77}N_7O_{14}$ Calculated: C, 65.08; H, 6.78; N, 8.57 Found: C, 64.91; H, 6.86; N, 8.67

(5) Production of Boc-D-Trp-D-Asp(OBzl)-Ala-D-Glu(BOzl)-D-Leu-Leu-OH

Boc-D-Trp-D-Asp(OBzl)-Ala-D-Glu(BOzl)-D-Leu-Leu-OPac (1.49 g) was dissolved in 90% aqueous AcOH (20 ml), and Zn powder (4.26 g) was added thereto, followed by stirring for 3 hours. The Zn powder was separated by filtration, and the filtrate was concentrated. AcOEt was added to the residue to dissolve it, and the solution was washed with 10% aqueous citric acid. After washing with water, the solution was dried with $Na_2SO_4$ and concentrated. Ether was added to the resulting residue to separate out a precipitate, which was collected by filtration.

Yield: 1.24 g (93.0%), Melting point: 147°–149° C., $Rf_1$: 0.18, $Rf_2$: 0.67 $[\alpha]_D^{28}$ +44.1° (c=0.86, in DMF)

Elemental analysis: As $C_{54}H_{71}N_7O_{13}$ Calculated: C, 63.20; H, 6.97; N, 9.55 Found: C, 62.90; H, 7.10; N, 9.48

(6) Production of cyclo[-D-Asp-Ala-D-Glu-D-Leu-Leu-D-Trp-]

Boc-D-Trp-D-Asp(OBzl)-Ala-D-Glu(BOzl)-D-Leu-Leu-OH (0.51 g) was dissolved in DCM (20 ml), and the solution was cooled with ice. HONB (0.18 g) and DCC (0.21 g) were added thereto, followed by stirring for 3 hours. Then, the resulting DCU was separated by filtration, followed by concentration, and ether was added to the residue to separate out a precipitate, which was collected by filtration. Ethanedithiol (0.09 ml) and 8-N HCl/dioxane (20 ml) were added thereto under ice cooling to dissolve the precipitate. The resulting solution was stirred for 10 minutes and concentrated. Then, ether was added to the residue to separate out a precipitate, which was collected by filtration and dried. The precipitate was dissolved in DMF (10 ml), and the resulting solution was added dropwise to DMF (90 ml) containing TEA (0.7 ml) for 30 minutes, followed by stirring overnight and concentration. Acetonitrile was added to the resulting residue to separate out a precipitate, which was collected by filtration and dried. Of this precipitate, 91 mg was dissolved in DMF (15 ml) and catalytically reduced in a stream of hydrogen using palladium black as a catalyst. The catalyst was separated by filtration, and the filtrate was concentrated. The resulting residue was dissolved in a small amount of AcOH, and then, water was added thereto to conduct lyophilization. Finally, the lyophilized product was purified by liquid chromatography using a YMC-D-ODS-5 column (2 cm×25 cm) (Y.M.C.) to obtain a desired material. The yield was 14.3 mg (10.8%).

Anal. for amino acids [6N-HCl, 110° C., hydrolysis for 24 hours; figures in parentheses show theoretical values.]: Asp 1.00(1); Glu 1.04(1); Ala 1.05(1); Leu 2.09(2) LSIMS $(M+H^+)$=728, (theoretical value)=728

EXAMPLE 5

Production of cyclo[-D-Asp-Gly-Ala-D-Leu-Leu-D-Trp-]

(1) Production of Boc-Ala-D-Leu-Leu-OPac

TFA (20 ml) was added to Boc-D-Leu-Leu-OPac (6.50 g) prepared in example 1 (2) to dissolve it, followed by concentration. 4% aqueous $NaHCO_3$ was added thereto to adjust the pH to 9–10, and then, extraction was conducted using AcOEt. The extract was dried with $Na_2SO_4$ and concentrated. The resulting product was dissolved in DMF (15 ml) and cooled with ice. Then, TEA (2.07 ml) was added thereto. Boc-Ala-ONB [prepared from Boc-Ala-OH (2.67 g), HONB (2.65 g) and DCC (3.05 g)] was added thereto, followed by stirring overnight. The resulting insoluble material was separated by filtration, followed by concentration. The residue was dissolved in AcOEt, and the solution was washed with water, 10% aqueous citric acid and 4% aqueous $NaHCO_3$. After washing with water, the solution was dried with $Na_2SO_4$ and concentrated. Ether was added to the resulting residue to separate out a precipitate, which was collected by filtration.

Yield: 6 70 g (90 0%), Melting point: 121.0°–122.0° C., $Rf_1$: 0.56, $Rf_2$: 0.71 $[\alpha]_D^{25}$ −12.0° (c=1.01, in DMF)

Elemental analysis: As $C_{28}H_{43}N_3O_7$ Calculated: C, 63.02; H, 8.12; N, 7.87 Found: C, 63.07; H, 7.90; N, 7.92

(2) Production of Boc-Gly-Ala-D-Leu-Leu-OPac

TFA (20 ml) was added to Boc-Ala-D-Leu-Leu-OPac (2.20 g) to dissolve it, followed by concentration. 8N-HCl/dioxane (1.00 ml) was added thereto, and ether was added to precipitate crystals. The crystals were separated by filtration and dried. The resulting product was dissolved in DMF (15 ml) and cooled with ice. Then, TEA (0.61 ml) was added thereto. Boc-Gly-ONB [prepared from Boc-Gly-OH (0.72 g), HONB (0.78 g) and DCC (0.89 g)] was added thereto, followed by stirring overnight. The resulting insoluble material was separated by filtration, followed by concentration.

The residue was dissolved in AcOEt, and the solution was washed with water, 10% aqueous citric acid and 4% aqueous NaHCO₃. After washing with water, the solution was dried with Na₂SO₄ and concentrated. Ether was added to the resulting residue to separate out a precipitate, which was collected by filtration.

Yield: 2 26 g (93 2%), Melting point: 158.5°–160.0° C., Rf₁: 0.30, Rf₂: 0.54 $[\alpha]_D^{25}$ −4.8° (c=1.02, in DMF)

Elemental analysis: As $C_{30}H_{46}N_4O_8$ Calculated: C, 61.00; H, 7.85; N, 9.48 Found: C, 60.92; H, 7.91; N, 9.66

(3) Production of Boc-D-Asp(OBzl)-Gly-Ala-D-Leu-Leu-OPac

TFA (20 ml) was added to Boc-Gly-Ala-D-Leu-Leu-OPac (2.23 g) to dissolve it, followed by concentration. 8-N HCl/dioxane (1.00 ml) was added thereto, and ether was added to precipitate crystals. The crystals were separated by filtration and dried. The resulting product was dissolved in DMF (15 ml) and cooled with ice. Then, TEA (0.55 ml) was added thereto. Boc-D-Asp(OBzl)-ONB [prepared from Boc-D-Asp(OBzl)-OH (1.22 g), HONB (0.71 g) and DCC (0.82 g)] was added thereto, followed by stirring overnight. The resulting insoluble material was separated by filtration, followed by concentration. The residue was dissolved in AcOEt, and the solution was washed with water, 10% aqueous citric acid and 4% aqueous NaHCO₃. After washing with water, the solution was dried with Na₂SO₄ and concentrated. Ether was added to the resulting residue to separate out a precipitate, which was collected by filtration.

Yield: 2.62 g (87.3%), Melting point: 68.0°–69.5° C., Rf₁: 0.25, Rf₂: 0.53 $[\alpha]_D^{25}$ +5.4° (c=1.03, in DMF)

Elemental analysis: As $C_{41}H_{57}N_5O_{11}$ Calculated: C, 61.87; H, 7.22; N, 8.80 Found: C, 61.78; H, 7.34; N, 8.62

(4) Production of Boc-D-Trp-D-Asp(OBzl)-Gly-Ala-D-Leu-Leu-OPac

TFA (20 ml) was added to Boc-D-Asp(OBzl)-Gly-Ala-D-Leu-Leu-OPac (2.51 g) to dissolve it, followed by concentration. 8N-HCl/dioxane (1.00 ml) was added thereto, and ether was added to precipitate crystals. The crystals were separated by filtration and dried. The resulting product was dissolved in DMF (15 ml) and cooled with ice. Then, TEA (0.46 ml) was added thereto. Boc-D-Trp-ONB [prepared from Boc-D-Trp-OH (0.96 g), HONB (0.59 g) and DCC (0.68 g)] was added thereto, followed by stirring overnight. The resulting insoluble material was separated by filtration, followed by concentration. The residue was dissolved in AcOEt, and the solution was washed with water, 10% aqueous citric acid and 4% aqueous NaHCO₃. After washing with water, the solution was dried with Na₂SO₄ and concentrated. Ether was added to the resulting residue to separate out a precipitate, which was collected by filtration.

Yield: 1.52 g (49.1%), Melting point: 109.5°–110.0° C., Rf₁: 0.27, Rf₂: 0.54 $[\alpha]_D^{25}$ +9.0° (c=1.04, in DMF)

Elemental analysis: As $C_{52}H_{67}N_7O_{12}$ Calculated: C, 63.59; H, 6.88; N, 9.98 Found: C, 63.72; H, 6.96; N, 10.17

(5) Production of Boc-D-Trp-D-Asp(OBzl)-Gly-Ala-D-Leu-Leu-OH

Boc-D-Trp-D-Asp(OBzl)-Gly-Ala-D-Leu-Leu-OPac (0.50 g) was dissolved in 90% aqueous AcOH (20 ml), and Zn powder (1.66 g) was added thereto, followed by stirring for 3 hours. The Zn powder was separated by filtration, and the filtrate was concentrated. AcOEt was added to the residue to dissolve it, and the solution was washed with 10% aqueous citric acid. After washing with water, the solution was dried with Na₂SO₄ and concentrated. Ether was added to the resulting residue to separate out a precipitate, which was collected by filtration.

Yield: 385 mg (87 5%), Melting point: 120.0°–122.0° C., Rf₁: 0.02, Rf₂: 0.40 $[\alpha]_D^{25}$ +23.0° (c=1.01, in DMF)

Elemental analysis: As $C_{44}H_{61}N_7O_{11}$ Calculated: C, 61.17; H, 7.12; N, 11.35 Found: C, 61.28; H, 7.08; N, 11.11

(6) Production of cyclo[-D-Asp-Gly-Ala-D-Leu-Leu-D-Trp-]

Boc-D-Trp-D/Asp(OBzl)-Gly-Ala-D-Leu-Leu-OH (0.51 g) was dissolved in acetonitrile (20 ml), and the solution was cooled with ice. HONB (0.18 g) and DCC (0.21 g) were added thereto, followed by stirring for 3 hours. Then, the resulting DCU was separated by filtration, followed by concentration, and ether was added to the residue to separate out a precipitate, which was collected by filtration. Ethanedithiol (0.09 ml) and 8N-HCl/dioxane (20 ml) were added thereto under ice cooling to dissolve the precipitate. The resulting solution was stirred for 10 minutes and concentrated. Then, ether was added to the residue to separate out a precipitate, which was collected by filtration and dried. The precipitate was dissolved in DMF (10 ml), and the resulting solution was added dropwise to DMF (90 ml) containing TEA (0.7 ml) for 30 minutes, followed by stirring overnight and concentration. Acetonitrile was added to the resulting residue to separate out a precipitate, which was collected by filtration and dried. Of this precipitate, 51 mg was dissolved in DMF (15 ml) and catalytically reduced in a stream of hydrogen using palladium black as a catalyst. The catalyst was separated by filtration, and the filtrate was concentrated. The resulting residue was dissolved in a small amount of AcOH, and then, water was added thereto to conduct lyophilization. Finally, the lyophilized product was purified by liquid chromatography using a YMC-D-ODS-5 column (2 cm×25 cm) (Y.M.C.) to obtain a desired material. The yield was 28.5 mg (19.2%).

Anal. for amino acids [6-N HCl, 110° C., hydrolysis for 24 hours; figures in parentheses show theoretical values.]: Asp 1.00(1); Gly 1.03(1); Ala 1.04(1); Leu 2.09(2) LSIMS (M+H⁺)=656, (theoretical value)=656

EXAMPLE 6

Production of cyclo[-D-Asp-Asp-Ala-D-Leu-Leu-D-Trp-]

(1) Production of Boc-Asp(OBzl)-Ala-D-Leu-Leu-OPac

TFA (20 ml) was added to Boc-Ala-D-Leu-Leu-OPac (2.20 g) prepared in example 5 (1) to dissolve it, followed by concentration. 8N-HCl/dioxane (1.00 ml) was added thereto, and ether was added to precipitate crystals. The crystals were separated by filtration and dried. The resulting product was dissolved in DMF (15 ml) and cooled with ice. Then, TEA (0.61 ml) was added thereto. Boc-Asp(OBzl)-ONB [prepared from Boc-Asp(OBzl)-OH (1.33 g), HONB (0.78 g) and DCC (0.89 g)] was added thereto, followed by stirring overnight. The resulting insoluble material was separated by filtration, followed by concentration. The residue was dissolved in AcOEt, and the solution was washed with water, 10% aqueous citric acid and 4% aqueous NaHCO₃. After washing with water, the solution was dried with Na₂SO₄ and concentrated. Ether was added to the resulting residue to separate out a precipitate, which was collected by filtration.

Yield: 2.87 g (94.2%), Melting point: 149.5°–150.5° C., Rf₁: 0.58, Rf₂: 0.68 $[\alpha]_D^{25}$ −15.2° (c=1.02, in DMF)

Elemental analysis: As $C_{39}H_{54}N_4O_{10}$ Calculated: C, 63.40; H, 7.37; N, 7.58 Found: C, 63.55; H, 7.42; N, 7.68

(2) Production of Boc-D-Asp(OBzl)-Asp(OBzl)-Ala-D-Leu-Leu-OPac

TFA (20 ml) was added to Boc-Asp(OBzl)-Ala-D-Leu-Leu-OPac (2.77 g) to dissolve it, followed by concentration. 8N-HCl/dioxane (1.00 ml) was added thereto, and ether was added to precipitate crystals. The crystals were separated by filtration and dried. The resulting product was dissolved in DMF (15 ml) and cooled with ice. Then, TEA (0.55 ml) was added thereto. Boc-D-Asp(OBzl)-ONB [prepared from Boc-D-Asp(OBzl)-OH (1.21 g), HONB (0.71 g) and DCC (0.81 g)] was added thereto, followed by stirring overnight. The resulting insoluble material was separated by filtration, followed by concentration. The residue was dissolved in AcOEt, and the solution was washed with water, 10% aqueous citric acid and 4% aqueous $NaHCO_3$. After washing with water, the solution was dried with $Na_2SO_4$ and concentrated. Ether was added to the resulting residue to separate out a precipitate, which was collected by filtration.

Yield: 3.08 g (87.0%), Melting point: 72.0°–74.0° C., $Rf_1$: 0.56, $Rf_2$: 0.64 $[\alpha]_D^{25}$ −7.0° (c=1.02, in DMF)

Elemental analysis: As $C_{50}H_{65}N_5O_{13}$ Calculated: C, 63.61; H, 6.94; N, 7.42 Found: C, 63.38; H, 6.88; N, 7.42

(3) Production of Boc-D-Trp-D-Asp(OBzl)-Ala-D-Leu-Leu-OPac

TFA (20 ml) was added to Boc-D-Asp(OBzl)-Asp(OBzl)-Ala-D-Leu-Leu-OPac (2.94 g) to dissolve it, followed by concentration. 8N-HCl/dioxane (1.00 ml) was added thereto, and ether was added to precipitate crystals. The crystals were separated by filtration and dried. The resulting product was dissolved in DMF (15 ml) and cooled with ice. Then, TEA (0.46 ml) was added thereto. Boc-D-Trp-ONB [prepared from Boc-D-Trp-OH (0.96 g), HONB (0.59 g) and DCC (0.68 g)] was added thereto, followed by stirring overnight. The resulting insoluble material was separated by filtration, followed by concentration. The residue was dissolved in AcOEt, and the solution was washed with water, 10% aqueous citric acid and 4% aqueous $NaHCO_3$. After washing with water, the solution was dried with $Na_2SO_4$ and concentrated. Ether was added to the resulting residue to separate out a precipitate, which was collected by filtration.

Yield: 2.61 g (77.0%), Melting point: 190.0°–192.5° C., $Rf_1$: 0.49, $Rf_2$: 0.60 $[\alpha]_D^{25}$ +4.9° (c=1.03, in DMF)

Elemental analysis: As $C_{61}H_{75}N_7O_{14}$ Calculated: C, 64.82; H, 6.69; N, 8.67 Found: C, 65.01; H, 6.78; N, 8.87

(4) Production of Boc-D-Trp-D-Asp(OBzl)-Asp(OBzl)-Ala-D-Leu-Leu-OH

Boc-D-Trp-D-Asp(OBzl)-Asp(OBzl)-Ala-D-Leu-Leu-OPac (0.50 g) was dissolved in 90% aqueous AcOH (20 ml), and Zn powder (1.66 g) was added thereto, followed by stirring for 3 hours. The Zn powder was separated by filtration, and the filtrate was concentrated. AcOEt was added to the residue to dissolve it, and the solution was washed with 10% aqueous citric acid. After washing with water, the solution was dried with $Na_2SO_4$ and concentrated. Ether was added to the resulting residue to separate out a precipitate, which was collected by filtration.

Yield: 363 mg (81.0%), Melting point: 174.0°–175.0° C., $Rf_1$: 0.04, $Rf_2$: 0.50 $[\alpha]_D^{25}$ +12.1° (c=1.03, in DMF)

Elemental analysis: As $C_{53}H_{69}N_7O_{13}$ Calculated: C, 62.89; H, 6.87; N, 9.69 Found: C, 62.92; H, 6.89; N, 9.78

(5) Production of cyclo[-D-Asp-Asp-Ala-D-Leu-Leu-D-Trp-]

Boc-D-Trp-D-Asp(OBzl)-Asp(OBzl)-Ala-D-Leu-Leu-OH (0.51 g) was dissolved in acetonitrile (20 ml), and the solution was cooled with ice. HONB (0.16 g) and DCC (0.18 g) were added thereto, followed by stirring for 3 hours. Then, the resulting DCU was separated by filtration, followed by concentration, and ether was added to the residue to separate out a precipitate, which was collected by filtration. Ethanedithiol (0.09 ml) and 8N-HCl/dioxane (20 ml) were added thereto under ice cooling to dissolve the precipitate. The resulting solution was stirred for 10 minutes and concentrated. Then, ether was added to the residue to separate out a precipitate, which was collected by filtration and dried. The precipitate was dissolved in DMF (10 ml), and the resulting solution was added dropwise to DMF (90 ml) containing TEA (0.62 ml) for 30 minutes, followed by stirring overnight and concentration. Acetonitrile was added to the resulting residue to separate out a precipitate, which was collected by filtration and dried. Of this precipitate, 51 mg was dissolved in DMF (15 ml) and catalytically reduced in a stream of hydrogen using palladium black as a catalyst. The catalyst was separated by filtration, and the filtrate was concentrated. The resulting residue was dissolved in a small amount of AcOH, and then, water was added thereto to conduct lyophilization. Finally, the lyophilized product was purified by liquid chromatography using a YMC-D-ODS-5 column (2 cm×25 cm) (Y.M.C.) to obtain a desired material. The yield was 28.5 mg (17.8%).

Anal for amino acids [6N-HCl, 110° C., hydrolysis for 24 hours; figures in parentheses show theoretical values.]: Asp 2.00(2); Ala 1.04(1); Leu 2.10(2) LSIMS $(M+H^+)$=714, (theoretical value)=714

EXAMPLE 7

Production of cyclo[-D-Asp-Glu-Ala-D-Leu-Leu-D-Trp-]

(1) Production of Boc-Glu(OBzl)-Ala-D-Leu-Leu-OPac

TFA (20 ml) was added to Boc-Ala-D-Leu-Leu-OPac (2.20 g) prepared in example 5 (1) to dissolve it, followed by concentration. 8N-HCl/dioxane (1.00 ml) was added thereto, and ether was added to precipitate crystals. The crystals were separated by filtration and dried. The resulting product was dissolved in DMF (15 ml) and cooled with ice. Then, TEA (0.61 ml) was added thereto. Boc-Glu(OBzl)-ONB [prepared from Boc-Glu(OBzl)-OH (1.39 g), HONB (0.78 g) and DCC (0.89 g)] was added thereto, followed by stirring overnight. The resulting insoluble material was separated by filtration, followed by concentration. The residue was dissolved in AcOEt, and the solution was washed with water, 10% aqueous citric acid and 4% aqueous $NaHCO_3$. After washing with water, the solution was dried with $Na_2SO_4$ and concentrated. Ether was added to the resulting residue to separate out a precipitate, which was collected by filtration.

Yield: 2.86 g (92.4%), Melting point: 152.5°–153.5° C., $Rf_1$: 0.36, $Rf_2$: 0.67 $[\alpha]_D^{25}$ +0.8° (c=1.04, in DMF)

Elemental analysis: As $C_{40}H_{56}N_4O_{10}$ Calculated: C, 63.81; H, 7.50; N, 7.44 Found: C, 63.86; H, 7.53; N, 7.65

(2) Production of Boc-D-Asp(OBzl)-Glu(OBzl)-Ala-D-Leu-Leu-OPac

TFA (20 ml) was added to Boc-Glu(OBzl)-Ala-D-Leu-Leu-OPac (2.76 g) to dissolve it, followed by concentration. 8N-HCl/dioxane (1.00 ml) was added thereto, and ether was added to precipitate crystals. The crystals were separated by filtration and dried. The resulting product was dissolved in DMF (15 ml) and cooled with ice. Then, TEA (0.54 ml) was added thereto. Boc-D-Asp(OBzl)-ONB [prepared from Boc-D-Asp(OBzl)-OH (1.19 g), HONB (0.69 g) and DCC (0.80 g)] was added thereto, followed by stirring overnight. The resulting insoluble material was separated by filtration, followed by concentration. The residue was dissolved in AcOEt, and the solution was washed with water, 10% aqueous citric acid and 4% aqueous $NaHCO_3$. After washing with water, the solution was dried with $Na_2SO_4$ and concentrated. Ether was added to the resulting residue to separate out a precipitate, which was collected by filtration.

Yield: 3.08 g (87.6%), Melting point: 127.0°–127.5° C., $Rf_1$: 0.51, $Rf_2$: 0.60 $[\alpha]_D^{25}$ +4.5° (c=1.01, in DMF)

Elemental analysis: As $C_{51}H_{67}N_5O_{13}$ Calculated: C, 63.93; H, 7.05; N, 7.31 Found: C, 64.05; H, 7.08; N, 7.42

(3) Production of Boc-D-Trp-D-Asp(OBzl)-Glu(OBzl)-Ala-D-Leu-Leu-OPac

TFA (20 ml) was added to Boc-D-Asp(OBzl)-Glu(OBzl)-Ala-D-Leu-Leu-OPac (2.95 g) to dissolve it, followed by concentration. 8N-HCl/dioxane (1.00 ml) was added thereto, and ether was added to precipitate crystals. The crystals were separated by filtration and dried. The resulting product was dissolved in DMF (15 ml) and cooled with ice. Then, TEA (0.46 ml) was added thereto. Boc-D-Trp-ONB [prepared from Boc-D-Trp-OH (0.94 g), HONB (0.58 g) and DCC (0.67 g)] was added thereto, followed by stirring overnight. The resulting insoluble material was separated by filtration, followed by concentration. The residue was dissolved in AcOEt, and the solution was washed with water, 10% aqueous citric acid and 4% aqueous $NaHCO_3$. After washing with water, the solution was dried with $Na_2SO_4$ and concentrated. Ether was added to the resulting residue to separate out a precipitate, which was collected by filtration.

Yield: 2.59 g (75.4%), Melting point: 182.0°–183.5° C., $Rf_1$: 0.51, $Rf_2$: 0.62 $[\alpha]_D^{25}$ +12.1° (c=1.03, in DMF)

Elemental analysis: As $C_{62}H_{77}N_7O_{14}$ Calculated: C, 65.08; H, 6.78; N, 8.57 Found: C, 65.11; H, 6.76; N, 8.76

(4) Production of Boc-D-Trp-D-Asp(OBzl)-Glu(OBzl)-Ala-D-Leu-Leu-OH

Boc-D-Trp-D-Asp(OBzl)-Glu(OBzl)-Ala-D-Leu-Leu-OPac (0.50 g) was dissolved in 90% aqueous AcOH (20 ml), and Zn powder (1.66 g) was added thereto, followed by stirring for 3 hours. The Zn powder was separated by filtration, and the filtrate was concentrated. AcOEt was added to the residue to dissolve it, and the solution was washed with 10% aqueous citric acid. After washing with water, the solution was dried with $Na_2SO_4$ and concentrated. Ether was added to the resulting residue to separate out a precipitate, which was collected by filtration.

Yield: 410 mg (91.4%), Melting point: 179.5°–180.5° C., $Rf_1$: 0.03, $Rf_2$: 0.53 $[\alpha]_D^{25}$ +16.1° (c=1.02, in DMF)

Elemental analysis: As $C_{54}H_{71}N_7O_{13}$ Calculated: C, 63.20; H, 6.97; N, 9.55 Found: C, 63.45; H, 7.00; N, 9.67

(5) Production of cyclo[-D-Asp-Glu-Ala-D-Leu-Leu-D-Trp-]

Boc-D-Trp-D-Asp(OBzl)-Glu(OBzl)-Ala-D-Leu-Leu-OH (0.51 g) was dissolved in acetonitrile (20 ml), and the solution was cooled with ice. HONB (0.16 g) and DCC (0.18 g) were added thereto, followed by stirring for 3 hours. Then, the resulting DCU was separated by filtration, followed by concentration, and ether was added to the residue to separate out a precipitate, which was collected by filtration. Ethanedithiol (0.09 ml) and 8N-HCl/dioxane (20 ml) were added thereto under ice cooling to dissolve the precipitate. The resulting solution was stirred for 10 minutes and concentrated. Then, ether was added to the residue to separate out a precipitate, which was collected by filtration and dried. The precipitate was dissolved in DMF (10 ml), and the resulting solution was added dropwise to DMF (90 ml) containing TEA (0.62 ml) for 30 minutes, followed by stirring overnight and concentration. Acetonitrile was added to the resulting residue to separate out a precipitate, which was collected by filtration and dried. Of this precipitate, 51 mg was dissolved in DMF (15 ml) and catalytically reduced in a stream of hydrogen using palladium black as a catalyst. The catalyst was separated by filtration, and the filtrate was concentrated. The resulting residue was dissolved in a small amount of AcOH, and then, water was added thereto to conduct lyophilization. Finally, the lyophilized product was purified by liquid chromatography using a YMC-D-ODS-5 column (2 cm×25 cm) (Y.M.C.) to obtain a desired material. The yield was 28.5 mg (20.6%).

Anal. for amino acids [6N-HCl, 110° C., hydrolysis for 24 hours; figures in parentheses show theoretical values.]: Asp 1.00(1); Glu 1.02(1); Ala 1.05(1); Leu 2.06(2) LSIMS $(M+H^+)$=728, (theoretical value)=728

EXAMPLE 8

Production of cyclo[-D-Asp-Trp-Asp-D-Leu-Leu-D-Trp-]

(1) Production of Boc-Trp-Asp(OBzl)-D-Leu-Leu-OPac

Boc-Asp(OBzl)-D-Leu-Leu-OPac (2.14 g) prepared in example 1 (3) was dissolved in 8-N HCl/dioxane (10 ml), and the solution was stirred under ice cooling for 10 minutes, followed by concentration. Then, ether was added to precipitate crystals. The crystals were separated by filtration and dried. The resulting product was dissolved in DMF (15 ml) and cooled with ice. Then, TEA (0.90 ml) was added thereto. Boc-Trp-ONB [prepared from Boc-Trp-OH (1.17 g), HONB (0.69 g) and DCC (0.79 g)] was added thereto, followed by stirring overnight. The resulting insoluble material was separated by filtration, followed by concentration. The residue was dissolved in AcOEt, and the solution was washed with water, 10% aqueous citric acid and 4% aqueous $NaHCO_3$. After washing with water, the solution was dried with $Na_2SO_4$ and concentrated. Ether was added to the resulting residue to separate out a precipitate, which was collected by filtration.

Yield: 2.48 g (90.7%), Melting point: 143°–144° C., $Rf_1$: 0.43, $Rf_2$: 0.74 $[\alpha]_D^{28}$ −25.8° (c=0.98, in DMF)

Elemental analysis: As $C_{47}H_{59}N_5O_{10}$ Calculated: C, 66.10; H, 6.96; N, 8.20 Found: C, 66.22; H, 7.01; N, 8.49

(2) Production of Boc-D-Asp(OBzl)-Trp-Asp(OBzl)-D-Leu-Leu-OPac

Boc-Trp-Asp(OBzl)-D-Leu-Leu-OPac (2.31 g) was dissolved in 8N-HCl/dioxane (10 ml), and the solution was stirred under ice cooling for 10 minutes, followed by concentration. Then, ether was added to precipitate crystals. The crystals were separated by filtration and dried. The resulting product was dissolved in DMF (15 ml) and cooled with ice. Then, TEA (0.75 ml) was added thereto. Boc-D-Asp(OBzl)-ONB [prepared from Boc-D-Asp(OBzl)-OH (0.96 g), HONB (0.58 g) and DCC (0.67 g)] was added thereto, followed by stirring overnight. The resulting insoluble material was separated by filtration, followed by concentration. The residue was dissolved in AcOEt, and the solution was washed with water, 10% aqueous citric acid and 4% aqueous $NaHCO_3$. After washing with water, the solution was dried with $Na_2SO_4$ and concentrated. Ether was added to the resulting residue to separate out a precipitate, which was collected by filtration.

Yield: 2.48 g (86.7%), Melting point: 171°–172° C., $Rf_1$: 0.41, $Rf_2$: 0.72 $[\alpha]_D^{28}$ −16.0° (c=1.31, in DMF)

Elemental analysis: As $C_{58}H_{70}N_6O_{13}$ Calculated: C, 65.77; H, 6.66; N, 7.93 Found: C, 65.82; H, 6.91; N, 8.10

(3) Production of Boc-D-Trp-D-Asp(OBzl)-Trp-Asp(OBzl)-D-Leu-Leu-OPac

Boc-D-Asp(OBzl)-Trp-Asp(OBzl)-D-Leu-Leu-OPac (2.12 g) was dissolved in 8N-HCl/dioxane (10 ml), and the solution was stirred under ice cooling for 10 minutes, followed by concentration. Then, ether was added to precipitate crystals. The crystals were separated by filtration and dried. The resulting product was dissolved in DMF (15 ml) and cooled with ice. Then, TEA (0.56 ml) was added thereto. Boc-D-Trp-ONB [prepared from Boc-D-Trp-OH (0.67 g), HONB (0.43 g) and DCC (0.49 g)] was added thereto, followed by stirring overnight. The resulting insoluble material was separated by filtration, followed by concentration. The residue was dissolved in AcOEt, and the solution was washed with water, 10% aqueous citric acid and aqueous $NaHCO_3$. After washing with water, the solution was dried with $Na_2SO_4$ and concentrated. Ether was added to the resulting residue to separate out a precipitate, which was collected by filtration. Yield: 2.10 g (93.1%), Melting point: 180°–181° C., $Rf_1$: 0.33, $Rf_2$: 0.69 $[\alpha]_D^{28}$ −4.4° (c=1.11, in DMF)

Elemental analysis: As $C_{69}H_{80}N_8O_{14}$ Calculated: C, 66.54; H, 6.47; N, 9.00 Found: C, 66.45; H, 6.76; N, 9.10

(4) Production of Boc-D-Trp-D-Asp(OBzl)-Trp-Asp(OBzl)-D-Leu-Leu-OH

Boc-D-Trp-D-Asp(OBzl)-Trp-Asp(OBzl)-D-Leu-Leu-OPac (1.49 g) was dissolved in 90% aqueous AcOH (20 ml), and Zn powder (3.92 g) was added thereto, followed by stirring for 3 hours. The Zn powder was separated by filtration, and the filtrate was concentrated. AcOEt was added to the residue to dissolve it, and the solution was washed with aqueous citric acid. After washing with water, the solution was dried with $Na_2SO_4$ and concentrated. Ether was added to the resulting residue to separate out a precipitate, which was collected by filtration.

Yield: 1.30 g (96.1%), Melting point: 114°–115° C., $Rf_1$: 0.10, $Rf_2$: 0.65 $[\alpha]_D^{28}$ +1.6° (c=0.87, in DMF)

Elemental analysis: As $C_{61}H_{74}N_8O_{13}$ Calculated: C, 64.99; H, 6.62; N, 9.94 Found: C, 65.01; H, 6.88; N, 10.02

(5) Production of cyclo[-D-Asp-Trp-Asp-D-Leu-Leu-D-Trp-]

Boc-D-Trp-D-Asp(OBzl)-Trp-Asp(OBzl)-D-Leu-Leu-OH (0.56 g) was dissolved in DCM (20 ml), and the solution was cooled with ice. HONB (0.18 g) and DCC (0.21 g) were added thereto, followed by stirring for 3 hours. Then, the resulting DCU was separated by filtration, followed by concentration, and ether was added to the residue to separate out a precipitate, which was collected by filtration. 8N-HCl/dioxane (20 ml) was added thereto under ice cooling to dissolve the precipitate. The resulting solution was stirred for 10 minutes and concentrated. Then, ether was added to the residue to separate out a precipitate, which was collected by filtration and dried. The precipitate was dissolved in DMF (10 ml), and the resulting solution was added dropwise to DMF (90 ml) containing TEA (0.7 ml) for 30 minutes, followed by stirring overnight and concentration. Acetonitrile-ether was added to the resulting residue to separate out a precipitate, which was collected by filtration and dried. Of this precipitate, 101 mg was dissolved in DMF (15 ml) and catalytically reduced in a stream of hydrogen using palladium black as a catalyst. The catalyst was separated by filtration, and the filtrate was concentrated. The resulting residue was dissolved in a small amount of AcOH, and then, water was added thereto to conduct lyophilization. Finally, the lyophilized product was purified by liquid chromatography using a YMC-D-ODS-5 column (2 cm×25 cm) (Y.M.C.) to obtain a desired material. The yield was 12.4 mg (52.9%).

Anal. for amino acids [6N-HCl, 110° C., hydrolysis for 24 hours; figures in parentheses show theoretical values.]: Asp 2.00(2); Leu 2.15(2) LSIMS (M+H$^+$)=829, (theoretical value)=829

EXAMPLE 9

Production of cyclo[-D-Asp-Pro-Asp-D-Leu-Leu-D-Trp-]

(1) Production of Boc-Pro-Asp(OBzl)-D-Leu-Leu-OPac

Boc-Asp(OBzl)-D-Leu-Leu-OPac (2.14 g) prepared in example 1 (3) was dissolved in 8N-HCl/dioxane (10 ml), and the solution was stirred under ice cooling for 10 minutes, followed by concentration. Then, ether was added to precipitate crystals. The crystals were separated by filtration and dried. The resulting product was dissolved in DMF (15 ml) and cooled with ice. Then, TEA (0.90 ml) was added thereto. Boc-Pro-ONB [prepared from Boc-Pro-OH (0.76 g), HONB (0.69 g) and DCC (0.79 g)] was added thereto, followed by stirring overnight. The resulting insoluble material was separated by filtration, followed by concentration. The residue was dissolved in AcOEt, and the solution was washed with water, 10% aqueous citric acid and 4% aqueous $NaHCO_3$. After washing with water, the solution was dried with $Na_2SO_4$ and concentrated. Ether was added to the resulting residue to separate out a precipitate, which was collected by filtration.

Yield: 2.19 g (89.5%), Melting point: 135°–136° C., $Rf_1$: 0.44, $Rf_2$: 0.74 $[\alpha]_D^{28}$ −40.0° (c=1.02, in DMF)

Elemental analysis: As $C_{41}H_{56}N_4O_{10}$ Calculated: C, 64.38; H, 7.38; N, 7.32 Found: C, 64.40; H, 7.53; N, 7.37

(2) Production of Boc-D-Asp(OBzl)-Pro-Asp(OBzl)-D-Leu-Leu-OPac

Boc-Pro-Asp(OBzl)-D-Leu-Leu-OPac (2.07 g) was dissolved in 8N-HCl/dioxane (10 ml), and the solution was stirred under ice cooling for 10 minutes, followed by concentration. Then, ether was added to precipitate crystals. The crystals were separated by filtration and dried. The resulting product was dissolved in DMF (15 ml) and cooled with ice. Then, TEA (0.75 ml) was added thereto. Boc-D-Asp(OBzl)-ONB [prepared from Boc-D-Asp(OBzl)-OH (0.96 g), HONB (0.58 g) and DCC (0.67 g)] was added thereto, followed by stirring overnight. The resulting insoluble material was separated by filtration, followed by concentration. The residue was dissolved in AcOEt, and the solution was washed with water, 10% aqueous citric acid and 4% aqueous $NaHCO_3$. After washing with water, the solution was dried with $Na_2SO_4$ and concentrated. Ether was added to the resulting residue to separate out a precipitate, which was collected by filtration.

Yield: 2.39 g (91.2%), Melting point: 59°–61° C., $Rf_1$: 0.48, $Rf_2$: 0.74 $[\alpha]_D^{28}$ −14.3° (c=1.07, in DMF)

Elemental analysis: As $C_{52}H_{67}N_6O_{13}$ Calculated: C, 64.38; H, 6.96; N, 7.22 Found: C, 64.17; H, 7.18; N, 7.39

(3) Production of Boc-D-Trp-D-Asp(OBzl)-Pro-Asp(OBzl)-D-Leu-Leu-OPac

Boc-D-Asp(OBzl)-Pro-Asp(OBzl)-D-Leu-Leu-OPac (1.94 g) was dissolved in 8-N HCl/dioxane (10 ml), and the solution was stirred under ice cooling for 10 minutes, followed by concentration. Then, ether was added to precipitate crystals. The crystals were separated by filtration and dried. The resulting product was dissolved in DMF (15 ml) and cooled with ice. Then, TEA (0.56 ml) was added thereto. Boc-D-Trp-ONB [prepared from Boc-D-Trp-OH (0.67 g), HONB (0.43 g) and DCC (0.49 g)] was added thereto, followed by stirring overnight. The resulting insoluble material was separated by filtration, followed by concentration. The residue was dissolved in AcOEt, and the solution was washed with water, 10% aqueous citric acid and 4% aqueous $NaHCO_3$. After washing with water, the solution was dried with $Na_2SO_4$ and concentrated. Ether was added to the resulting residue to separate out a precipitate, which was collected by filtration.

Yield: 1.82 g (78.7%), Melting point: 102°–104° C., $Rf_1$: 0.34, $Rf_2$: 0.70 $[\alpha]_D^{28}$ +8.3° (c=1.22, in DMF)

Elemental analysis: As $C_{63}H_{77}N_7O_{14}$ Calculated: C, 65.44; H, 6.71; N, 8.48 Found: C, 65.32; H, 6.86; N, 8.53

(4) Production of Boc-D-Trp-D-Asp(OBzl)-Pro-Asp(OBzl)-D-Leu-Leu-OH

Boc-D-Trp-D-Asp(OBzl)-Pro-Asp(OBzl)-D-Leu-Leu-OPac (1.39 g) was dissolved in 90% aqueous AcOH (20 ml), and Zn powder (3.92 g) was added thereto, followed by stirring for 3 hours. The Zn powder was separated by filtration, and the filtrate was concentrated. AcOEt was added to the residue to dissolve it, and the solution was washed with 10% aqueous citric acid. After washing with water, the solution was dried with $Na_2SO_4$ and concentrated. Ether was added to the resulting residue to separate out a precipitate, which was collected by filtration.

Yield: 1.22 g (97.9%), Melting point: 110°–112° C., $Rf_1$: 0.13, $Rf_2$: 0.65 $[\alpha]_D^{28}$ +14.6° (c=1.07, in DMF)

Elemental analysis: As $C_{55}H_{71}N_7O_{13}$ Calculated: C, 63.63; H, 6.89; N, 9.44 Found: C, 63.62; H, 7.17; N, 9.25

(5) Production of cyclo[-D-Asp-Pro-Asp-D-Leu-Leu-D-Trp-]

Boc-D-Trp-D-Asp(OBzl)-Pro-Asp(OBzl)-D-Leu-Leu-OH (0.53 g) was dissolved in DCM (20 ml), and the solution was cooled with ice. HONB (0.18 g) and DCC (0.21 g) were added thereto, followed by stirring for 3 hours. Then, the resulting DCU was separated by filtration, followed by concentration, and ether was added to the residue to separate out a precipitate, which was collected by filtration. 8N-HCl/dioxane (20 ml) was added thereto under ice cooling to dissolve the precipitate. The resulting solution was stirred for 10 minutes and concentrated. Then, ether was added to the residue to separate out a precipitate, which was collected by filtration and dried. The precipitate was dissolved in DMF (10 ml), and the resulting solution was added dropwise to DMF (90 ml) containing TEA (0.7 ml) for 30 minutes, followed by stirring overnight and concentration. Acetonitrile-ether was added to the resulting residue to separate out a precipitate, which was collected by filtration and dried. Of this precipitate, 92 mg was dissolved in DMF (15 ml) and catalytically reduced in a stream of hydrogen using palladium black as a catalyst. The catalyst was separated by filtration, and the filtrate was concentrated. The resulting residue was dissolved in a small amount of AcOH, and then, water was added thereto to conduct lyophilization. Finally, the lyophilized product was purified by liquid chromatography using a YMC-D-ODS-5 column (2 cm×25 cm) (Y.M.C.) to obtain a desired material. The yield was 15.2 mg (47.4%).

Anal. for amino acids [6N-HCl, 110° C., hydrolysis for 24 hours; figures in parentheses show theoretical values.]: Asp 2.00(2); Pro 1.03(1); Leu 2.11(2) LSIMS $(M+H^+)$=740, (theoretical value)=740

EXAMPLE 10

Production of cyclo[-D-Asp-Asn(CH2Ph)-Asp-D-Leu-Leu-D-Trp-]

(1) Production of Boc-Asn($CH_2$Ph)-OBzl

Boc-Asp-OBzl (1.61 g, purchased from Watanabe Kagaku) was dissolved in acetonitrile (50 ml), and HONB (0.98 g) and DCC (1.13 g) were added thereto, followed by stirring for 2 hours under ice cooling. The resulting insoluble material was separated by filtration, and benzylamine (1.09 ml) was added thereto, followed by stirring overnight. After concentration of the reaction solution, the residue was dissolved in AcOEt, and the solution was washed with water, 10% aqueous citric acid and 4% aqueous $NaHCO_3$. After washing with water, the solution was dried with $Na_2SO_4$ and concentrated. Ether was added to the resulting residue to separate out a precipitate, which was collected by filtration.

Yield: 1.90 g (92.5%), Melting point: 116.5°–117.0° C., $Rf_1$: 0.56, $Rf_2$: 0.69 $[\alpha]_D^{25}$ −11.3° (c=1.05, in DMF)

Elemental analysis: As $C_{23}H_{28}N_2O_5$ Calculated: C, 66.97; H, 6.84; N, 6.79 Found: C, 67.25; H, 6.95; N, 7.07

(2) Production of Boc-Asn($CH_2$Ph)-Asp(OBzl)-D-Leu-Leu-OPac

Boc-Asp(OBzl)-D-Leu-Leu-OPac (2.00 g) was dissolved in 8N-HCl/dioxane (10 ml), and the solution was stirred under ice cooling for 10 minutes, followed by concentration. Then, ether was added to precipitate crystals. The crystals were separated by filtration and dried. The resulting product was dissolved in DMF (15 ml) and cooled with ice. Then, TEA (0.44 ml) was added thereto. Boc-Asn($CH_2$Ph)-ONB [prepared by catalytically reducing Boc-Asn($CH_2$Ph)-OBzl (1.23 g) synthesized in (1), in methanol (20 ml) in the presence of 10% Pd-carbon (20 mg) in a stream of hydrogen at ordinary temperature and pressure, separating the catalyst by filtration, followed by concentration, dissolving the residue in acetonitrile, and then adding HONB (0.56 g) and DCC (0.65 g) thereto under ice cooling] was added, followed by stirring overnight. The resulting insoluble material was separated by filtration, followed by concentration. The residue was dissolved in AcOEt, and the solution was washed with water, 10% aqueous citric acid and 4% aqueous $NaHCO_3$. After washings-with water, the solution was dried with $Na_2SO_4$ and concentrated. Ether was added to the resulting residue to separate out a precipitate, which was collected by filtration.

Yield: 2.26 g (86.7%), Melting point: 155.0°–157.0° C., $Rf_1$: 0.49, $Rf_2$: 0.70 $[\alpha]_D^{25}$ −37.1° (c=1.05, in DMF)

Elemental analysis: As $C_{47}H_{61}N_5O_{11}$ Calculated: C, 64.74; H, 7.05; N, 8.03 Found: C, 64.80; H, 7.19; N, 8.25

(3) Production of Boc-D-Asp(OBzl)-Asn(CH2Ph)-Asp(OBzl)-D-Leu-Leu-OPac

Boc-Asn($CH_2$ph)-Asp(OBzl)-D-Leu-Leu-OPac (1.92 g) was dissolved in 8N-HCl/dioxane (10 ml), and the solution was stirred under ice cooling for 10 minutes, followed by concentration. Then, ether was added to precipitate crystals. The crystals were separated by filtration and dried. The resulting product was dissolved in DMF (15 ml) and cooled with ice. Then, TEA (0.32 ml) was added thereto. Boc-D-Asp(OBzl)-ONB [prepared from Boc-D-Asp(OBzl)-OH (0.71 g), HONB (0.41 g) and DCC (0.46 g)] was added thereto, followed by stirring overnight. The resulting insoluble material was separated by filtration, followed by concentration. The residue was dissolved in AcOEt, and the solution was washed with water, 10% aqueous citric acid and 4% aqueous $NaHCO_3$. After washing with water, the solution was dried with $Na_2SO_4$ and concentrated. Ether was added to the resulting residue to separate out a precipitate, which was collected by filtration.

Yield: 2.22 g (93.9%), Melting point: 141.5°–143.0° C., $Rf_1$: 0.57, $Rf_2$: 0.75 $[\alpha]_D^{25}$ −22.7° (c=1.01, in DMF)

Elemental analysis: As $C_{58}H_{72}N_6O_{14}$ Calculated: C, 64.67; H, 6.74; N, 7.80 Found: C, 64.46; H, 6.86; N, 7.91

(4) Production of Boc-D-Trp-D-Asp(OBzl)-Asn($CH_2$Ph)-Asp(OBzl)-D-Leu-Leu-OPac

Boc-D-Asp(OBzl)-Asn($CH_2$Ph)-Asp(OBzl)-D-Leu-Leu-OPac (1.93 g) was dissolved in 8-N HCl/dioxane (10 ml), and the solution was stirred under ice cooling for 10 minutes, followed by concentration. Then, ether was added to precipitate crystals. The crystals were separated by filtration and dried. The resulting product was dissolved in DMF (15 ml) and cooled with ice. Then, TEA (0.27 ml) was added thereto. Boc-D-Trp-ONB [prepared from Boc-D-Trp-OH (0.55 g), HONB (0.34 g) and DCC (0.39 g)] was added thereto, followed by stirring overnight. The resulting insoluble material was separated by filtration, followed by concentration. The residue was dissolved in AcOEt, and the solution was washed with water, 10% aqueous citric acid and 4% aqueous $NaHCO_3$. After washing with water, the solution was dried with Na$_2$SO$_4$ and concentrated. Ether was added to the resulting residue to separate out a precipitate, which was collected by filtration.

Yield: 1.85 g (81.6%), Melting point: 149.0°–151.0° C., Rf$_1$: 0.47, Rf$_2$: 0.71 [α]$_D^{25}$ −9.8° (c=1.03, in DMF)

Elemental analysis: As C$_{69}$H$_{82}$N$_8$O$_{15}$ Calculated: C, 65.59; H, 6.54; N, 8.87 Found: C, 65.36; H, 6.70; N, 8.89

(5) Production of Boc-D-Trp-D-Asp(OBzl)-Asn(CH$_2$Ph)-Asp(OBzl)-D-Leu-Leu-OH

Boc-D-Trp-D-Asp(OBzl)-Asn(CH$_2$Ph)-Asp(OBzl)-D-Leu-Leu-OPac (500 mg) was dissolved in 90% aqueous AcOH (20 ml), and Zn powder (1.30 g) was added thereto, followed by stirring for 3 hours. The Zn powder was separated by filtration, and the filtrate was concentrated. AcOEt was added to the residue to dissolve it, and the solution was washed with 10% aqueous citric acid. After washing with water, the solution was dried with Na$_2$SO$_4$ and concentrated. Ether was added to the resulting residue to separate out a precipitate, which was collected by filtration.

Yield: 436 mg (96.1%), Melting point: 153.0°–155.0° C., Rf$_1$: 0.02, Rf$_2$: 0.67 [α]$_D^{25}$ −3.2° (c=1.02, in DMF)

Elemental analysis: As C$_{61}$H$_{76}$N$_8$O$_{14}$ Calculated: C, 63.97; H, 6.69; N, 9.78 Found: C, 63.85; H, 6.74; N, 9.51

(6) Production of cyclo[-D-Asp-Asn(CH$_2$Ph)-Asp-D-Leu-Leu-D-Trp-]

Boc-D-Trp-D-Asp(OBzl)-Asn(CH$_2$Ph)-Asp(OBzl)-D-Leu-Leu-OH (396 mg) was dissolved in DCM (20 ml), and the solution was cooled with ice. HONB (0.14 g) and DCC (0.16 g) were added thereto, followed by stirring for 3 hours. Then, the resulting DCU was separated by filtration, followed by concentration, and ether was added to the residue to separate out a precipitate, which was collected by filtration. 8N-HCl/dioxane (20 ml) was added thereto under ice cooling to dissolve the precipitate. The resulting solution was stirred for 10 minutes and concentrated. Then, ether was added to the residue to separate out a precipitate, which was collected by filtration and dried. The precipitate was dissolved in DMF (10 ml), and the resulting solution was added dropwise to DMF (90 ml) containing TEA (0.55 ml) for 30 minutes, followed by stirring overnight and concentration. Acetonitrile-ether was added to the resulting residue to separate out a precipitate, which was collected by filtration and dried. Of this precipitate, 50 mg was dissolved in DMF (15 ml) and catalytically reduced in a stream of hydrogen using palladium black as a catalyst. The catalyst was separated by filtration, and the filtrate was concentrated. The resulting residue was dissolved in a small amount of AcOH, and then, water was added thereto to conduct lyophilization. Finally, the lyophilized product was purified by liquid chromatography using a YMC-D-ODS-5 column (2 cm×25 cm) (Y.M.C.) to obtain a desired material. The yield was 19.5 mg (23.8%).

Anal for amino acids [6N-HCl, 110° C., hydrolysis for 24 hours; figures in parentheses show theoretical values.]: Asp 3.00(3); Leu 2.00(2) LSIMS (M+H$^+$)=847, (theoretical value)=847

EXAMPLE 11

Production of cyclo[-D-Asp-Asn(CH$_2$CH$_2$Ph)-AsP-D-Leu-Leu-D-Trp-]

(1) Production of Boc-Asn(CH$_2$CH$_2$Ph)-OBzl

Boc-Asp-OBzl (1.61 g, purchased from Watanabe Kagaku) was dissolved in acetonitrile (50 ml), and HONB (0.98 g) and DCC (1.13 g) were added thereto, followed by stirring for 2 hours under ice cooling. The resulting insoluble material was separated by filtration, and β-phenethylamine (0.79 ml) was added thereto, followed by stirring overnight. After concentration of the reaction solution, the residue was dissolved in AcOEt, and the solution was washed with water, 10% aqueous citric acid and 4% aqueous NaHCO$_3$. After washing with water, the solution was dried with Na$_2$SO$_4$ and concentrated. Ether was added to the resulting residue to separate out a precipitate, which was collected by filtration.

Yield: 1.96 g (92.3%), Melting point: 117.0°–118.5° C., Rf$_1$: 0.53, Rf$_2$: 0.68 [α]$_D^{25}$ −7.3° (c=1.00, in DMF)

Elemental analysis: As C$_{24}$H$_{30}$N$_2$O$_5$ Calculated: C, 67.59; H, 7.09; N, 6.57 Found: C, 67.68; H, 7.15; N, 6.75

(2) Production of Boc-Asn(CH$_2$CH$_2$Ph)-Asp(OBzl)-D-Leu-Leu-OPac

Boc-Asp(OBzl)-D-Leu-Leu-OPac (2.00 g) was dissolved in 8N-HCl/dioxane (10 ml), and the solution was stirred under ice cooling for 10 minutes, followed by concentration. Then, ether was added to precipitate crystals. The crystals were separated by filtration and dried. The resulting product was dissolved in DMF (15 ml) and cooled with ice. Then, TEA (0.44 ml) was added thereto. Boc-Asn(CH$_2$CH$_2$Ph)-ONB [prepared by catalytically reducing Boc-Asn(CH$_2$CH$_2$Ph)-OBzl (1.28 g) synthesized in (1), in methanol (20 ml) in the presence of 10% Pd-carbon (20 mg) in a stream of hydrogen at ordinary temperature and pressure, separating the catalyst by filtration, followed by concentration, dissolving the residue in acetonitrile, and then adding HONB (0.56 g) and DCC (0.65 g) thereto under ice cooling] was added thereto, followed by stirring overnight. The resulting insoluble material was separated by filtration, followed by concentration. The residue was dissolved in AcOEt, and the solution was washed with water, 10% aqueous citric acid and 4% aqueous NaHCO$_3$. After washing with water, the solution was dried with Na$_2$SO$_4$ and concentrated. Ether was added to the resulting residue to separate out a precipitate, which was collected by filtration.

Yield: 2.35 g (88.7%), Melting point: 162.0°–164.0° C., Rf$_1$: 0.59, Rf$_2$: 0.65 [α]$_D^{25}$ −36.7° (c=1.03, in DMF)

Elemental analysis: As C$_{48}$H$_{63}$N$_5$O$_{11}$ Calculated: C, 65.07; H, 7.17; N, 7.90 Found: C, 65.15; H, 7.20; N, 8.08

(3) Production of Boc-D-Asp(OBzl)-Asn(CH$_2$CH$_2$Ph)-Asp(OBzl)-D-Leu-Leu-OPac

Boc-Asn(CH$_2$CH$_2$Ph)-Asp(OBzl)-D-Leu-Leu-OPac (1.95 g) was dissolved in 8-N HCl/dioxane (10 ml), and the solution was stirred under ice cooling for 10 minutes, followed by concentration. Then, ether was added to precipitate crystals. The crystals were separated by filtration and then dried. The resulting product was dissolved in DMF (15 ml) and cooled with ice. Then, TEA (0.32 ml) was added thereto. Boc-D-Asp(OBzl)-ONB [prepared from Boc-D-Asp(OBzl)-OH (0.71 g), HONB (0.41 g) and DCC (0.46 g)] was added thereto, followed by stirring overnight. The resulting insoluble material was separated by filtration, followed by concentration. The residue was dissolved in AcOEt, and the solution was washed with water, 10% aqueous citric acid and 4% aqueous NaHCO$_3$. After washing with water, the solution was dried with Na$_2$SO$_4$ and concentrated. Ether was added to the resulting residue to separate out a precipitate, which was collected by filtration.

Yield: 2.24 g (93.5%), Melting point: 173.0°–175.0° C., Rf$_1$: 0.39, Rf$_2$: 0.66 [α]$_D^{25}$ −21.6° (c=1.02, in DMF)

Elemental analysis: As C$_{59}$H$_{74}$N$_6$O$_{14}$ Calculated: C, 64.94; H, 6.83; N, 7.70 Found: C, 64.82; H, 6.93; N, 7.85

(4) Production of Boc-D-Trp-D-Asp(OBzl)-Asn(CH$_2$CH$_2$Ph)-Asp(OBzl)-D-Leu-Leu-OPac Boc-D-Asp(OBzl)-Asn(CH$_2$CH$_2$Ph)-Asp(OBzl)-D-Leu-Leu-OPac (1.95 g) was dissolved in 8-N HCl/dioxane (10 ml), and the solution was stirred under ice cooling for 10 minutes, followed by concentration. Then, ether was added to precipitate crystals. The crystals were separated by filtration and then dried. The resulting product was dissolved in DMF (15 ml) and cooled with ice. Then, TEA (0.27 ml) was added thereto. Boc-D-Trp-ONB [prepared from Boc-D-Trp-OH (0.55 g), HONB (0.34 g) and DCC (0.39 g)] was added thereto, followed by stirring overnight. The resulting insoluble material was separated by filtration, followed by concentration. The residue was dissolved in AcOEt, and the solution was washed with water, 10% aqueous citric acid and 4% aqueous NaHCO$_3$. After washing with water, the solution was dried with Na$_2$SO$_4$ and concentrated. Ether was added to the resulting residue to separate out a precipitate, which was collected by filtration.

Yield: 2.07 g (90.5%), Melting point: 139.5°–141.0° C., Rf$_1$: 0.24, Rf$_2$: 0.65 [α]$_D^{25}$ −7.6° (c=1.00, in DMF)

Elemental analysis: As C$_{70}$H$_{84}$N$_8$O$_{15}$ Calculated: C, 65.81; H, 6.63; N, 8.77 Found: C, 65.58; H, 6.71; N, 8.94

(5) Production of Boc-D-Trp-D-Asp(OBzl)-Asn(CH$_2$CH$_2$Ph)-Asp(OBzl)-D-Leu-Leu-OH Boc-D-Trp-D-Asp(OBzl)-Asn(CH$_2$CH$_2$Ph)-Asp(OBzl)-D-Leu-Leu-OPac (500 mg) was dissolved in 90% aqueous AcOH (20 ml), and Zn powder (1.28 g) was added thereto, followed by stirring for 3 hours. The Zn powder was separated by filtration, and the filtrate was concentrated. AcOEt was added to the residue to dissolve it, and the solution was washed with 10% aqueous citric acid. After washing with water, the solution was dried with Na$_2$SO$_4$ and concentrated. Ether was added to the resulting residue to separate out a precipitate, which was collected by filtration.

Yield: 441 mg (97.3%), Melting point: 170.0°–172.0° C., Rf$_1$: 0.03, Rf$_2$: 0.67 [α]$_D^{25}$ −1.8° (c=1.03, in DMF)

Elemental analysis: As C$_{62}$H$_{78}$N$_8$O$_{14}$ Calculated: C, 64.23; H, 6.78; N, 9.67 Found: C, 64.08; H, 6.86; N, 9.55

(6) Production of cyclo[-D-Asp-Asn(CH$_2$CH$_2$Ph)-Asp-D-Leu-Leu-D-Trp-]

Boc-D-Trp-D-Asp(OBzl)-Asn(CH$_2$CH$_2$Ph)-Asp(OBzl)-D-Leu-Leu-OH (401 mg) was dissolved in DCM (20 ml), and the solution was cooled with ice. HONB (0.14 g) and DCC (0.16 g) were added thereto, followed by stirring for 3 hours. Then, the resulting DCU was separated by filtration, followed by concentration, and ether was added to the residue to separate out a precipitate, which was collected by filtration. 8N-HCl/dioxane (20 ml) was added thereto under ice cooling to dissolve the precipitate. The resulting solution was stirred for 10 minutes and concentrated. Then, ether was added to the residue to separate out a precipitate, which was collected by filtration and dried. The precipitate was dissolved in DMF (10 ml), and the resulting solution was added dropwise to DMF (90 ml) containing TEA (0.55 ml) for 30 minutes, followed by stirring overnight and concentration. Acetonitrile-ether was added to the resulting residue to separate out a precipitate, which was collected by filtration and dried. Of this precipitate, 50 mg was dissolved in DMF (15 ml) and catalytically reduced in a stream of hydrogen using palladium black as a catalyst. The catalyst was separated by filtration, and the filtrate was concentrated. The resulting residue was dissolved in a small amount of AcOH, and then, water was added thereto to conduct lyophilization. Finally, the lyophilized product was purified by liquid chromatography using a YMC-D-ODS-5 column (2 cm×25 cm) (Y.M.C.) to obtain a desired material. The yield was 20.5 mg (24.1%).

Anal. for amino acids [6N-HCl, 110° C., hydrolysis for 24 hours; figures in parentheses show theoretical values.]: Asp 3.00(3); Leu 2.04(2) LSIMS (M+H$^+$)=861, (theoretical value)=861

EXAMPLE 12

Production of cyclo[-D-Asp-Asn(CH$_2$CH$_2$-Ind)-Asp-D-Leu-Leu-D-Trp-]

(1) Production of Boc-Asn(CH$_2$CH$_2$-Ind)-OBzl

Boc-Asp-OBzl (1.61 g, purchased from Watanabe Kagaku) was dissolved in acetonitrile (50 ml), and HONB (0.98 g) and DCC (1.13 g) were added thereto, followed by stirring for 2 hours under ice cooling. The resulting insoluble material was separated by filtration, and DMF (20 ml) containing tryptamine hydrochloride (0.98 ml) and TEA (1.04 ml) was added thereto, followed by stirring overnight. After concentration of the reaction solution, the residue was dissolved in AcOEt, and the solution was washed with water, 10% aqueous citric acid and 4% aqueous NaHCO$_3$. After washing with water, the solution was dried with Na$_2$SO$_4$ and concentrated. Ether was added to the resulting residue to obtain a desired product as a light yellow glassy material.

Yield: 1.95 g (84.1%), Rf$_1$: 0.42, Rf$_2$: 0.67 LSIMS (M+H$^+$)=466, (theoretical value)=466

(2) Production of Boc-Asn(CH$_2$CH$_2$-Ind)-Asp(OBzl)-D-Leu-Leu-OPac

Boc-Asp(OBzl)-D-Leu-Leu-OPac (2.00 g) was dissolved in 8N-HCl/dioxane (10 ml), and the solution was stirred under ice cooling for 10 minutes, followed by concentration. Then, ether was added to precipitate crystals. The crystals were separated by filtration and then dried. The resulting product was dissolved in DMF (15 ml) and cooled with ice. Then, TEA (0.44 ml) was added thereto. Boc-Asn(CH$_2$CH$_2$-Ind)-ONB [prepared by catalytically reducing Boc-Asn(CH$_2$CH$_2$-Ind)-OBzl (1.35 g) synthesized in (1), in methanol (20 ml) in the presence of 10% Pd-carbon (20 mg) in a stream of hydrogen at ordinary temperature and pressure, separating the catalyst by filtration, followed by concentration, dissolving the residue in acetonitrile, and then adding HONB (0.56 g) and DCC (0.65 g) thereto under ice cooling] was added thereto, followed by stirring overnight. The resulting insoluble material was separated by filtration, followed by concentration. The residue was dissolved in AcOEt, and the solution was washed with water, 10% aqueous citric acid and 4% aqueous NaHCO$_3$. After washing with water, the solution was dried with Na$_2$SO$_4$ and concentrated. Ether was added to the resulting residue to separate out a precipitate, which was collected by filtration.

Yield: 2.16 g (78.1%), Melting point: 141.0°–143.0° C., Rf$_1$: 0.46, Rf$_2$: 0.73 [α]$_D^{25}$ −35.8° (c=1.06, in DMF)

Elemental analysis: As C$_{50}$H$_{64}$N$_6$O$_{11}$ Calculated: C, 64.92; H, 6.97; N, 9.08 Found: C, 64.63; H, 7.11; N, 8.96

(3) Production of Boc-D-Asp(OBzl)-Asn(CH$_2$CH$_2$-Ind)-Asp(OBzl)-D-Leu-Leu-OPac Boc-Asn(CH$_2$CH$_2$-Ind)-Asp(OBzl)-D-Leu-Leu-OPac (2.00 g) was dissolved in 8N-HCl/dioxane (10 ml), and the solution was stirred under ice cooling for 10 minutes, followed by concentration. Then, ether was added to precipitate crystals. The crystals were separated by filtration and then dried. The resulting product was dissolved in DMF (15 ml) and cooled with ice. Then, TEA (0.32 ml) was added thereto. Boc-D-Asp(OBzl)-ONB [prepared from Boc-D-Asp(OBzl)-OH (0.71 g), HONB (0.41 g) and DCC (0.46 g)] was added thereto, followed by stirring overnight. The resulting insoluble material was separated by filtration, followed by concentration. The residue was dissolved in AcOEt, and the solution was washed with water, 10% aqueous citric acid and 4% aqueous NaHCO$_3$. After washing with water, the solution was dried with Na$_2$SO$_4$ and concentrated. Ether was added to the resulting residue to separate out a precipitate, which was collected by filtration.

Yield: 2.12 g (85.4%), Melting point: 112.5°–114.0° C., Rf$_1$: 0.50, Rf$_2$: 0.70 [α]$_D^{25}$ −22.0° (c=1.02, in DMF)

(4) Production of Boc-D-Trp-D-Asp(OBzl)-Asn(CH$_2$CH$_2$-Ind)-Asp(OBzl)-D-Leu-Leu-OPac Boc-D-Asp(OBzl)-Asn(CH$_2$CH$_2$-Ind)-Asp(OBzl)-D-Leu-Leu-OPac (2.00 g) was dissolved in 8-N HCl/dioxane (10 ml), and the solution was stirred under ice cooling for 10 minutes, followed by concentration. Then, ether was added to precipitate crystals. The crystals were separated by filtration and then dried. The resulting product was dissolved in DMF (15 ml) and cooled with ice. Then, TEA (0.27 ml) was added thereto. Boc-D-Trp-ONB [prepared from Boc-D-Trp-OH (0.55 g), HONB (0.34 g) and DCC (0.39 g)] was added thereto, followed by stirring overnight. The resulting insoluble material was separated by filtration, followed by concentration. The residue was dissolved in AcOEt, and the solution was washed with water, 10% aqueous citric acid and 4% aqueous NaHCO$_3$. After washing with water, the solution was dried with Na$_2$SO$_4$ and concentrated. Ether was added to the resulting residue to separate out a precipitate, which was collected by filtration.

Yield: 2.11 g (89.5%), Melting point: 113.0°–115.0° C., Rf$_1$: 0.42, Rf$_2$: 0.68 [α]$_D^{25}$ –9.2° (c=1.04, in DMF)

Elemental analysis: As C$_{72}$H$_{85}$N$_9$O$_{15}$ Calculated: C, 65.69; H, 6.51; N, 9.58 Found: C, 65.60; H, 6.60; N, 9.49

(5) Production of Boc-D-Trp-D-Asp(OBzl)-Asn(CH$_2$CH$_2$-Ind)-Asp(OBzl)-D-Leu-Leu-OH Boc-D-Trp-D-Asp(OBzl)-Asn(CH$_2$CH$_2$-Ind)-Asp(OBzl)-D-Leu-Leu-OPac (500 mg) was dissolved in 90% aqueous AcOH (20 ml), and Zn powder (1.26 g) was added thereto, followed by stirring for 3 hours. The Zn powder was separated by filtration, and the filtrate was concentrated. AcOEt was added to the residue to dissolve it, and the solution was washed with 10% aqueous citric acid. After washing with water, the solution was dried with Na$_2$SO$_4$ and concentrated. Ether was added to the resulting residue to separate out a precipitate, which was collected by filtration.

Yield: 426 mg (92.5%), Melting point: 115.0°–117.5° C., Rf$_1$: 0.01, Rf$_2$: 0.65 [α]$_D^{25}$ –1.4° (c=1.06, in DMF)

Elemental analysis: As C$_{64}$H$_{79}$N$_9$O$_{14}$ Calculated: C, 64.15; H, 6.64; N, 10.52 Found: C, 64.07; H, 6.74; N, 10.38

(6) Production of cyclo[-D-Asp-Asn(CH$_2$CH$_2$-Ind)-Asp-D-Leu-Leu-D-Trp-]

Boc-D-Trp-D-Asp(OBzl)-Asn(CH$_2$CH$_2$-Ind)-Asp(OBzl)-D-Leu-Leu-OH (386 mg) was dissolved in DCM (20 ml), and the solution was cooled with ice. HONB (0.14 g) and DCC (0.16 g) were added thereto, followed by stirring for 3 hours. Then, the resulting DCU was separated by filtration, followed by concentration, and ether was added to the residue to separate out a precipitate, which was collected by filtration. 8N-HCl/dioxane (20 ml) was added thereto under ice cooling to dissolve the precipitate. The resulting solution was stirred for 10 minutes and concentrated. Then, ether was added to the residue to separate out a precipitate, which was collected by filtration and dried. The precipitate was dissolved in DMF (10 ml), and the resulting solution was added dropwise to DMF (90 ml) containing TEA (0.54 ml) for 30 minutes, followed by stirring overnight and concentration. Acetonitrile-ether was added to the resulting residue to separate out a precipitate, which was collected by filtration and dried. Of this precipitate, 40 mg was dissolved in DMF (15 ml) and catalytically reduced in a stream of hydrogen using palladium black as a catalyst. The catalyst was separated by filtration, and then the filtrate was concentrated. The resulting residue was dissolved in a small amount of AcOH, and thereafter, water was added thereto to conduct lyophilization. Finally, the lyophilized product was purified by liquid chromatography using a YMC-D-ODS-5 column (2 cm×25 cm) (Y.M.C.) to obtain a desired material. The yield was 19.6 mg (19.4%).

Anal. for amino acids [6N-HCl, 110° C., hydrolysis for 24 hours; figures in parentheses show theoretical values.]: Asp 3.00(3); Leu 2.35(2) LSIMS (M+H$^+$)=900, (theoretical value)=900

EXAMPLE 13

Production of cyclo[-D-Asp-Hyp(Bzl)-Asp-D-Leu-Leu-D-Trp-]

(1) Production of Boc-Hyp(Bzl)-Asp(OBzl)-D-Leu-Leu-OPac

Boc-Asp(OBzl)-D-Leu-Leu-OPac (2.34 g) was dissolved in dioxane (1.0 ml), and the solution was cooled with ice. 10N-HCl/dioxane (5.0 ml) was added thereto, followed by stirring for 30 minutes. The solvent was removed by distillation at room temperature, and ether was added to the residue to separate out a precipitate, which was collected by filtration and dried under reduced pressure. The resulting product was dissolved in DMF (15 ml), and neutralized with TEA with stirring under ice cooling. Boc-Hys(Bzl)-ONB prepared from Boc-Hyp(Bzl)-OH (1.57 g), HONB (1.16 g) and DCC (1.55 g) was added thereto and stirred overnight at room temperature. The resulting insoluble material was removed by filtration, and the filtrate was concentrated. The residue was dissolved in AcOEt, and the solution was washed successively with 10% aqueous citric acid, 4% aqueous NaHCO$_3$ and a saturated aqueous solution of sodium chloride. After drying with Na$_2$SO$_4$, the solvent was removed by distillation, and ether was added to the residue to separate out a precipitate, which was collected by filtration. The precipitate was recrystallized from AcOEt-petroleum.

Yield: 4.01 g (92.0%), Melting point: 73.0°–74.0° C., Rf$_1$: 0.44, Rf$_2$: 0.72 [α]$_D^{25}$ –33.3° (c=1.00, in DMF)

Elemental analysis: As C$_{48}$H$_{62}$N$_4$O$_{11}$ Calculated: C, 66.19; H, 7.17; N, 6.43 Found: C, 66.19; H, 7.33; N, 6.68

(2) Production of Boc-D-Asp(OBzl)-Hyp(Bzl)-Asp(OBzl)-D-Leu-Leu-OPac

Boc-Hyp(Bzl)-Asp(OBzl)-D-Leu-Leu-OPac (3.49 g) was dissolved in dioxane (1.0 ml), and the solution was cooled with ice. 10-N HCl/dioxane (5.0 ml) was added thereto, followed by stirring for 30 minutes. The solvent was removed by distillation at room temperature, and ether was added to the residue to separate out a precipitate, which was collected by filtration and dried under reduced pressure. The resulting product was dissolved in DMF (15 ml), and neutralized with TEA with stirring under ice cooling. Boc-D-Asp(OBzl)-ONB prepared from Boc-D-Asp(OBzl)-OH (1.55 g), HONB (1.08 g) and DCC (1.44 g) was added thereto and stirred overnight at room temperature. The resulting insoluble material was removed by filtration, and the filtrate was concentrated. The residue was dissolved in AcOEt, and the solution was washed successively with 10% aqueous citric acid, 4% aqueous NaHCO$_3$ and a saturated aqueous solution of sodium chloride. After drying with Na$_2$SO$_4$, the solvent was removed by distillation, and the residue was purified by silica gel chromatography (Merck Kiesel Gel 60. 2% methanol/chloroform) to obtain an oily product.

Yield: 3.63 g (84.3%), Rf$_1$: 0.42, Rf$_2$: 0.74 LSIMS (M+H$^+$)=1077, (theoretical value)=1077

(3) Production of Boc-D-Trp-D-Asp(OBzl)-Hyp(Bzl)-Asp(OBzl)-D-Leu-Leu-OPac

Boc-D-Asp(OBzl)-Hyp(Bzl)-Asp(OBzl)-D-Leu-Leu-OPac (3.77 g) was dissolved in dioxane (1.0 ml), and the solution was cooled with ice. 10-N HCl/dioxane (5.0 ml) was added thereto, followed by stirring for 30 minutes. The solvent was removed by distillation at room temperature, and ether was added to the residue to separate out a precipitate, which was collected by filtration and dried under reduced pressure. The resulting product was dissolved in DMF (15 ml), and neutralized with TEA with stirring under ice cooling. Boc-D-Trp-ONB prepared from Boc-D-Trp-OH (1.17 g), HONB (752 mg) and DCC (939 mg) was added thereto and stirred overnight at room temperature. The resulting insoluble material was removed by filtration, and the filtrate was concentrated. The residue was dissolved in AcOEt, and the solution was washed successively with 10% aqueous citric acid, 4% aqueous NaHCO$_3$ and a saturated aqueous solution of sodium chloride. After drying with Na$_2$SO$_4$, the solvent was removed by distillation, and the residue was purified by silica gel chromatography (Merck Kiesel Gel 60. 2% methanol/chloroform). Then, ether-petroleum ether was added thereto to separate out a precipitate, which was collected by filtration.

Yield: 3.44 g (91.4%), Melting point: 84.0°–85.0° C., Rf$_1$: 0.37, Rf$_2$: 0.72 [α]$_D^{25}$ 12.8° (c=1.00, in DMF)

Elemental analysis: As C$_{70}$H$_{83}$N$_7$O$_{15}$ Calculated: C, 66.60; H, 6.63; N, 7.77 Found: C, 66.65; H, 6.68; N, 7.76

(4) Production of Boc-D-Trp-D-Asp(OBzl)-Hyp(Bzl)-Asp(OBzl)-D-Leu-Leu-OH

Boc-D-Trp-D-Asp(OBzl)-Hyp(Bzl)-Asp(OBzl)-D-Leu-Leu-OPac (2.52 g) was dissolved in 90% aqueous AcOH (50 ml), and Zn powder (6.54 g) was added thereto with stirring under ice cooling, further followed by stirring at room temperature. The Zn powder was removed by filtration, and filtrate was concentrated. The residue was dissolved in AcOEt, and the solution was washed successively with 10% aqueous citric acid and a saturated aqueous solution of sodium chloride. After drying with Na$_2$SO$_4$, the solvent was removed by distillation, and ether-petroleum ether was added to the residue to separate out a precipitate, which was collected by filtration and dried under reduced pressure.

Yield: 2.29 g (quantitative), Melting point: 94.0°– 96.0° C., Rf$_1$: 0.17, Rf$_2$: 0.70 [α]$_D^{25}$ 19.2° (c=1.00, in DMF)

Elemental analysis: As C$_{62}$H$_{77}$N$_7$O$_{14}$ Calculated: C, 65.07; H, 6.78; N, 8.57 Found: C, 65.05; H, 6.86; N, 8.39

(5) Production of cyclo[-D-Asp(OBzl)-Hyp(Bzl)-Asp(OBzl)-D-Leu-Leu-D-Trp-]

Boc-D-Trp-D-Asp(OBzl)-Hyp(Bzl)-Asp(OBzl)-D-Leu-Leu-OH (1.14 g) was dissolved in dichloromethane (10 ml), and HONB (358 mg) and DCC (413 mg) were successively added thereto with stirring under ice cooling, further followed by stirring under ice cooling for 3 hours. The resulting insoluble material was removed by filtration, and the solvent was removed by distillation. The residue was dissolved in acetonitrile (20 ml), and the insoluble material was removed by filtration. The solvent was removed by distillation, and ether-petroleum ether was added to the residue to separate out a precipitate, which was collected by filtration and dried under reduced pressure. The resulting product was dissolved in dioxane (2 ml), and 10N-HCl/dioxane (10 ml) was added thereto with stirring under ice cooling, further followed by stirring for 10 minutes. The solvent was removed by distillation at room temperature, and ether was added to the residue to separate out a precipitate, which was collected by filtration and dried under reduced pressure. This was dissolved in DMF (5 ml), and the resulting solution was added dropwise to DMF (100 ml) containing TEA (6.96 ml), followed by stirring overnight. The solvent was removed by distillation, and the residue was dissolved in AcOEt. The solution was washed successively with 10% aqueous citric acid, 5% aqueous NaHCO$_3$ and a saturated aqueous solution of sodium chloride. After drying with Na$_2$SO$_4$, the solvent was removed by distillation, and the residue was purified by silica gel chromatography (Merck Kiesel Gel 60. 1% methanol/chloroform). Then, ether-petroleum ether was added thereto to separate out a precipitate, which was collected by filtration and dried under reduced pressure.

Yield: 847 mg (82.6%), Rf$_1$: 0.40, Rf$_2$: 0.74

(6) Production of cyclo[-D-Asp-Hyp(Bzl)-Asp-D-Leu-Leu-D-Trp-]

Cyclo[-D-Asp(OBzl)-Hyp(Bzl)-Asp(OBzl)-D-Leu-Leu-D-Trp-] (103 mg) was dissolved in DMF (10 ml), and palladium black (100 mg) was added thereto. The mixture was vigorously stirred in a stream of hydrogen at room temperature for 1 hour. The catalyst was removed by filtration, and the filtrate was concentrated. Then, ether was added to the residue to separate out a precipitate, which was collected by filtration and dried under reduced pressure. The yield was 64 mg (82.6%). Of this precipitate, 30.0 mg was purified by reversed phase liquid chromatography [column: YMC-D-ODS-5 (2 cm×25 cm)]. The yield was 23.7 mg (79.0%).

Anal. for amino acids [6N-HCl, 110° C., hydrolysis for 24 hours; figures in parentheses show theoretical values.]: Asp 2.00(2); Leu 1.97(2); Hyp 0.84 (1) LSIMS (M+H$^+$)=846, (theoretical value)=846

EXAMPLE 14

Production of cyclo[-D-Asp-Hyp-Asp-D-Leu-Leu-D-Trp-]

Cyclo[-D-Asp(OBzl)-Hyp(Bzl)-Asp(OBzl)-D-Leu-Leu-D-Trp-] (103 mg) was dissolved in DMF (10 ml), and palladium black (100 mg) was added thereto. The mixture was vigorously stirred in a stream of hydrogen at room temperature for 1 hour. The catalyst was removed by filtration, and the filtrate was concentrated. Then, ether was added to the residue to separate out a precipitate, which was collected by filtration and dried Under reduced pressure. The resulting product was dissolved in methanol (10 ml), and palladium black (100 mg) was added thereto. The mixture was vigorously stirred overnight in a stream of hydrogen at room temperature. The catalyst was removed by filtration, and the filtrate was concentrated. Then, ether was added to the residue to separate out a precipitate, which was collected by filtration and dried under reduced pressure. The yield was 65 mg (85.7%). Of this precipitate, 25.0 mg was purified by reversed phase liquid chromatography [column: YMC-D-ODS-5 (2 cm×25 cm)]. The yield was 19.7 mg (78.8%).

Anal. for amino acids [6N-HCl, 110° C., hydrolysis for 24 hours; figures in parentheses show theoretical values.]: Asp 2.00(2); Leu 2.00(2); Hyp 0.97 (1) LSIMS (M+H$^+$)=756, (theoretical value)=756

EXAMPLE 53

Production of cyclo[-D-Asp-Trp-Asp-D-tLeu-Leu-D-Trp-]

(1) Production of Boc-Asp(OBzl)-OPac

Boc-Asp(OBzl)-OH (32.3 g) and Cs$_2$CO$_3$ (16.3 g) were dissolved in 90% aqueous methanol, and the solution was concentrated. The residue was dissolved in DMF (300 ml), and phenacyl bromide (21.9 g) was added thereto, followed by stirring overnight. The resulting CsBr was separated by filtration, and the filtrate was concentrated. The residue was dissolved in AcOEt, and the solution was washed with 4% aqueous NaHCO$_3$ and 10% aqueous citric acid. After washing with water, the solution was dried with $Na_2SO_4$ and concentrated. Then, the residue was recrystallized from ethyl acetate-petroleum ether.

Yield: 42.9 g (97.1%), Melting point: 73°–74° C., $Rf_1$: 0.69, $Rf_2$: 0.82 $[\alpha]_D^{28}$ –21.8° (c=0.99, in DMF)

Elemental analysis: As $C_{24}H_{27}NO_7$ Calculated: C, 65.29; H, 6.16; N, 3.17 Found: C, 65.42; H, 6.25; N, 3.32

(2) Production of Boc-Trp-Asp(OBzl)-OPac

Boc-Trp-OH (12.2 g) was dissolved in THF, and the solution was cooled to –15° C. with stirring. Then, N-methylmorpholine (4.4 ml) was added thereto, and subsequently, IBCF (5.4 ml) was added. After 2 minutes, a DMF solution of HCl.H-Asp(OBzl)-OPac and N-methylmorpholine was added. HCl.H-Asp(OBzl)-OPac was obtained by dissolving Boc-Asp(OBzl)-OPac (17.7 g) in 8N-HCl/dioxane (100 ml), stirring the solution under ice cooling for 30 minutes, followed by concentration, and adding ether to precipitate crystals, which were collected by filtration and dried. After stirring at –15° C. for 30 minutes, the solution was brought to room temperature. After 30 minutes, the resulting insoluble material was separated by filtration, followed by concentration. The residue was dissolved in AcOEt, and the solution was washed with water, 10% aqueous citric acid and 4% aqueous $NaHCO_3$. After washing with water, the solution was dried with $Na_2SO_4$ and concentrated. Ether was added to the resulting residue to separate out a precipitate, which was collected by filtration.

Yield: 23.9 g (95.2%), Melting point: 73°–74° C., $Rf_1$: 0.40, $Rf_2$: 0.69 $[\alpha]_D^{28}$ –20.6° (c=1.05, in DMF)

Elemental analysis: As $C_{35}H_{37}N_3O_8$ Calculated: C, 66.97; H, 5.94; N, 6.69 Found: C, 67.21; H, 6.13; N, 6.71

(3) Production of Boc-D-Asp(OBzl)-Trp-Asp(OBzl)-OPac

8N-HCl/dioxane was added to Boc-Trp-Asp(OBzl)-OPac (50.2 g) to dissolve it, and the solution was stirred under ice cooling for 30 minutes, followed by concentration. Then, ether was added thereto to precipitate crystals, which were collected by filtration and dried. The crystals were dissolved in DMF (80 ml), and the solution was cooled with ice, followed by addition of TEA (22.3 ml). Boc-D-Asp(OBzl)-ONB [prepared from Boc-D-Asp(OBzl)-OH (28.5 g), HONB (17.2 g) and DCC (19.8 g)] was added thereto, and the mixture was stirred overnight. The resulting insoluble material was separated by filtration, followed by concentration. The residue was dissolved in AcOEt, and the solution was washed with water, 10% aqueous citric acid and 4% aqueous $NaHCO_3$. After washing with water, the solution was dried with $Na_2SO_4$ and concentrated. Ether was added to the resulting residue to separate out a precipitate, which was collected by filtration.

Yield: 60.3 g (90.5%), Melting point: 95°–97° C., $Rf_1$: 0.40, $Rf_2$: 0.70 $[\alpha]_D^{28}$ –5.2° (c=1.14, in DMF)

Elemental analysis: As $C_{46}H_{48}N_4O_{11}$ Calculated: C, 66.33; H, 5.81; N, 6.73 Found: C, 66.40; H, 5.93; N, 6.84

(4) Production of Boc-D-Trp-Asp(OBzl)-Trp-Asp(OBzl)-OPac

8N-HCl/dioxane was added to Boc-D-Asp(OBzl)-Trp-Asp(OBzl)-OPac (59.1 g) to dissolve it, and the solution was stirred under ice cooling for 40 minutes, followed by concentration. Then, ether was added thereto to precipitate crystals, which were collected by filtration and dried. The crystals were dissolved in DMF (70 ml), and the solution was cooled with ice, followed by addition of TEA (19.8 ml). Boc-D-Trp-ONB [prepared from Boc-D-Trp-OH (23.8 g), HONB (15.3 g) and DCC (17.6 g)] was added thereto, and the mixture was stirred overnight. The resulting insoluble material was separated by filtration, followed by concentration. The residue was dissolved in AcOEt, and the solution was washed with water, 10% aqueous citric acid and 4% aqueous $NaHCO_3$. After washing with water, the solution was dried with $Na_2SO_4$ and concentrated. Ether was added to the resulting residue to separate out a precipitate, which was collected by filtration.

Yield: 58.1 g (80.3%), Melting point: 139°–140° C., $Rf_1$: 0.38, $Rf_2$: 0.70 $[\alpha]_D^{28}$ –3.0° (c=1.29, in DMF)

Elemental analysis: As $C_{57}H_{58}N_6O_{12}$ Calculated: C, 67.18; H, 5.74; N, 8.25 Found: C, 67.28; H, 5.87; N, 8.34

(5) Production of Boc-Leu-D-Trp-D-Asp(OBzl)-Trp-Asp(OBzl)-OPac

8N-HCl/dioxane was added to Boc-D-Trp-D-Asp(OBzl)-Trp-Asp(OBzl)-OPac (20.4 g) to dissolve it, and the solution was stirred under ice cooling for 30 minutes, followed by concentration. Then, ether was added thereto to precipitate crystals, which were collected by filtration and dried. The crystals were dissolved in DMF (20 ml), and the solution was cooled with ice, followed by addition of TEA (5.6 ml). Boc-Leu-ONB [prepared from Boc-Leu-OH.$H_2O$ (5.48 g), HONB (4.30 g) and DCC (4.95 g)] was added thereto, and the mixture was stirred overnight. The resulting insoluble material was separated by filtration, followed by concentration. The residue was dissolved in AcOEt, and the solution was washed with water, 10% aqueous citric acid and 4% aqueous $NaHCO_3$. After washing with water, the solution was dried with $Na_2SO_4$ and concentrated. The resulting residue was recrystallized from ethyl acetate-petroleum ether.

Yield: 18.6 g (82.2%), Melting point: 119°–120° C., $Rf_1$: 0.39, $Rf_2$: 0.70 $[\alpha]_D^{28}$ –9.1° (c=0.98, in DMF)

Elemental analysis: As $C_{63}H_{69}N_7O_{13}$ Calculated: C, 66.83; H, 6.14; N, 8.66 Found: C, 66.80; H, 6.38; N, 8.75

(6) Production of Boc-D-tLeu-Leu-D-Trp-D-Asp(OBzl)-Trp-Asp(OBzl)-OPac

8N-HCl/dioxane was added to Boc-Leu-D-Trp-D-Asp(OBzl)-Trp-Asp(OBzl)-OPac (1.02 g) to dissolve it, and the solution was stirred under ice cooling for 15 minutes, followed by concentration. Then, ether was added thereto to precipitate crystals, which were collected by filtration and dried. The crystals were dissolved in DMF (5 ml), and the solution was cooled with ice, followed by addition of TEA (0.25 ml). Boc-D-tLeu-OH (0.23 g), HONB (0.15 g) and DCC (0.22 g)] were added thereto, and the mixture was stirred overnight. The resulting insoluble material was separated by filtration, followed by concentration. The residue was dissolved in AcOEt, and the solution was washed with water, 10% aqueous citric acid and 4% aqueous $NaHCO_3$. After washing with water, the solution was dried with $Na_2SO_4$ and concentrated. Ether was added to the resulting residue to separate out a precipitate, which was collected by filtration.

Yield: 1.08 g (96.4%), Melting point: 124°–126° C., $Rf_1$: 0.34, $Rf_2$: 0.71 $[\alpha]_D^{28}$ –6.1° (c=1.27, in DMF)

Elemental analysis: As $C_{69}H_{80}N_8O_{14}$ Calculated: C, 66.54; H, 6.47; N, 9.00 Found: C, 66.67; H, 6.60; N, 9.21

(7) Production of Boc-D-tLeu-Leu-D-Trp-D-Asp(OBzl)-Trp-Asp(OBzl)-OH

Boc-D-tLeu-Leu-D-Trp-D-Asp(OBzl)-Trp-Asp(OBzl)-OPac (0.75 g) was dissolved in 90% aqueous AcOH (10 ml), and Zn powder (1.96 g) was added thereto, followed by stirring for 3 hours. The Zn powder was removed by filtration, and filtrate was concentrated. AcOEt was added to the residue to dissolve it, and the solution was washed with 10% aqueous citric acid. After washing with water, the solution was dried with $Na_2SO_4$ and concentrated. Then, petroleum ether was added to the residue to separate out a precipitate, which was collected by filtration.

Yield: 0.66 g (97.6%), Melting point: 125°–127° C., Rf$_1$: 0.03, Rf$_2$: 0.67 [α]$_D^{25}$ −5.5° (c=1.19, in DMF)

Elemental analysis: As C$_{61}$H$_{74}$N$_8$O$_{13}$ Calculated: C, 64.99; H, 6.62; N, 9.94 Found: C, 65.11; H, 6.78; N, 10.01

(8) Production of cyclo[-D-Asp-Trp-Asp-D-tLeu-Leu-D-Trp-]

Boc-D-tLeu-Leu-Trp-D-Asp(OBzl)-Trp-Asp(OBzl)-OH (0.34 g) was dissolved in DCM (10 ml), and the solution was cooled with ice. HONB (0.11 g) and DCC (0.12 g) were added thereto, followed by stirring for 3 hours. Then, the resulting DCU was separated by filtration, followed by concentration, and ether was added to the residue to separate out a precipitate, which was collected by filtration. 8N-HCl/dioxane (10 ml) was added thereto under ice cooling to dissolve the precipitate. The resulting solution was stirred for 15 minutes and concentrated. Then, ether was added to the residue to separate out a precipitate, which was collected by filtration and dried. The precipitate was dissolved in DMF (6 ml), and the resulting solution was added dropwise to DMF (54 ml) containing TEA (0.42 ml) for 30 minutes, followed by stirring overnight and concentration. The residue was dissolved in AcOEt, and the solution was washed with 4% aqueous NaHCO$_3$. After washing with water, the solution was dried with Na$_2$SO$_4$ and concentrated. Then, ether-petroleum ether was added to the residue to separate out a precipitate, which was collected by filtration and dried. Of this precipitate, 101 mg was dissolved in DMF (15 ml) and catalytically reduced in a stream of hydrogen using palladium black as a catalyst. The catalyst was separated by filtration, and then the filtrate was concentrated. The resulting residue was dissolved in a small amount of AcOH, and thereafter, water was added thereto to conduct lyophilization. Finally, a part of the lyophilized product was purified by liquid chromatography using a YMC-D-ODS-5 column (2 cm×25 cm) (Y.M.C.) to obtain a desired material. The yield was 12.4 mg (42.8%).

Anal. for amino acids [110° C., hydrolysis for 24 hours; figures in parentheses show theoretical values.]: Asp 2.00(2); Leu 1.29(1) LSIMS (M+H$^+$)=829, (theoretical value)=829

EXAMPLE 54

Production of cyclo[-D-Asp-Trp-Asp-D-γMeLeu-Leu-D-Trp-]

(1) Production of Boc-D-γMeLeu-Leu-D-Trp-D-Asp(OBzl)-Trp-Asp(OBzl)-OPac

8N-HCl/dioxane was added to Boc-Leu-D-Trp-D-Asp(OBzl)-Trp-Asp(OBzl)-OPac (1.02 g) to dissolve it, and the solution was stirred under ice cooling for 15 minutes, followed by concentration. Then, ether was added thereto to precipitate crystals, which were collected by filtration and dried. The crystals were dissolved in DMF (5 ml), and the solution was cooled with ice, followed by addition of TEA (0.25 ml). Boc-D-γMeLeu-OH (0.24 g), HONB (0.15 g) and DCC (0.22 g)] were added thereto, and the mixture was stirred overnight. The resulting insoluble material was separated by filtration, followed by concentration. The residue was dissolved in AcOEt, and the solution was washed with water, 10% aqueous citric acid and 4% aqueous NaHCO$_3$. After washing with water, the solution was dried with Na$_2$SO$_4$ and concentrated. Ether was added to the resulting residue to separate out a precipitate, which was collected by filtration.

Yield: 1.11 g (98.0%), Melting point: 171°–172° C., Rf$_1$: 0.32, Rf$_2$: 0.70 [α]$_D^{28}$ −5.4° (c=1.12, in DMF)

Elemental analysis: As C$_{70}$H$_{82}$N$_8$O$_{14}$ Calculated: C, 66.76; H, 6.56; N, 8.90 Found: C, 66.88; H, 6.69; N, 9.09

(2) Production of Boc-D-γMeLeu-Leu-D-Trp-D-Asp(OBzl)-Trp-Asp(OBzl)-OH

Boc-D-γMeLeu-Leu-D-Trp-D-Asp(OBzl)-Trp-Asp(OBzl)-OPac (0.76 g) was dissolved in 90% aqueous AcOH (10 ml), and Zn powder (1.96 g) was added thereto, followed by stirring for 3 hours. The Zn powder was removed by filtration, and filtrate was concentrated. AcOEt was added to the residue to dissolve it, and the solution was washed with 10% aqueous citric acid. After washing with water, the solution was dried with Na$_2$SO$_4$ and concentrated. Then, petroleum ether was added to the residue to separate out a precipitate, which was collected by filtration.

Yield: 0.67 g (97.8%), Melting point: 115°–117° C., Rf$_1$: 0.03, Rf$_2$: 0.67 [α]$_D^{28}$ +6.3° (c=1.24, in DMF)

Elemental analysis: As C$_{62}$H$_{76}$N$_8$O$_{13}$ Calculated: C, 65.25; H, 6.71; N, 9.82 Found: C, 65.18; H, 6.87; N, 9.85

(3) Production of cyclo[-D-Asp-Trp-Asp-D-γMeLeu-Leu-D-Trp-]

Boc-D-γMeLeu-Leu-D-Trp-D-Asp(OBzl)-Trp-Asp(OBzl)-OH (0.34 g) was dissolved in DCM (10 ml), and the solution was cooled with ice. HONB (0.11 g) and DCC (0.12 g) were added thereto, followed by stirring for 3 hours. Then, the resulting DCU was separated by filtration, followed by concentration, and ether was added to the residue to separate out a precipitate, which was collected by filtration. 8N-HCl/dioxane (10 ml) was added thereto under ice cooling to dissolve the precipitate. The resulting solution was stirred for 15 minutes and concentrated. Then, ether was added to the residue to separate out a precipitate, which was collected by filtration and dried. The precipitate was dissolved in DMF (6 ml), and the resulting solution was added dropwise to DMF (54 ml) containing TEA (0.42 ml) for 30 minutes, followed by stirring overnight and concentration. The residue was dissolved in AcOEt, and the solution was washed with 4% aqueous NaHCO$_3$. After washing with water, the solution was dried with Na$_2$SO$_4$ and concentrated. Then, ether was added to the residue to separate out a precipitate, which was collected by filtration and dried. Of this precipitate, 102 mg was dissolved in DMF (15 ml) and catalytically reduced in a stream of hydrogen using palladium black as a catalyst. The catalyst was separated by filtration, and then the filtrate was concentrated. The resulting residue was dissolved in a small amount of AcOH, and thereafter, water was added thereto to conduct lyophilization. Finally, a part of the lyophilized product was purified by liquid chromatography using a YMC-D-ODS-5 column (2 cm×25 cm) (Y.M.C.) to obtain a desired material. The yield was 16.1 mg (51.5%).

Anal. for amino acids [110° C., hydrolysis for 24 hours; figures in parentheses show theoretical values.]: Asp 2.00(2); Leu 1.25(1) LSIMS (M+H$^+$)=843, (theoretical value)=843

EXAMPLE 55

Production of cyclo[-D-Asp-Trp-Asp-D-Thg(2)-Leu-D-Trp-]

(1) Production of Boc-D-Thg(2)-Leu-D-Trp-D-Asp(OBzl)-Trp-Asp(OBzl)-OPac

8N-HCl/dioxane was added to Boc-Leu-D-Trp-D-Asp(OBzl)-Trp-Asp(OBzl)-OPac (1.02 g) to dissolve it, and the solution was stirred under ice cooling for 15 minutes, followed by concentration. Then, ether was added thereto to precipitate crystals, which were collected by filtration and dried. The crystals were dissolved in DMF (5 ml), and the solution was cooled with ice, followed by addition of TEA (0.25 ml). Boc-D-Thg(2)-OH (0.19 g), HONB (0.15 g) and DCC (0.22 g)] were added thereto, and the mixture was stirred overnight. The resulting insoluble material was separated by filtration, followed by concentration. The residue was dissolved in AcOEt, and the solution was washed with water, 10% aqueous citric acid and 4% aqueous NaHCO$_3$. After washing with water, the solution was dried with Na$_2$SO$_4$ and concentrated. Ether was added to the resulting residue to separate out a precipitate, which was collected by filtration.

Yield: 1.04 g (90.9%), Melting point: 130°–132° C., Rf$_1$: 0.32, Rf$_2$: 0.68 [α]$_D^{28}$ −5.9° (c=0.95, in DMF)

Elemental analysis: As C$_{69}$H$_{74}$N$_8$O$_{14}$S Calculated: C, 65.18; H, 5.87; N, 8.81; S, 2.52 Found: C, 65.39; H, 5.99; N, 8.94; S, 2.46

(2) Production of Boc-D-Thg(2)-Leu-D-Trp-D-Asp(OBzl)-Trp-Asp(OBzl)-OH

Boc-D-Thg(2)-Leu-D-Trp-D-Asp(OBzl)-Trp-Asp(OBzl)-OPac (0.76 g) was dissolved in 90% aqueous AcOH (10 ml), and Zn powder (1.96 g) was added thereto, followed by stirring for 3 hours. The Zn powder was removed by filtration, and filtrate was concentrated. AcOEt was added to the residue to dissolve it, and the solution was washed with 10% aqueous citric acid. After washing with water, the solution was dried with Na$_2$SO$_4$ and concentrated. Then, petroleum ether was added to the residue to separate out a precipitate, which was collected by filtration.

Yield: 0.68 g (98.3%), Melting point: 167°–169° C., Rf$_1$: 0.03, Rf$_2$: 0.68 [α]$_D^{28}$ −5.3° (c=0.99, in DMF)

Elemental analysis: As C$_{61}$H$_{68}$N$_8$O$_{13}$S Calculated: C, 63.53; H, 5.94; N, 9.72; S, 2.78 Found: C, 63.42; H, 6.04; N, 9.90; S, 2.82

(3) Production of cyclo[-D-Asp-Trp-Asp-D-Thg(2)-Leu-D-Trp-]

Boc-D-Thg(2)-Leu-D-Trp-D-Asp(OBzl)-Trp-Asp(OBzl)-OH (0.35 g) was dissolved in DCM (10 ml), and the solution was cooled with ice. HONB (0.11 g) and DCC (0.12 g) were added thereto, followed by stirring for 3 hours. Then, the resulting DCU was separated by filtration, followed by concentration, and petroleum ether was added to the residue to separate out a precipitate, which was collected by filtration. 8N-HCl/dioxane (10 ml) was added thereto under ice cooling to dissolve the precipitate. The resulting solution was stirred for 15 minutes and concentrated. Then, ether was added to the residue to separate out a precipitate, which was collected by filtration and dried. The precipitate was dissolved in DMF (6 ml), and the resulting solution was added dropwise to DMF (54 ml) containing TEA (0.42 ml) for 30 minutes, followed by stirring overnight and concentration. The residue was dissolved in AcOEt, and the solution was washed with 4% aqueous NaHCO$_3$. After washing with water, the solution was dried with Na$_2$SO$_4$ and concentrated. The residue was purified using silica gel chromatography (1.5% methanol/DCM), and subsequently, ether was added thereto to separate out a precipitate, which was collected by filtration and dried. Of this precipitate, 104 mg was dissolved in DMF (15 ml) and catalytically reduced in a stream of hydrogen using palladium black as a catalyst. The catalyst was removed by filtration, and then the filtrate was concentrated. The resulting residue was dissolved in a small amount of AcOH, and thereafter, water was added thereto to conduct lyophilization. Finally, a part of the lyophilized product was purified by liquid chromatography using a YMC-D-ODS-5 column (2 cm×25 cm) to obtain a desired material. The yield was 11.7 mg (4.6%).

Anal. for amino acids [110° C., hydrolysis for 24 hours; figures in parentheses show theoretical values.]: Asp 2.00(2); Leu 1.30(1) LSIMS (M+H$^+$)=855, (theoretical value)=855

EXAMPLE 56

Production of cyclo[-D-Asp-Trp-Asp-Acbu-Leu-D-Trp-]

(1) Production of Boc-Acbu-Leu-D-Trp-D-Asp(OBzl)-Trp-Asp(OBzl)-OPac

8N-HCl/dioxane was added to Boc-Leu-D-Trp-D-Asp(OBzl)-Trp-Asp(OBzl)-OPac (1.02 g) to dissolve it, and the solution was stirred under ice cooling for 15 minutes, followed by concentration. Then, ether was added thereto to precipitate crystals, which were collected by filtration and dried. The crystals were dissolved in DMF (5 ml), and the solution was cooled with ice, followed by addition of TEA (0.25 ml). Boc-Acbu-OH (0.20 g), HONB (0.15 g) and DCC (0.22 g) were added thereto, and the mixture was stirred overnight. The resulting insoluble material was separated by filtration, followed by concentration. The residue was dissolved in AcOEt, and the solution was washed with water, 10% aqueous citric acid and 4% aqueous NaHCO$_3$. After washing with water, the solution was dried with Na$_2$SO$_4$ and concentrated. Ether was added to the resulting residue to separate out a precipitate, which was collected by filtration.

Yield: 1.06 g (94.0%), Melting point: 141°–143° C., Rf$_1$: 0.27, Rf$_2$: 0.67 [α]$_D^{28}$ −10.6° (c=1.27, in DMF)

Elemental analysis: As C$_{68}$H$_{76}$N$_8$O$_{14}$ Calculated: C, 66.43; H, 6.23; N, 9.11 Found: C, 66.42; H, 6.33; N, 9.30

(2) Production of Boc-Acbu-Leu-D-Trp-D-Asp(OBzl)-Trp-Asp(OBzl)-OH

Boc-Acbu-Leu-D-Trp-D-Asp(OBzl)-Trp-Asp(OBzl)-OPac (0.74 g) was dissolved in 90% aqueous AcOH (10 ml), and Zn powder (1.96 g) was added thereto, followed by stirring for 3 hours. The Zn powder was removed by filtration, and filtrate was concentrated. AcOEt was added to the residue to dissolve it, and the solution was washed with 10% aqueous citric acid. After washing with water, the solution was dried with Na$_2$SO$_4$ and concentrated. Then, petroleum ether was added to the residue to separate out a precipitate, which was collected by filtration.

Yield: 0.65 g (97.5%), Melting point: 114°–116° C., Rf$_1$: 0.03, Rf$_2$: 0.67 [α]$_D^{28}$ −12.50 (c=1.02, in DMF)

Elemental analysis: As C$_{60}$H$_{70}$N$_8$O$_{13}$ Calculated: C, 64.85; H, 6.35; N, 10.08 Found: C, 64.92; H, 6.42; N, 10.01

(3) Production of cyclo[-D-Asp-Trp-Asp-Acbu-Leu-D-Trp-]

Boc-Acbu-Leu-D-Trp-D-Asp(OBzl)-Trp-Asp(OBzl)-OH (0.33 g) was dissolved in DCM (10 ml), and the solution was cooled with ice. HONB (0.11 g) and DCC (0.12 g) were added thereto, followed by stirring for 3 hours. Then, the resulting DCU was separated by filtration, followed by concentration, and petroleum ether was added to the residue to separate out a precipitate, which was collected by filtration. 8N-HCl/dioxane (10 ml) was added thereto under ice cooling to dissolve the precipitate. The resulting solution was stirred for 15 minutes and concentrated. Then, ether was added to the residue to separate out a precipitate, which was collected by filtration and dried. The precipitate was dissolved in DMF (6 ml), and the resulting solution was added dropwise to DMF (54 ml) containing TEA (0.42 ml) for 30 minutes, followed by stirring overnight and concentration. The residue was dissolved in AcOEt, and the solution was washed with 4% aqueous NaHCO$_3$. After washing with water, the solution was dried with Na$_2$SO$_4$ and concentrated. Then, ether was added to the residue to separate out a precipitate, which was collected by filtration and dried. Of this precipitate, 99 mg was dissolved in DMF (15 ml) and catalytically reduced in a stream of hydrogen using palladium black as a catalyst. The catalyst was removed by filtration, and then the filtrate was concentrated. The resulting residue was dissolved in a small amount of AcOH, and thereafter, water was added thereto to conduct lyophilization. Finally, a part of the lyophilized product was purified by liquid chromatography using a YMC-D-ODS-5 column (2 cm×25 cm) to obtain a desired material. The yield was 2.2 mg (10.4%).

Anal. for amino acids [110° C., hydrolysis for 24 hours; figures in parentheses show theoretical values.]: Asp 2.00(2); Leu 1.23(1) LSIMS (M+H$^+$)=813, (theoretical value)=813

EXAMPLE 79

Production of cyclo[-D-Asp-Orn(COPh)-Asp-D-Leu-Leu-D-Trp-]

(1) Production of Boc-D-Asp(OBzl)-OPac

Boc-D-Asp(OBzl)-OH (25.0 g) was dissolved in methanol (50 ml), and Cs$_2$CO$_3$ (12.6 g) was added thereto little by little with stirring at room temperature. After Cs$_2$CO$_3$ was dissolved, the solvent was removed by distillation, and the residue was dissolved in DMF (500 ml). A DMF solution (50 ml) of phenacyl bromide (15.4 g) was added thereto dropwise with stirring under ice cooling, further followed by stirring at room temperature for 1 hour. Precipitated CsBr was removed by filtration, and the solvent was removed by distillation. The residue was dissolved in AcOEt, and the solution was washed successively with 5% aqueous NaHCO$_3$, 10% aqueous citric acid and a saturated aqueous solution of sodium chloride. After drying with Na$_2$SO$_4$, the solvent was removed by distillation, and the residue was recrystallized from ethyl acetate-petroleum ether.

Yield: 31.8 g (93.2%), Melting point: 74.0°–75.0° C., Rf$_1$: 0.73, Rf$_2$: 0.86 [α]$_D^{25}$ 21.9° (c=1.00, in DMF)

Elemental analysis: As C$_{24}$H$_{27}$NO$_7$ Calculated: C, 65.29; H, 6.16; N, 3.17 Found: C, 65.03; H, 6.19; N, 3.14

(2) Production of Boc-D-Trp-D-Asp(OBzl)-OPac

Boc-D-Asp(OBzl)-OPac (26.5 g) was dissolved in dioxane (50 ml), and 10N-HCl/dioxane (28.6 ml) was added thereto under ice cooling, followed by stirring under ice cooling for 30 minutes. The solvent was removed by distillation at room temperature, and ether was added to the residue to form a precipitate, which was collected by filtration, thereby obtaining H-D-Asp(OBzl)-OPac hydrochloride.

Boc-D-Trp-OH (18.3 g) was dissolved in distilled THF (150 ml), and N-methylmorpholine was added thereto with stirring at room temperature. After the atmosphere was replaced with nitrogen, isobutyl chloroformate (7.88 ml) was slowly added dropwise thereto with stirring at −15° C., and stirring was further continued at −15° C. for 15 minutes, thereby obtaining mixed acid anhydrides. An amine component [prepared by dissolving H-D-Asp(OBzl)-OPac hydrochloride in DMF (100 ml) and adding N-methylmorpholine (6.62 ml) thereto with stirring at −15° C. for neutralization] was added thereto little by little with stirring at −15° C., and the mixture was further stirred at room temperature for 1 hour. The solvent was removed by distillation, and the residue was dissolved in AcOEt. The solution was washed successively with 5% aqueous NaHCO$_3$, 10% aqueous citric acid and a saturated aqueous solution of sodium chloride. After drying with Na$_2$SO$_4$, the solvent was removed by distillation, and the residue was recrystallized from ethyl acetate-petroleum ether.

Yield: 36.1 g (96.0%), Melting point: 75.0°–76.0° C., Rf$_1$: 0.34, Rf$_2$: 0.73 [α]$_D^{25}$ 19.1° (c=1.00, in DMF)

Elemental analysis: As C$_{35}$H$_{37}$N$_3$O$_8$ Calculated: C, 66.97; H, 5.94; N, 6.69 Found: C, 67.19; H, 6.20; N, 6.44

(3) Production of Boc-Leu-D-Trp-D-Asp(OBzl)-OPac

Boc-D-Trp-D-Asp(OBzl)-OPac (34.5 g) was dissolved in dioxane (50 ml), and 10N-HCl/dioxane (100 ml) was added thereto under ice cooling, followed by stirring under ice cooling for 30 minutes. The solvent was removed by distillation at room temperature, and ether was added to the residue to separate out a precipitate, which was collected by filtration. The resulting precipitate was dissolved in DMF (350 ml), and TEA was added thereto with stirring under ice cooling to neutralize it. A DMF solution (50 ml) of Boc-Leu-ONB prepared from Boc-Leu-OH (15.3 g), HONB (13.8 g) and DCC (17.0 g) was further added thereto, followed by stirring overnight at room temperature. The solvent was removed by distillation, and the residue was dissolved in AcOEt. N,N-Dimethylpropanediamine (2.5 ml) was added thereto, followed by stirring at room temperature for 30 minutes. The mixture was washed successively with 5% aqueous NaHCO$_3$, 10% aqueous citric acid and a saturated aqueous solution of sodium chloride. After drying with Na$_2$SO$_4$, the solvent was removed by distillation, and then, ether-petroleum ether was added to the residue to separate out a precipitate, which was collected by filtration.

Yield: 37.49 g (92.0%), Melting point: 72°–74° C., Rf$_1$: 0.28, Rf$_2$: 0.71 [α]$_D^{25}$ 28.3° (c=1.00, in DMF)

Elemental analysis: As C$_{41}$H$_{48}$N$_4$O$_9$ Calculated: C, 66.47; H, 6.53; N, 7.56 Found: C, 66.25; H, 6.68; N, 7.56

(4) Production of Boc-D-Leu-Leu-D-Trp-D-Asp(OBzl)-OPac

Boc-Leu-D-Trp-D-Asp(OBzl)-OPac (29.6 g) was dissolved in dioxane (40 ml), and 10N-HCl/dioxane (100 ml) was added thereto under ice cooling, followed by stirring under ice cooling for 30 minutes. The solvent was removed by distillation at room temperature, and ether was added to the residue to separate out a precipitate, which was collected by filtration. The resulting precipitate was dissolved in DMF (300 ml), and TEA was added thereto with stirring under ice cooling to neutralize it. A DMF solution (40 ml) of Boc-D-Leu-ONB prepared from Boc-D-Leu-OH.H$_2$O (11.0 g), HONB (8.60 g) and DCC (10.7 g) was further added thereto, followed by stirring overnight at room temperature. The solvent was removed by distillation, and the residue was dissolved in AcOEt. N,N-Dimethylpropanediamine (1.26 ml) was added thereto, followed by stirring at room temperature for 30 minutes. The mixture was washed successively with 5% aqueous NaHCO$_3$, 10% aqueous citric acid and a saturated aqueous solution of sodium chloride. After drying with Na$_2$SO$_4$, the solvent was removed by distillation, and then, ether-petroleum ether was added to the residue to separate out a precipitate, which was collected by filtration.

Yield: 30.9 g (90.5%), Melting point: 79°–80° C., Rf$_1$: 0.26, Rf$_2$: 0.73 [α]$_D^{25}$ 27.4° (c=1.00, in DMF)

Elemental analysis: As C$_{47}$H$_{59}$N$_5$O$_{10}$ Calculated: C, 66.10; H, 6.96; N, 8.20 Found: C, 66.11; H, 7.05; N, 8.05

(5) Production of Boc-Asp(OBzl)-D-Leu-Leu-D-Trp-D-Asp(OBzl)-OPac

Boc-D-Leu-Leu-D-Trp-D-Asp(OBzl)-OPac (17.1 g) was dissolved in dioxane (10 ml), and 10-N HCl/dioxane (50 ml) was added thereto under ice cooling, followed by stirring under ice cooling for 30 minutes. The solvent was removed by distillation at room temperature, and ether was added to the residue to separate out a precipitate, which was collected by filtration. The resulting precipitate was dissolved in DMF (100 ml), and TEA was added thereto with stirring under ice cooling to neutralize it. A DMF solution (20 ml) of Boc-Asp(OBzl)-ONB prepared from Boc-Asp(OBzl)-OH (7.76 g), HONB (5.02 g) and DCC (6.19 g) was further added thereto, followed by stirring overnight at room temperature. The solvent was removed by distillation, and the residue was dissolved in AcOEt. N,N-Dimethylpropanediamine (0.63 ml) was added thereto, followed by stirring at room temperature for 30 minutes. The mixture was washed successively with 5% aqueous NaHCO₃, 10% aqueous citric acid and a saturated aqueous solution of sodium chloride. After drying with Na₂SO₄, the solvent was removed by distillation, and then, ether-petroleum ether was added to the residue to separate out a precipitate, which was collected by filtration. The precipitate was recrystallized from ethyl acetate-petroleum ether.

Yield: 16.5 g (82.5%), Melting point: 178°–179° C., Rf₁: 0.28, Rf₂: 0.76 [α]$_D^{25}$ 13.0° (c=1.00, in DMF)

Elemental analysis: As C₅₈H₇₀N₆O₁₃ Calculated: C, 65.77; H, 6.66; N, 7.93 Found: C, 65.49; H, 6.69; N, 8.02

(6) Production of Boc-Orn(COPh)-OH.DCHA

Boc-Orn-OH (0.51 g) [obtained by catalytically reducing Boc-Orn(Z)-OH in methanol in a stream of hydrogen using 10% Pd-carbon as a catalyst] was dissolved in DMF, and the solution was cooled with ice. TEA (0.61 ml) and PhCOONB [prepared from PhCOOH (0.30 g), HONB (0.47 g) and DCC (0.54 g)] were added thereto, followed by stirring overnight. The reaction solution was concentrated, and the residue was dissolved in AcOEt. The resulting solution was washed with 10% aqueous citric acid. After washing with water, the solution was dried with Na₂SO₄ and concentrated. Then, ether and dicyclohexylamine (438 μl) were added to the residue to separate out a precipitate, which was collected by filtration.

Yield: 1.01 g (97.6%), Melting point: 148°–150° C. [α]$_D^{28}$ +9.6° (c=0.90, in methanol)

Elemental analysis: As C₂₉H₄₇N₃O₅ Calculated: C, 67.28; H, 9.15; N, 8.12 Found: C, 67.35; H, 8.99; N, 8.03

(7) Production of Boc-Orn(COPh)-Asp(OBzl)-D-Leu-Leu-D-Trp-D-Asp(OBzl)-OPac

Boc-Asp(OBzl)-D-Leu-Leu-D-Trp-D-Asp(OBzl)-OPac (0.85 g) obtained in (5) described above was dissolved in 8N-HCl/dioxane (15 ml), and the solution was stirred under ice cooling for 10 minutes, followed by concentration. Then, ether was added thereto to precipitate crystals, which were collected by filtration and dried. The crystals were dissolved in DMF (15 ml), and the solution was cooled with ice, followed by addition of TEA (0.22 ml). Boc-Orn(COPh)-ONB [prepared from Boc-Orn(COPh)-OH (0.30 g), HONB (0.18 g) and DCC (0.21 g)] was added thereto, and the mixture was stirred overnight. The resulting insoluble material was separated by filtration, followed by concentration. The residue was dissolved in AcOEt, and the solution was washed with water, 10% aqueous citric acid and 4% aqueous NaHCO₃. After washing with water, the solution was dried with Na₂SO₄ and concentrated. Ether was added to the resulting residue to separate out a precipitate, which was collected by filtration.

Yield: 0.97 g (94.9%), Melting point: 107°–109° C., Rf₁: 0.28, Rf₂: 0.64 [α]$_D^{28}$ +8.2° (c=1.23, in DMF)

Elemental analysis: As C₇₀H₈₄N₈O₁₅ Calculated: C, 65.81; H, 6.63; N, 8.77 Found: C, 65.76; H, 6.76; N, 8.93

(8) Production of Boc-Orn(COPh)-Asp(OBzl)-D-Leu-Leu-D-Trp-D-Asp(OBzl)-OH

Boc-Orn(COPh)-Asp(OBzl)-D-Leu-Leu-D-Trp-D-Asp(OBzl)-OPac (0.77 g) was dissolved in 90% aqueous AcOH (20 ml), and Zn powder (1.96 g) was added thereto, followed by stirring for 3 hours. The Zn powder was removed by filtration, and filtrate was concentrated. AcOEt was added to the residue to dissolve it, and the solution was washed with 10% aqueous citric acid. After washing with water, the solution was dried with Na₂SO₄ and concentrated. Then, petroleum ether was added to the residue to separate out a precipitate, which was collected by filtration.

Yield: 0.68 g (97.8%), Melting point: 113°–115° C., Rf₁: 0.02, Rf₂: 0.63 [α]$_D^{28}$ +9.8° (c=1.10, in DMF)

Elemental analysis: As C₆₂H₇₈N₈O₁₄ Calculated: C, 64.23; H, 6.78; N, 9.67 Found: C, 64.11; H, 6.90; N, 9.52

(9) Production of cyclo[-D-Asp-Orn(COPh)-Asp-D-Leu-Leu-D-Trp-]

Boc-Orn(COPh)-Asp(OBzl)-D-Leu-Leu-D-Trp-D-Asp(OBzl)-OH (0.35 g) was dissolved in DCM (20 ml), and the solution was cooled with ice. HONB (0.11 g) and DCC (0.12 g) were added thereto, followed by stirring for 3 hours, Then, the resulting DCU was separated by filtration, followed by concentration, and ether was added to the residue to separate out a precipitate, which was collected by filtration. 8N-HCl/dioxane (20 ml) was added thereto under ice cooling to dissolve the precipitate. The resulting solution was stirred for 10 minutes and concentrated. Then, ether was added to the residue to separate out a precipitate, which was collected by filtration and dried. The precipitate was dissolved in DMF (6 ml), and the resulting solution was added dropwise to DMF (54 ml) containing TEA (0.42 ml) for 30 minutes, followed by stirring overnight and concentration. The residue was dissolved in AcOEt, and the solution was washed with 4% aqueous NaHCO₃. After washing with water, the solution was dried with Na₂SO₄ and concentrated. Then, ether-petroleum ether was added to the residue to separate out a precipitate, which was collected by filtration and dried. Of this precipitate, 104 mg was dissolved in DMF (15 ml) and catalytically reduced in a stream of hydrogen using palladium black as a catalyst. The catalyst was removed by filtration, and then the filtrate was concentrated. The resulting residue was dissolved in a small amount of AcOH, and thereafter, water was added thereto to conduct lyophilization. Finally, a part of the lyophilized product was purified by liquid chromatography using a YMC-D-ODS-5 column (2 cm×25 cm) (Y.M.C.) to obtain a desired material. The yield was 11.1 mg (48.1%).

Anal. for amino acids [6N-HCl, 110° C., hydrolysis for 24 hours; figures in parentheses show theoretical values.]: Asp 2.00(2); Leu 2.19(2); Orn 1.09(1) LSIMS (M+H⁺)=861, (theoretical value)=861

EXAMPLE 80

Production of cyclo[-D-Asp-Orn(COCH₂Ph)-AsP-D-Leu-Leu-D-Trp-]

(1) Production of Boc-Orn(COCH₂Ph)-OH.CHA

Boc-Orn-OH (0.51 g) was dissolved in DMF, and the solution was cooled with ice. TEA (1.53 ml) and PhCH₂COCl (367 μl) was added thereto, and stirred for 2 hours. The reaction solution was concentrated, and the residue was dissolved in AcOEt. The resulting solution was washed with 10% aqueous citric acid. After washing with water, the solution was dried with Na₂SO₄ and concentrated. Then, ether and cyclohexylamine (254 μl) were added to the residue to separate out a precipitate, which was collected by filtration.

Yield: 0.52 g (57.9%), Melting point: 137°–139° C. [α]$_D^{28}$ +2.4° (c=0.50, in methanol)

Elemental analysis: As C₂₄H₃₉N₃O₅ Calculated: C, 64.12; H, 8.74; N, 9.35 Found: C, 64.05; H, 8.92; N, 9.39

(2) Production of Boc-Orn(COCH₂Ph)-Asp(OBzl)-D-Leu-Leu-D-Trp-D-Asp(OBzl)-OPac

Boc-Asp(OBzl)-D-Leu-Leu-D-Trp-D-Asp(OBzl)-OPac (0.85 g) prepared in EXAMPLE 79 (5) was dissolved in 8N-HCl/dioxane (15 ml), and the solution was stirred under ice cooling for 10 minutes, followed by concentration. Then, ether was added thereto to precipitate crystals, which were collected by filtration and dried. The crystals were dissolved in DMF (15 ml), and the solution was cooled with ice, followed by addition of TEA (0.22 ml). Boc-Orn(COCH$_2$Ph)-ONB [prepared from Boc-Orn(COCH$_2$Ph)-OH (0.32 g), HONB (0.18 g) and DCC (0.21 g)] was added thereto, and the mixture was stirred overnight. The resulting insoluble material was separated by filtration, followed by concentration. The residue was dissolved in AcOEt, and the solution was washed with water, 10% aqueous citric acid and 4% aqueous NaHCO$_3$. After washing with water, the solution was dried with Na$_2$SO$_4$ and concentrated. Ether was added to the resulting residue to separate out a precipitate, which was collected by filtration.

Yield: 0.81 g (78.4%), Melting point: 148°–150° C., Rf$_1$: 0.34, Rf$_2$: 0.65 $[\alpha]_D^{28}$ 14.1° (c=1.13, in DMF)

Elemental analysis: As C$_{71}$H$_{86}$N$_8$O$_{15}$ Calculated: C, 66.03; H, 6.71; N, 8.68 Found: C, 66.14; H, 6.67; N, 8.51

(3) Production of Boc-Orn(COCH$_2$Ph)-Asp(OBzl)-D-Leu-Leu-D-Trp-D-Asp(OBzl)-OH

Boc-Orn(COCH$_2$Ph)-Asp(OBzl)-D-Leu-Leu-D-Trp-D-Asp(OBzl)-OPac (0.65 g) was dissolved in 90% aqueous AcOH (20 ml), and Zn powder (1.63 g) was added thereto, followed by stirring for 3 hours. The Zn powder was removed by filtration, and filtrate was concentrated. AcOEt was added to the residue to dissolve it, and the solution was washed with 10% aqueous citric acid. After washing with water, the solution was dried with Na$_2$SO$_4$ and concentrated. Then, petroleum ether was added to the residue to separate out a precipitate, which was collected by filtration.

Yield: 0.57 g (97.2%), Melting point: 120°–122° C., Rf$_1$: 0.03, Rf$_2$: 0.64 $[\alpha]_D^{28}$ +16.9° (c=0.91, in DMF)

Elemental analysis: As C$_{63}$H$_{80}$N$_8$O$_{14}$ Calculated: C, 64.49; H, 6.87; N, 9.55 Found: C, 64.60; H, 6.79; N, 9.36

(4) Production of cyclo[-D-Asp-Orn(COCH$_2$Ph)-Asp-D-Leu-Leu-D-Trp-]

Boc-Orn(COCH$_2$Ph)-Asp(OBzl)-D-Leu-Leu-D-Trp-D-Asp(OBzl)-OH (0.35 g) was dissolved in DCM (20 ml), and the solution was cooled with ice. HONB (0.11 g) and DCC (0.12 g) were added thereto, followed by stirring for 3 hours. Then, the resulting DCU was separated by filtration, followed by concentration, and ether was added to the residue to separate out a precipitate, which was collected by filtration. 8N HCl/dioxane (20 ml) was added thereto under ice cooling to dissolve the precipitate. The resulting solution was stirred for 10 minutes and concentrated. Then, ether was added to the residue to separate out a precipitate, which was collected by filtration and dried. The precipitate was dissolved in DMF (10 ml), and the resulting solution was added dropwise to DMF (54 ml) containing TEA (0.42 ml) for 30 minutes, followed by stirring overnight and concentration. The residue was dissolved in AcOEt, and the solution was washed with 4% aqueous NaHCO$_3$. After washing with water, the solution was dried with Na$_2$SO$_4$ and concentrated. Then, ether-petroleum ether was added to the residue to separate out a precipitate, which was collected by filtration and dried. Of this precipitate, 106 mg was dissolved in DMF (15 ml) and catalytically reduced in a stream of hydrogen using palladium black as a catalyst. The catalyst was removed by filtration, and then the filtrate was concentrated. The resulting residue was dissolved in a small amount of AcOH, and thereafter, water was added thereto to conduct lyophilization. Finally, a part of the lyophilized product was purified by liquid chromatography using a YMC-D-ODS-5 column (2 cm×25 cm) (Y.M.C.) to obtain a desired material. The yield was 2.3 mg (2.9%).

Anal. for amino acids [6N-HCl, 110° C., hydrolysis for 24 hours; figures in parentheses show theoretical values.]: Asp 2.00(2); Leu 2.29(2); Orn 1.10(1) LSIMS (M+H$^+$)=876, (theoretical value)=876

EXAMPLE 81

Production of cyclo[-D-Asp-Orn(COCH$_2$CH$_2$Ph)-Asp-D-Leu-Leu-D-Trp-]

(1) Production of Boc-Orn(COCH$_2$CH$_2$Ph)-OH.DCHA

Boc-Orn-OH (0.51 g) was dissolved in DMF, and the solution was cooled with ice. TEA (0.61 ml) and PhCH$_2$CH$_2$COONB [prepared from PhCH$_2$CH$_2$COOH (0.36 g), HONB (0.47 g) and DCC (0.54 g)] was added thereto, and stirred overnight. The reaction solution was concentrated, and the residue was dissolved in AcOEt. The resulting solution was washed with 10% aqueous citric acid. After washing with water, the solution was dried with Na$_2$SO$_4$ and concentrated. Then, ether and dicyclohexylamine (438 µl) were added to the residue to separate out a precipitate, which was collected by filtration.

Yield: 0.72 g (66.1%), Melting point: 131°–133° C. $[\alpha]_D^{28}$ +6.9° (c=0.86, in methanol)

Elemental analysis: As C$_{31}$H$_{51}$N$_3$O$_5$ Calculated: C, 68.22; H, 9.42; N, 7.70 Found: C, 68.29; H, 9.22; N, 7.62

(2) Production of Boc-Orn(COCH$_2$CH$_2$Ph)-Asp(OBzl)-D-Leu-Leu-D-Trp-D-Asp(OBzl)-OPac Boc-Asp(OBzl)-D-Leu-Leu-D-Trp-D-Asp(OBzl)-OPac (0.85 g) prepared in EXAMPLE 79 (5) was dissolved in 8N-HCl/dioxane (15 ml), and the solution was stirred under ice cooling for 10 minutes, followed by concentration. Then, ether was added thereto to precipitate crystals, which were collected by filtration and dried. The crystals were dissolved in DMF (15 ml), and the solution was cooled with ice, followed by addition of TEA (0.22 ml). Boc-Orn(COCH$_2$CH$_2$Ph)-ONB [prepared from Boc-Orn(COCH$_2$CH$_2$Ph)-OH (0.33 g), HONB (0.18 g) and DCC (0.21 g)] was added thereto, and the mixture was stirred overnight. The resulting insoluble material was separated by filtration, followed by concentration. The residue was dissolved in AcOEt, and the solution was washed with water, 10% aqueous citric acid and 4% aqueous NaHCO$_3$. After washing with water, the solution was dried with Na$_2$SO$_4$ and concentrated. Ether was added to the resulting residue to separate out a precipitate, which was collected by filtration.

Yield: 0.95 g (91.0%), Melting point: 110°–112° C., Rf$_1$: 0.23, Rf$_2$: 0.65 $[\alpha]_D^{28}$ +9.0° (c=0.98, in DMF)

Elemental analysis: As C$_{72}$H$_{88}$N$_8$O$_{15}$ Calculated: C, 66.24; H, 6.79; N, 8.58 Found: C, 66.07; H, 6.90; N, 8.75

(3) Production of Boc-Orn(COCH$_2$CH$_2$Ph)-Asp(OBzl)-D-Leu-Leu-D-Trp-D-Asp(OBzl)-OH Boc-Orn(COCH$_2$CH$_2$Ph)-Asp(OBzl)-D-Leu-Leu-D-Trp-D-Asp(OBzl)-OPac (0.78 g) was dissolved in 90% aqueous AcOH (20 ml), and Zn powder (1.96 g) was added thereto, followed by stirring for 3 hours. The Zn powder was removed by filtration, and filtrate was concentrated. AcOEt was added to the residue to dissolve it, and the solution was washed with 10% aqueous citric acid. After washing with water, the solution was dried with Na$_2$SO$_4$ and concentrated. Then, petroleum ether was added to the residue to separate out a precipitate, which was collected by filtration.

Yield: 0.70 g (98.3%), Melting point: 105°–108° C., Rf$_1$: 0.02, Rf$_2$: 0.64 $[\alpha]_D^{28}$ +10.4° (c=1.20, in DMF)

Elemental analysis: As C$_{64}$H$_{82}$N$_8$O$_{14}$ Calculated: C, 64.74; H, 6.96; N, 9.44 Found: C, 64.60; H, 7.07; N, 9.64

(4) Production of cyclo[-D-Asp-Orn(COCH$_2$CH$_2$Ph)-Asp-D-Leu-Leu-D-Trp-]

Boc-Orn(COCH$_2$CH$_2$Ph)-Asp(OBzl)-D-Leu-Leu-D-Trp-D-Asp(OBzl)-OH (0.36 g) was dissolved in DCM (20 ml), and the solution was cooled with ice. HONB (0.11 g) and DCC (0.12 g) were added thereto, followed by stirring for 3 hours. Then, the resulting DCU was separated by filtration, followed by concentration, and ether was added to the residue to separate out a precipitate, which was collected by filtration. 8N-HCl/dioxane (20 ml) was added thereto under ice cooling to dissolve the precipitate. The resulting solution was stirred for 10 minutes and concentrated. Then, ether was added to the residue to separate out a precipitate, which was collected by filtration and dried. The precipitate was dissolved in DMF (6 ml), and the resulting solution was added dropwise to DMF (54 ml) containing TEA (0.42 ml) for 30 minutes, followed by stirring overnight and concentration. The residue was dissolved in AcOEt, and the solution was washed with 4% aqueous $NaHCO_3$. After washing with water, the solution was dried with $Na_2SO_4$ and concentrated. Then, ether-petroleum ether was added to the residue to separate out a precipitate, which was collected by filtration and dried. Of this precipitate, 107 mg was dissolved in DMF (15 ml) and catalytically reduced in a stream of hydrogen using palladium black as a catalyst. The catalyst was removed by filtration, and then the filtrate was concentrated. The resulting residue was dissolved in a small amount of AcOH, and thereafter, water was added thereto to conduct lyophilization. Finally, a part of the lyophilized product was purified by liquid chromatography using a YMC-D-ODS-5 column (2 cm×25 cm) (Y.M.C.) to obtain a desired material. The yield was 9.1 mg (40.9%).

Anal. for amino acids [6N-HCl, 110° C., hydrolysis for 24 hours; figures in parentheses show theoretical values.]: Asp 2.00(2); Leu 2.22(2); Orn 1.10(1) LSIMS (M+H$^+$)=889, (theoretical value)=889

EXAMPLE 82

Production of cyclo[-D-Asp-Orn($COCH_2$-Ind)-Asp-D-Leu-Leu-D-Trp-]

(1) Production of Boc-Orn($COCH_2$-Ind)-OH.DCHA

Boc-Orn-OH (0.51 g) was dissolved in DMF, and the solution was cooled with ice. TEA (0.61 ml) and Ind-$CH_2$COONB [prepared from Ind-$CH_2$COOH (0.42 g), HONB (0.47 g) and DCC (0.54 g)] was added thereto, and stirred overnight. The reaction solution was concentrated, and the residue was dissolved in AcOEt. The resulting solution was washed with 10% aqueous citric acid. After washing with water, the solution was dried with $Na_2SO_4$ and concentrated. Then, ether and cyclohexylamine (254 µl) were added to the residue to separate out a precipitate, which was collected by filtration.

Yield: 1.10 g (96.5%), Melting point: 95°–98° C. $[\alpha]_D^{28}$ +5.3° (c=0.92, in methanol)

Elemental analysis: As $C_{32}H_{50}N_4O_5$ Calculated: C, 67.34; H, 8.83; N, 9.82 Found: C, 67.25; H, 9.00; N, 9.93

(2) Production of Boc-Orn($COCH_2$-Ind)-AsP(OBzl)-D-Leu-Leu-D-Trp-D-Asp(OBzl)-OPac Boc-Asp(OBzl)-D-Leu-Leu-D-Trp-D-Asp(OBzl)-OPac (0.85 g) prepared in EXAMPLE 79 (5) was dissolved in 8N-HCl/dioxane (15 ml), and the solution was stirred under ice cooling for 10 minutes, followed by concentration. Then, ether was added thereto to precipitate crystals, which were collected by filtration and dried. The crystals were dissolved in DMF (15 ml), and the solution was cooled with ice, followed by addition of TEA (0.22 ml). Boc-Orn($COCH_2$-Ind)-ONB [prepared from Boc-Orn($COCH_2$-Ind)-OH (0.35 g), HONB (0.18 g) and DCC (0.21 g)] was added thereto, and the mixture was stirred overnight. The resulting insoluble material was separated by filtration, followed by concentration. The residue was dissolved in AcOEt, and the solution was washed with water, 10% aqueous citric acid and aqueous $NaHCO_3$. After washing with water, the solution was dried with $Na_2SO_4$ and concentrated. Ether was added to the resulting residue to separate out a precipitate, which was collected by filtration.

Yield: 0.93 g (87.4%), Melting point: 109°–111° C., Rf$_1$: 0.16, Rf$_2$: 0.64 $[\alpha]_D^{28}$ +9.7° (c=1.01, in DMF)

Elemental analysis: As $C_{73}H_{87}N_8O_{15}$ Calculated: C, 65.90; H, 6.59; N, 9.47 Found: C, 65.69; H, 6.89; N, 9.47

(3) Production of Boc-Orn($COCH_2$-Ind)-Asp(OBzl)-D-Leu-Leu-D-Trp-D-Asp(OBzl)-OH Boc-Orn($COCH_2$-Ind)-Asp(OBzl)-D-Leu-Leu-D-Trp-D-Asp(OBzl)-OPac (0.80 g) was dissolved in 90% aqueous AcOH (20 ml), and Zn powder (1.96 g) was added thereto, followed by stirring for 3 hours. The Zn powder was removed by filtration, and filtrate was concentrated. AcOEt was added to the residue to dissolve it, and the solution was washed with 10% aqueous citric acid. After washing with water, the solution was dried with $Na_2SO_4$ and concentrated. Then, petroleum ether was added to the residue to separate out a precipitate, which was collected by filtration.

Yield: 0.71 g (97.6%), Melting point: 96°–98° C., Rf$_1$: 0.02, Rf$_2$: 0.62 $[\alpha]_D^{28}$ +9.4° (c=1.01, in DMF)

Elemental analysis: As $C_{65}H_{81}N_9O_{14}$ Calculated: C, 64.39; H, 6.73; N, 10.40 Found: C, 64.51; H, 6.86; N, 10.36

(4) Production of cyclo[-D-Asp-Orn($COCH_2$-Ind)-Asp-D-Leu-Leu-D-Trp-]

Boc-Orn($COCH_2$-Ind)-Asp(OBzl)-D-Leu-Leu-D-Trp-D-Asp(OBzl)-OH (0.36 g) was dissolved in DCM (20 ml), and the solution was cooled with ice. HONB (0.11 g) and DCC (0.12 g) were added thereto, followed by stirring for 3 hours. Then, the resulting DCU was separated by filtration, followed by concentration, and ether was added to the residue to separate out a precipitate, which was collected by filtration. 8N-HCl/dioxane (20 ml) was added thereto under ice cooling to dissolve the precipitate. The resulting solution was stirred for 10 minutes and concentrated. Then, ether was added to the residue to separate out a precipitate, which was collected by filtration and dried. The precipitate was dissolved in DMF (6 ml), and the resulting solution was added dropwise to DMF (54 ml) containing TEA (0.42 ml) for 30 minutes, followed by stirring overnight and concentration. The residue was dissolved in AcOEt, and the solution was washed with 4% aqueous $NaHCO_3$. After washing with water, the solution was dried with $Na_2SO_4$ and concentrated. Then, ether-petroleum ether was added to the residue to separate out a precipitate, which was collected by filtration and dried. Of this precipitate, 109 mg was dissolved in DMF (15 ml) and catalytically reduced in a stream of hydrogen using palladium black as a catalyst. The catalyst was removed by filtration, and then the filtrate was concentrated. The resulting residue was dissolved in a small amount of AcOH, and thereafter, water was added thereto to conduct lyophilization. Finally, a part of the lyophilized product was purified by liquid chromatography using a YMC-D-ODS-5 column (2 cm×25 cm) to obtain a desired material. The yield was 4.1 mg (12.5%).

Anal. for amino acids [6N-HCl, 110° C., hydrolysis for 24 hours; figures in parentheses show theoretical values.]: Asp 2.00(2); Leu 2.25(2); Orn 1.08(1) LSIMS (M+H$^+$)=915, (theoretical value)=915

EXAMPLE 88

Production of cyclo[-D-Asp-Hyp(Bzl)-Asp-D-Thg(2)-Leu-D-Trp-]

(1) Production of Boc-D-Asp(OBzl)-Hyp(Bzl)-Asp(OBzl)-OPac

8N-HCl/dioxane was added to Boc-Hyp(Bzl)-Asp(OBzl)-OPac (3.77 g) prepared in accordance with the processes described in EXAMPLE 53 (1) and (2) to dissolve it, and the solution was stirred under ice cooling for 30 minutes, followed by concentration. 4% aqueous $NaHCO_3$ was added thereto to adjust the pH to 9–10, and then, extraction was conducted using AcOEt. The extract was dried with $Na_2SO_4$, concentrated and dried. The resulting product was dissolved in DMF (40 ml) and cooled with ice. Then, TEA (0.84 ml) was added thereto. Boc-D-Asp(OBzl)-ONB [prepared from Boc-D-Asp(OBzl)-OH (2.16 g), HONB (1.31 g) and DCC (1.51 g)] was added thereto, followed by stirring overnight. The resulting insoluble material was separated by filtration, followed by concentration. The residue was dissolved in AcOEt, and the solution was washed with water, 10% aqueous citric acid and 4% aqueous $NaHCO_3$. After washing with water, the solution was dried with $Na_2SO_4$ and concentrated. The residue was purified using silica gel chromatography (1% methanol/DCM) and subsequently concentrated. The yield was 2.22 g (57.4%).

(2) Production of Boc-D-Trp-D-Asp(OBzl)-Hyp(Bzl)-Asp(OBzl)-OPac

8N-HCl/dioxane was added to Boc-D-Asp(OBzl)-Hyp(Bzl)-Asp(OBzl)-OPac (1.67 g) to dissolve it, and the solution was stirred under ice cooling for 10 minutes, followed by concentration. 4% aqueous $NaHCO_3$ was added thereto to adjust the pH to 9–10, and then, extraction was conducted using AcOEt. The extract was dried with $Na_2SO_4$, concentrated and dried. The resulting product was dissolved in DMF (20 ml) and cooled with ice. Then, TEA (0.28 ml) was added thereto. Boc-D-Trp-ONB [prepared from Boc-D-Trp-OH (0.67 g), HONB (0.43 g) and DCC (0.50 g)] was added thereto, followed by stirring overnight. The resulting insoluble material was separated by filtration, followed by concentration. The residue was dissolved in AcOEt, and the solution was washed with water, 10% aqueous citric acid and 4% aqueous $NaHCO_3$. After washing with water, the solution was dried with $Na_2SO_4$ and concentrated. Then, ether-petroleum ether was added to the residue to separate out a precipitate, which was collected by filtration.

Yield: 2.05 g (98.9%), Melting point: 76°–78° C., $Rf_1$: 0.48, $Rf_2$: 0.72 $[\alpha]_D^{28}$ +9.2° (c=1.13, in DMF)

Elemental analysis: As $C_{58}H_{61}N_5O_{13}$ Calculated: C, 67.23; H, 5.93; N, 6.76 Found: C, 67.04; H, 6.14; N, 6.79

(3) Production of Boc-Leu-D-Trp-D-Asp(OBzl)-Hyp(Bzl)-Asp(OBzl)-OPac

8-N HCl/dioxane was added to Boc-D-Trp-D-Asp(OBzl)-Hyp(Bzl)-Asp(OBzl)-OPac (1.04 g) to dissolve it, and the solution was stirred under ice cooling for 10 minutes, followed by concentration. Then, ether was added to the residue to separate out a precipitate, which was collected by filtration and dried. The resulting product was dissolved in DMF (15 ml) and cooled with ice. Then, TEA (0.28 ml) was added thereto. Boc-Leu-ONB [prepared from Boc-Leu-OH.$H_2O$ (0.27 g), HONB (0.22 g) and DCC (0.25 g)] was added thereto, followed by stirring for 3 hours. The resulting insoluble material was separated by filtration, followed by concentration. The residue was dissolved in AcOEt, and the solution was washed with water, 10% aqueous citric acid and 4% aqueous $NaHCO_3$. After washing with water, the solution was dried with $Na_2SO_4$ and concentrated. Then, ether-petroleum ether was added to the residue to separate out a precipitate, which was collected by filtration.

Yield: 1.09 g (94.8%), Melting point: 88°–90° C., $Rf_1$: 0.50, $Rf_2$: 0.71 $[\alpha]_D^{28}$ +0.6° (c=0.88, in DMF)

Elemental analysis: As $C_{64}H_{72}N_6O_{14}$ Calculated: C, 66.88; H, 6.31; N, 7.31 Found: C, 66.91; H, 6.61; N, 7.51

(4) Production of Boc-D-Thg(2)-Leu-D-Trp-D-Asp(OBzl)-Hyp(Bzl)-Asp(OBzl)-OPac

8N-HCl/dioxane was added to Boc-Leu-D-Trp-D-Asp(OBzl)-Hyp(Bzl)-Asp(OBzl)-OPac (0.92 g) to dissolve it, and the solution was stirred under ice cooling for 15 minutes, followed by concentration. Then, ether was added to the residue to separate out a precipitate, which was collected by filtration and dried. The resulting product was dissolved in DMF (10 ml) and cooled with ice. Then, TEA (0.22 ml) was added thereto. Boc-D-Thg(2)-OH (0.23 g), HONB (0.13 g) and DCC (0.20 g) were added thereto, followed by stirring for 3 hours. The resulting insoluble material was separated by filtration, followed by concentration. The residue was dissolved in AcOEt, and the solution was washed with water, 10% aqueous citric acid and 4% aqueous $NaHCO_3$. After washing with water, the solution was dried with $Na_2SO_4$ and concentrated. Then, ether-petroleum ether was added to the residue to separate out a precipitate, which was collected by filtration.

Yield: 1.01 g (98.0%), Melting point: 94°–97° C., $Rf_1$: 0.41, $Rf_2$: 0.70 $[\alpha]_D^{28}$ −0.1° (c=0.78, in DMF)

Elemental analysis: As $C_{70}H_{77}N_7O_{15}S$ Calculated: C, 65.25; H, 6.02; N, 7.61; S, 2.49 Found: C, 65.40; H, 6.13; N, 7.75; S, 2.30

(5) Production of Boc-D-Thg(2)-Leu-D-Trp-D-Asp(OBzl)-Hyp(Bzl)-Asp(OBzl)-OH

Boc-D-Thg(2)-Leu-D-Trp-D-Asp(OBzl)-Hyp(Bzl)-Asp(OBzl)-OPac (0.77 g) was dissolved in 90% aqueous AcOH (20 ml), and Zn powder (1.96 g) was added thereto, followed by stirring for 3 hours. The Zn powder was removed by filtration, and filtrate was concentrated. AcOEt was added to the residue to dissolve it, and the solution was washed with 10% aqueous citric acid. After washing with water, the solution was dried with $Na_2SO_4$ and concentrated. Then, petroleum ether was added to the residue to separate out a precipitate, which was collected by filtration.

Yield: 0.70 g (99.7%), Melting point: 108°–110° C., $Rf_1$: 0.33, $Rf_2$: 0.65 $[\alpha]_D^{28}$ +4.6° (c=1.15, in DMF)

Elemental analysis: As $C_{62}H_{71}N_7O_{14}S$ Calculated: C, 63.63; H, 6.11; N, 8.38; S, 2.74 Found: C, 63.83; H, 6.23; N, 8.49; S, 2.45

(6) Production of cyclo[-D-Asp-Hyp(Bzl)-Asp-D-Thg(2)-Leu-D-Trp-]

Boc-D-Thg(2)-Leu-D-Trp-D-Asp(OBzl)-Hyp(Bzl)-Asp(OBzl)-OH (0.35 g) was dissolved in DCM (10 ml), and the solution was cooled with ice. HONB (0.11 g) and DCC (0.12 g) were added thereto, followed by stirring for 3 hours. Then, the resulting DCU was separated by filtration, followed by concentration, and ether was added to the residue to separate out a precipitate, which was collected by filtration. 8N-HCl/dioxane (10 ml) was added thereto under ice cooling to dissolve the precipitate. The resulting solution was stirred for 10 minutes and concentrated. Then, ether was added to the residue to separate out a precipitate, which was collected by filtration and dried. The precipitate was dissolved in DMF (6 ml), and the resulting solution was added dropwise to DMF (54 ml) containing TEA (0.42 ml) for 30 minutes, followed by stirring overnight and concentration. The residue was dissolved in AcOEt, and the solution was washed with 4% aqueous $NaHCO_3$. After washing with water, the solution was dried with $Na_2SO_4$ and concentrated. Then, ether-petroleum ether was added to the residue to separate out a precipitate, which was collected by filtration and dried. Of this precipitate, 74 mg was dissolved in DMF (15 ml) and catalytically reduced in a stream of hydrogen using palladium black as a catalyst. The catalyst was removed by filtration, and then the filtrate was concentrated. The resulting residue was dissolved in a small amount of AcOH, and thereafter, water was added thereto to conduct lyophilization. Finally, a part of the lyophilized product was purified by liquid chromatography using a YMC-D-ODS-5 column (2 cm×25 cm) (Y.M.C.) to obtain a desired material. The yield was 4.7 mg (5.7%).

Anal. for amino acids [110° C., hydrolysis for 24 hours; figures in parentheses show theoretical values.]: Asp 2.00(2); Leu 1.18(1) LSIMS (M+H$^+$)=872, (theoretical value)=872

EXAMPLE 89

Production of cyclo[-D-Asp-Glu(Bzl)-Asp-D-Thg(2)-Leu-D-Trp-]
(1) Production of Boc-Glu(Bzl)-OBzl Boc-Glu-OBzl (1.17 g, purchased from Watanabe Kagaku) was dissolved in acetonitrile (50 ml), and HONB (0.68 g) and DCC (0.79 g) were added thereto, followed by stirring for 2 hours under ice cooling. The resulting insoluble material was separated by filtration, and benzylamine (0.76 ml) was added thereto, followed by stirring overnight. After concentration of the reaction solution, the residue was dissolved in AcOEt, and the solution was washed with water, 10% aqueous citric acid and 4% aqueous NaHCO$_3$. After washing with water, the solution was dried with Na$_2$SO$_4$ and concentrated. Then, ether was added to the residue to separate out a precipitate, which was collected by filtration.

Yield: 1.37 g (92.6%), Melting point: 91.5°–92.5° C., Rf$_1$: 0.36, Rf$_2$: 0.69 [α]$_D^{25}$ −16.5° (c=1.02, in DMF)

Elemental analysis: As C$_{24}$H$_{30}$N$_2$O$_5$ Calculated: C, 67.59; H, 7.09; N, 6.57 Found: C, 67.44; H, 7.20; N, 6.68
(2) Production of Boc-Gln(Bzl)-Asp(OBzl)-OPac Boc-Gln(Bzl)-OH (3.36 g) [prepared by catalytically reducing Boc-Gln(Bzl)-OBzl (4.26 g) in methanol (20 ml) in a stream of hydrogen at ordinary temperature and pressure in the presence of 10% Pd-carbon (20 mg)] was dissolved in THF, and the solution was cooled to −15° C. with stirring. Then, N-methylmorpholine (1.1 ml) was added thereto, and subsequently, IBCF (1.3 ml) was added. After 2 minutes, a DMF solution of HCl.Asp(OBzl)-OPac and N-methylmorpholine (1.1 ml) was added. HCl.Asp(OBzl)-OPac was obtained by dissolving Boc-Asp(OBzl)-OPac (4.41 g) in 8-N HCl/dioxane (50 ml), stirring the solution under ice cooling for 30 minutes, followed by concentration, and adding ether to precipitate crystals, which were collected by filtration and dried. After stirring at −15° C. for 30 minutes, the solution was brought to room temperature. After 30 minutes, the resulting insoluble material was separated by filtration, followed by concentration. The residue was dissolved in AcOEt, and the solution was washed with water, 10% aqueous citric acid and 4% aqueous NaHCO$_3$. After washing with water, the solution was dried with Na$_2$SO$_4$ and concentrated. Ether was added to the resulting residue to separate out a precipitate, which was collected by filtration.

Yield: 5.11 g (77.5%), Melting point: 148.5°–150.0° C., Rf$_1$: 0.41, Rf$_2$: 0.64 [α]$_D^{28}$ −13.4° (c=1.00, in DMF)

Elemental analysis: As C$_{36}$H$_{41}$N$_3$O$_9$ Calculated: C, 65.54; H, 6.26; N, 6.37 Found: C, 65.38; H, 6.25; N, 6.34
(3) Production of Boc-D-Asp(OBzl)-Gln(Bzl)-Asp(OBzl)-OPac 8N-HCl/dioxane was added to Boc-Gln(Bzl)-Asp(OBzl)-OPac (3.96 g) to dissolve it, and the solution was stirred under ice cooling for 10 minutes, followed by concentration. Then, ether was added to the residue to precipitate crystals, which were collected by filtration and dried. The crystals were dissolved in DMF (40 ml) and cooled with ice. Then, TEA (1.67 ml) was added thereto. Boc-D-Asp(OBzl)-ONB [prepared from Boc-D-Asp(OBzl)-OH (2.16 g), HONB (1.31 g) and DCC (1.51 g)] was added thereto, followed by stirring overnight. The resulting insoluble material was separated by filtration, followed by concentration. The residue was dissolved in AcOEt, and the solution was washed with water, 10% aqueous citric acid and 4% aqueous NaHCO$_3$. After washing with water, the solution was dried with Na$_2$SO$_4$ and concentrated. Then, ether was added to the residue to separate out a precipitate, which was collected by filtration.

Yield: 4.56 g (87.9%), Melting point: 140°–141° C., Rf$_1$: 0.42, Rf$_2$: 0.69 [α]$_D^{28}$ −2.0° (c=1.02, in DMF)

Elemental analysis: As C$_{47}$H$_{52}$N$_4$O$_{12}$ Calculated: C, 65.27; H, 6.06; N, 6.48 Found: C, 65.05; H, 6.13; N, 6.67
(4) Production of Boc-D-Trp-D-Asp(OBzl)-Gln(Bzl)-Asp(OBzl)-OPac 8N-HCl/dioxane was added to Boc-D-Asp(OBzl)-Gln(Bzl)-Asp(OBzl)-OPac (1.73 g) to dissolve it, and the solution was stirred under ice cooling for 10 minutes, followed by concentration. Then, ether was added to the residue to precipitate crystals, which were collected by filtration and dried. The crystals were dissolved in DMF (20 ml) and cooled with ice. Then, TEA (0.56 ml) was added thereto. Boc-D-Trp-ONB [prepared from Boc-D-Trp-OH (0.67 g), HONB (0.43 g) and DCC (0.50 g)] was added thereto, followed by stirring overnight. The resulting insoluble material was separated by filtration, followed by concentration. The residue was dissolved in AcOEt, and the solution was washed with water, 10% aqueous citric acid and 4% aqueous NaHCO$_3$. After washing with water, the solution was dried with Na$_2$SO$_4$ and concentrated. Then, ethyl acetate was added to the residue to separate out a precipitate, which was collected by filtration.

Yield: 1.98 g (94.2%), Melting point: 194°–196° C., Rf$_1$: 0.36, Rf$_2$: 0.67 [α]$_D^{28}$ +1.6° (c=0.93, in DMF)

Elemental analysis: As C$_{58}$H$_{62}$N$_6$O$_{13}$ Calculated: C, 66.27; H, 5.95; N, 7.99 Found: C, 66.14; H, 6.03; N, 8.07
(5) Production of Boc-Leu-D-Trp-D-Asp(OBzl)-Gln(Bzl)-Asp(OBzl)-OPac 8N-HCl/dioxane was added to Boc-D-Trp-D-Asp(OBzl)-Gln(Bzl)-Asp(OBzl)-OPac (1.05 g) to dissolve it, and the solution was stirred under ice cooling for 10 minutes, followed by concentration. Then, ether was added to the residue to precipitate crystals, which were collected by filtration and dried. The crystals were dissolved in DMF (15 ml) and cooled with ice. Then, TEA (0.28 ml) was added thereto. Boc-Leu-ONB [prepared from Boc-Leu-OH.H$_2$O (0.27 g), HONB (0.22 g) and DCC (0.25 g)] was added thereto, followed by stirring for 3 hours. The resulting insoluble material was separated by filtration, followed by concentration. The residue was dissolved in AcOEt, and the solution was washed with water, 10% aqueous citric acid and 4% aqueous NaHCO$_3$. After washing with water, the solution was dried with Na$_2$SO$_4$ and concentrated. Then, ether was added to the residue to separate out a precipitate, which was collected by filtration.

Yield: 1.04 g (89.3%), Melting point: 175°–177° C., Rf$_1$: 0.38, Rf$_2$: 0.68 [α]$_D^{28}$ +0.35° (c=0.85, in DMF)

Elemental analysis: As C$_{64}$H$_{73}$N$_7$O$_{14}$ Calculated: C, 66.02; H, 6.32; N, 8.42 Found: C, 65.94; H, 6.43; N, 8.48
(6) Production of Boc-D-Thg(2)-Leu-D-Trp-D-Asp(OBzl)-Gln(Bzl)-Asp(OBzl)-OPac 8N-HCl/dioxane was added to Boc-Leu-D-Trp-D-Asp(OBzl)-Gln(Bzl)-Asp(OBzl)-OPac (0.93 g) to dissolve it, and the solution was stirred under ice cooling for 15 minutes, followed by concentration. Then, ether was added to the residue to precipitate crystals, which were collected by filtration and dried. The crystals were dissolved in DMF (5 ml) and cooled with ice. Then, TEA (0.22 ml) was added thereto. Boc-D-Thg(2)-OH (0.23 g), HONB (0.13 g) and DCC (0.20 g) were added thereto, followed by stirring for 3 hours. The resulting insoluble material was separated by filtration, followed by concentration. The residue was dissolved in AcOEt, and the solution was washed with water, 10% aqueous citric acid and 4% aqueous NaHCO$_3$. After washing with water, the solution was dried with Na$_2$SO$_4$ and concentrated. Then, ether was added to the residue to separate out a precipitate, which was collected by filtration.

Yield: 1.02 g (97.9%), Melting point: 170°–172° C., Rf$_1$: 0.30, Rf$_2$: 0.69 $[\alpha]_D^{28}$ +3.6° (c=0.83, in DMF)

Elemental analysis: As C$_{70}$H$_{78}$N$_8$O$_{15}$S Calculated: C, 64.50; H, 6.03; N, 18.60; S, 2.46 Found: C, 64.52; H, 6.15; N, 8.77; S, 2.41

(7) Production of Boc-D-Thg(2)-Leu-D-Trp-D-Asp(OBzl)-Gln(Bzl)-Asp(OBzl)-OH

Boc-D-Thg(2)-Leu-D-Trp-D-Asp(OBzl)-Gln(Bzl)-Asp(OBzl)-OPac (0.78 g) was dissolved in 90% aqueous AcOH (15 ml), and Zn powder (1.96 g) was added thereto, followed by stirring for 3 hours. The Zn powder was removed by filtration, and the filtrate was concentrated. AcOEt was added to the residue to dissolve it, and the solution was washed with 10% aqueous citric acid. After washing with water, the solution was dried with Na$_2$SO$_4$ and concentrated. Then, petroleum ether was added to the residue to separate out a precipitate, which was collected by filtration.

Yield: 0.67 g (94.2%), Melting point: 145°–147° C., Rf$_1$: 0.22, Rf$_2$: 0.66 $[\alpha]_D^{28}$ +6.6° (c=1.00, in DMF).

Elemental analysis: As C$_{62}$H$_{72}$N$_8$O$_{14}$S Calculated: C, 62.82; H, 6.12; N, 9.45; S, 2.71 Found: C, 62.93; H, 6.24; N, 9.62; S, 2.44

(8) Production of cyclo[-D-Asp-Gln(Bzl)-Asp-D-Thg(2)-Leu-D-Trp-]

Boc-D-Thg(2)-Leu-D-Trp-D-Asp(OBzl)-Gln(Bzl)-Asp(OBzl)-OH (0.36 g) was dissolved in DCM (10 ml), and the solution was cooled with ice. HONB (0.11 g) and DCC (0.12 g) were added thereto, followed by stirring for 3 hours. Then, the resulting DCU was separated by filtration, followed by concentration, and ether was added to the residue to separate out a precipitate, which was collected by filtration. 8N-HCl/dioxane (10 ml) was added thereto under ice cooling to dissolve the precipitate. The resulting solution was stirred for 10 minutes and concentrated. Then, ether was added to the residue to separate out a precipitate, which was collected by filtration and dried. The precipitate was dissolved in DMF (6 ml), and the resulting solution was added dropwise to DMF (54 ml) containing TEA (0.42 ml) for 30 minutes, followed by stirring overnight and concentration. The residue was dissolved in AcOEt, and the solution was washed with 4% aqueous NaHCO$_3$. After washing with water, the solution was dried with Na$_2$SO$_4$ and concentrated. Then, ether-petroleum ether was added to the residue to separate out a precipitate, which was collected by filtration and dried. Of this precipitate, 75 mg was dissolved in DMF (15 ml) and catalytically reduced in a stream of hydrogen using palladium black as a catalyst. The catalyst was removed by filtration, and then the filtrate was concentrated. The resulting residue was dissolved in a small amount of AcOH, and thereafter, water was added thereto to conduct lyophilization. Finally, a part of the lyophilized product was purified by liquid chromatography using a YMC-D-ODS-5 column (2 cm×25 cm) (Y.M.C.) to obtain a desired material. The yield was 5.0 mg (8.8%).

Anal for amino acids [110° C., hydrolysis for 24 hours; figures in parentheses show theoretical values.]: Asp 2.00(2); Glu 1.08 (1); Leu 1.09(1) LSIMS (M+H$^+$)=887, (theoretical value)=887

EXAMPLE 90

[A] Production of cyclo[-D-Asp-Asn(CH$_2$CH$_2$-Ind)-Asp-DThg-(2)-Leu-D-Trp-]

(1) Production of Boc-Asn(CH$_2$CH$_2$-Ind)-OBzl

Boc-Asp(ONB)-OBzl [prepared from Boc-Asp-OBzl (14.23 g), HONB (8.68 g) and DCC (9.99 g)] was added to tryptamine hydrochloride (7.87 g) together with TEA (8.4 ml) in DMF (150 ml) under ice-cooling, and the mixture was stirred overnight. The reaction solution was concentrated, and the residue was dissolved in AcOEt. The resulting solution was washed with water, 10% aqueous citric acid and 4% aqueous NaHCO$_3$. After washing with water, the solution was dried with Na$_2$SO$_4$ and concentrated. Then, ether was added to the residue to give crystals, which were collected by filtration.

Yield: 17.1 g (92.0%), Melting point: 96°–97° C., Rf$_1$: 0.41, Rf$_2$: 0.70 $[\alpha]_D^{28}$ −9.8° (c=1.24, in DMF)

Elemental analysis: As C$_{26}$H$_{30}$N$_3$O$_5$ Calculated: C, 67.22; H, 6.51; N, 9.05 Found: C, 67.31; H, 6.44; N, 8.97

(2) Production of Boc-Asn(CH$_2$CH$_2$-Ind)-OH.CHA

Boc-Asn(CH$_2$CH$_2$-Ind)-OBzl (4.6 g) was dissolved in methanol (100 ml) and catalytically reduced in a stream of hydrogen using palladium black as a catalyst. The catalyst was removed by filtration, and then the filtrate was concentrated. The resulting residue was dissolved in ether-AcOEt (1:1), and CHA (1.1 ml) was added thereto to precipitate crystals, which were collected by filtration. The crystals were recrystallized from methanol-ether to obtain a desired material.

Yield: 4.1 g (88.9%), Melting point: 178°–179° C., Rf$_2$: 0.37 $[\alpha]_D^{28}$ +7.5° (c=1.17, in methanol)

Elemental analysis: As C$_{25}$H$_{37}$N$_4$O$_5$ Calculated: C, 63.13; H, 8.26; N, 11.78 Found: C, 63.11; H, 8.22; N, 11.78

(3) Production of Boc-Asn(CH$_2$CH$_2$-Ind)-Asp(OBzl)-OPac

Boc-Asn(CH$_2$CH$_2$-Ind)-OH [prepared from Boc-Asn(CH$_2$CH$_2$-Ind)-OH.CHA (3.7 g)] was dissolved in THF, and the solution was cooled to −15° C. with stirring. Then, N-methylmorpholine (0.9 ml) was added thereto, and subsequently, IBCF (1.1 ml) was added. After 2 minutes, a DMF solution of HCl.Asp(OBzl)-OPac and N-methylmorpholine was added. HCl.Asp(OBzl)-OPac was obtained by dissolving Boc-Asp(OBzl)-OPac (3.5 g) in 8-N HCl/dioxane (20 ml), stirring the solution under ice cooling for 30 minutes, followed by concentration, and adding ether to precipitate crystals, which were collected by filtration and dried. After stirring at −15° C. for 30 minutes, the solution was brought to room temperature. After 30 minutes, the resulting insoluble material was separated by filtration, followed by concentration. The residue was dissolved in AcOEt, and the solution was washed with water, 10% aqueous citric acid and 4% aqueous NaHCO$_3$. After washing with=water, the solution was dried with Na$_2$SO$_4$ and concentrated. Ether was added to the resulting residue to separate out a precipitate, which was collected by filtration.

Yield: 4.3 g (79.2%), Melting point: 142°–143° C., Rf$_1$: 0.38, Rf$_2$: 0.69 $[\alpha]_D^{28}$ −8.0° (c=0.97, in DMF)

Elemental analysis: As C$_{38}$H$_{41}$N$_4$O$_9$ Calculated: C, 65.41; H, 5.92; N, 8.03 Found: C, 65.46; H, 5.95; N, 7.89

(4) Production of Boc-Asp(OBzl)-Asn(CH$_2$CH$_2$-Ind)-Asp(OBzl)-OPac

8N-HCl/dioxane was added to Boc-Asn(CH$_2$CH$_2$-Ind)-Asp(OBzl)-OPac (4.09 g) to dissolve it, and the solution was stirred under ice cooling for 10 minutes, followed by concentration. Then, ether was added to the residue to precipitate crystals, which were collected by filtration and dried. The crystals were dissolved in DMF (40 ml) and cooled with ice. Then, TEA (1.67 ml) was added thereto. Boc-D-Asp(OBzl)-ONB [prepared from Boc-D-Asp(OBzl)-OH (2.16 g), HONB (1.31 g) and DCC (1.51 g)] was added thereto, followed by stirring overnight. The resulting insoluble material was separated by filtration, followed by concentration. The residue was dissolved in AcOEt, and the solution was washed with water, 10% aqueous citric acid and 4% aqueous NaHCO$_3$. After washing with water, the solution was dried with Na$_2$SO$_4$ and concentrated. Then, ether was added to the residue to separate out a precipitate, which was collected by filtration.

Yield: 4.84 g (89.2%), Melting point: 92°–94° C., Rf$_1$: 0.41, Rf$_2$: 0.67 [α]$_D^{28}$ −7.4° (c=1.11, in DMF)

Elemental analysis: As C$_{49}$H$_{53}$N$_5$O$_{12}$ Calculated: C, 65.10; H, 5.91; N, 7.75 Found: C, 64.85; H, 5.97; N, 7.93

(5) Production of Boc-D-Trp-D-Asp(OBzl)-Asn(CH$_2$CH$_2$-Ind)-Asp(OBzl)-OPac

8N-HCl/dioxane was added to Boc-D-Asp(OBzl)-Asn(CH$_2$CH$_2$-Ind)-Asp(OBzl)-OPac (1.77 g) to dissolve it, and the solution was stirred under ice cooling for 10 minutes, followed by concentration. Then, ether was added to the residue to precipitate crystals, which were collected by filtration and dried. The crystals were dissolved in DMF (20 ml) and cooled with ice. Then, TEA (0.56 ml) was added thereto. Boc-D-Trp-ONB [prepared from Boc-D-Trp-OH (0.67 g), HONB (0.43 g) and DCC (0.50 g)] was added thereto, followed by stirring overnight. The resulting insoluble material was separated by filtration, followed by concentration. The residue was dissolved in AcOEt, and the solution was washed with water, 10% aqueous citric acid and 4% aqueous NaHCO$_3$. After washing with water, the solution was dried with NagSO$_4$ and concentrated. Then, the residue was purified using silica gel chromatography (2% methanol/DCM). Subsequently, petroleum ether was added thereto to separate out a precipitate, which was collected by filtration.

Yield: 1.24 g (56.9%), Melting point: 139°–140° C., Rf$_1$: 0.34, Rf$_2$: 0.67 [α]$_D^{28}$ −0.1° (c=0.92, in DMF)

Elemental analysis: As C$_{60}$H$_{63}$N$_7$O$_{13}$ Calculated: C, 66.10; H, 5.82; N, 8.99 Found: C, 65.98; H, 5.83; N, 8.95

(6) Production of Boc-Leu-D-Trp-D-Asp(OBzl)-Asn(CH$_2$CH$_2$-Ind)-Asp(OBzl)-OPac 8-N HCl/dioxane was added to Boc-D-Trp-D-Asp(OBzl)-Asn(CH$_2$CH$_2$-Ind)-Asp(OBzl)-OPac (1.09 g) to dissolve it, and the solution was stirred under ice cooling for 30 minutes, followed by concentration. Then, ether was added to the residue to precipitate crystals, which were collected by filtration and dried. The crystals were dissolved in DMF (15 ml) and cooled with ice. Then, TEA (0.28 ml) was added thereto. Boc-Leu-ONB [prepared from Boc-Leu-OH.H$_2$O (0.27 g), HONB (0.22 g) and DCC (0.25 g)] was added thereto, followed by stirring for 3 hours. The resulting insoluble material was separated by filtration, followed by concentration. The residue was dissolved in AcOEt, and the solution was washed with water, 10% aqueous citric acid and 4% aqueous NaHCO$_3$. After washing with water, the solution was dried with Na$_2$SO$_4$ and concentrated. Then, ether was added to the residue to separate out a precipitate, which was collected by filtration.

Yield: 1.10 g (91.4%), Melting point: 140°–142° C., Rf$_1$: 0.34, Rf$_2$: 0.67 [α]$_D^{28}$ −0.5° (c=0.84, in DMF)

Elemental analysis: As C$_{66}$H$_{74}$N$_8$O$_{14}$ Calculated: C, 65.88; H, 6.20; N, 9.31 Found: C, 66.00; H, 6.23; N, 9.20

(7) Production of Boc-D-Thg(2)-Leu-D-Trp-D-Asp(OBzl)-Asn(CH$_2$CH$_2$-Ind)-Asp(OBzl)-OPac 8N-HCl/dioxane was added to Boc-Leu-D-Trp-D-Asp(OBzl)-Asn(CH$_2$CH$_2$-Ind)-Asp(OBzl)-OPac (0.96 g) to dissolve it, and the solution was stirred under ice cooling for 10 minutes, followed by concentration. Then, ether was added to the residue to precipitate crystals, which were collected by filtration and dried. The crystals were dissolved in DMF (10 ml) and cooled with ice. Then, TEA (0.22 ml) was added thereto. Boc-D-Thg(2)-OH (0.23 g), HONB (0.13 g) and DCC (0.20 g) were added thereto, followed by stirring for 3 hours. The resulting insoluble material was separated by filtration, followed by concentration. The residue was dissolved in AcOEt, and the solution was washed with water, 10% aqueous citric acid and 4% aqueous NaHCO$_3$. After washing with water, the solution was dried with Na$_2$SO$_4$ and concentrated. Then, ether was added to the residue to separate out a precipitate, which was collected by filtration.

Yield: 1.06 g (98.7%), Melting point: 162°–164° C., Rf$_1$: 0.30, Rf$_2$: 0.69 [α]$_D^{28}$ +4.4° (c=0.75, in DMF)

Elemental analysis: As C$_{72}$H$_{79}$N$_9$O$_{15}$S Calculated: C, 64.41; H, 5.93; N, 9.39; S, 2.39 Found: C, 64.36; H, 6.04; N, 9.49; S, 2.16

(8) Production of Boc-D-Thg(2)-Leu-D-Trp-D-Asp(OBzl)-Asn(CH$_2$CH$_2$-Ind)-Asp(OBzl)-OH Boc-D-Thg(2)-Leu-D-Trp-D-Asp(OBzl)-Asn(CH$_2$CH$_2$-Ind)-Asp(OBzl)-OPac (0.81 g) was dissolved in 90% aqueous AcOH (20 ml), and Zn powder (1.96 g) was added thereto, followed by stirring for 3 hours. The Zn powder was removed by filtration, and the filtrate was concentrated. AcOEt was added to the residue to dissolve it, and the solution was washed with 10% aqueous citric acid. After washing with water, the solution was dried with Na$_2$SO$_4$ and concentrated. Then, petroleum ether was added to the residue to separate out a precipitate, which was collected by filtration.

Yield: 0.72 g (98.0%), Melting point: 140°–143° C., Rf$_1$: 0.22, Rf$_2$: 0.66 [α]$_D^{28}$ +5.8° (c=0.93, in DMF)

Elemental analysis: As C$_{64}$H$_{73}$N$_9$O$_{14}$S Calculated: C, 62.78; H, 6.01; N, 10.30; S, 2.62 Found: C, 62.75; H, 6.14; N, 10.27; S, 2.49

(9) Production of cyclo[-D-Asp-Asn(CH$_2$CH$_2$-Ind)-Asp-D-Thg(2)-Leu-D-Trp-]

Boc-D-Thg(2)-Leu-D-Trp-D-Asp(OBzl)-Asn(CH$_2$CH$_2$-Ind)-Asp(OBzl)-OH (0.37 g) was dissolved in DCM (10 ml), and the solution was cooled with ice. HONB (0.11 g) and DCC (0.12 g) were added thereto, followed by stirring for 3 hours. Then, the resulting DCU was separated by filtration, followed by concentration, and ether was added to the residue to separate out a precipitate, which was collected by filtration. 8-N HCl/dioxane (10 ml) was added thereto under ice cooling to dissolve the precipitate. The resulting solution was stirred for 10 minutes and concentrated. Then, ether was added to the residue to separate out a precipitate, which was collected by filtration and dried. The precipitate was dissolved in DMF (6 ml), and the resulting solution was added dropwise to DMF (54 ml) containing TEA (0.4 ml) for 30 minutes, followed by stirring overnight and concentration. The residue was dissolved in AcOEt, and the solution was washed with 4% aqueous NaHCO$_3$. After washing with water, the solution was dried with Na$_2$SO$_4$ and concentrated. Then, ether-petroleum ether was added to the residue to separate out a precipitate, which was collected by filtration and dried. Of this precipitate, 111 mg was dissolved in DMF (15 ml) and catalytically reduced in a stream of hydrogen using palladium black as a catalyst. The catalyst was removed by filtration, and then the filtrate was concentrated. The resulting residue was dissolved in a small amount of AcOH, and thereafter, water was added thereto to conduct lyophilization. Finally, a part of the lyophilized product was purified by liquid chromatography using a YMC-D-ODS-5 column (2 cm×25 cm) (Y.M.C.) to obtain a desired material. The yield was 5.4 mg (9.5%).

Anal. for amino acids [110° C., hydrolysis for 24 hours; figures in parentheses show theoretical values.]: Asp 3.00(3); Leu 1.39(1) LSIMS (M+H$^+$)=926, (theoretical value)=926 [B]

EXAMPLE

Production of cyclo[-D-Asp-Asn(CH$_2$CH$_2$Ind)-AsP-D-Thg(2)-Leu-D-Trp-]

(1) Production of Boc-D-Thg(2)-Leu-OBzl

Boc-Thg(2)-OH.CHA (17.8 g, 50 mmoles) was suspended in a mixed solvent of ethyl acetate (250 ml) and water (250 ml), followed by vigorous stirring. Then, 1N aqueous H$_2$SO$_4$ (50 ml) was added thereto to dissolve it completely. The ethyl acetate layer was separated and dried with Na$_2$SO$_4$. The solvent was thereafter removed by evaporation under reduced pressure. DMF (90 ml) was added to the residue to prepare solution (I).

Tos.H-Leu-OBzl (39.4 g, 100 mmoles) was added to a mixed solvent of ethyl acetate (250 ml) and 10% aqueous NaHCO$_3$ (250 ml), followed by vigorous stirring to dissolve it completely. The ethyl acetate layer was separated and dried with Na$_2$SO$_4$. The solvent was thereafter removed by evaporation under reduced pressure. DMF (90 ml) was added to the residue to prepare solution (II).

Solutions (I) and (II) were combined with each other, and HOBT (13.5 g, 100 mmoles) was added thereto to dissolve it. Then, 30 ml of a solution of DCC (20.6 g, 100 mmoles) in DMF was added dropwise thereto under ice cooling for 10 minutes, followed by stirring for 1 hour. The resulting solution was thereafter stirred overnight at 4° C. The insoluble material was removed by filtration, and the solvent was removed by evaporation. Ethyl acetate and water were added to the residue, and 1N aqueous H$_2$SO$_4$ (50 ml) was added thereto, followed by extraction with ethyl acetate. The ethyl acetate layer was separated and washed successively with the saturated aqueous solution of NaCl, 4% aqueous NaHCO$_3$ and the saturated aqueous solution of NaCl. After drying with Na$_2$SO$_4$, the solvent was removed by evaporation. The residue was purified by silica gel column chromatography (6 cm×30 cm, hexane:ethyl acetate=10:1–3:1). Colorless crystals were obtained by crystallization from a petroleum ether solution.

Yield: 14.9 g (87.2%)

Melting point: 71.0°–72.5° C., Rf1: 0.80, Rf2: 0.88 [α]$_D^{25}$ −46.3° (c=1.02, in DMF)

Elemental analysis: As C$_{24}$H$_{32}$N$_2$O$_5$S Calculated: C, 62.59; H, 7.00; N, 6.08 Found: C, 62.35; H, 7.00; N, 6.10

(2) Production of Boc-D-Thg(2)-Leu-OPac

In 500 ml of methanol was dissolved 16.1 g (35.0 mmoles) of Boc-D-Thg(2)-Leu-OBzl synthesized in (1), and 5 g of charcoal was added thereto, followed by stirring. The charcoal was removed by filtration, and 1 g of palladium black was added to the filtrate. The mixture was stirred in a stream of hydrogen at room temperature for 5 hours. The catalyst was removed by filtration, and the filtrate was concentrated to about 100 ml under reduced pressure. Then, 50 ml of a aqueous solution of Cs$_2$CO$_3$ (5.70 g, 17.5 mmoles) was added dropwise thereto for 10 minutes, followed by stirring for 30 minutes. The solvent was thereafter removed by evaporation. DMF (100 ml) was added to the residue, and the solvent was removed by evaporation under reduced pressure. This operation was repeated twice. DMF (100 ml) was added to the residue to dissolve it, and 50 ml of a solution of phenacyl bromide (7.18 g, 35.0 mmoles) in DMF was added dropwise thereto under ice cooling for 10 minutes. The resulting mixture was brought to room temperature and then stirred overnight. The solvent was removed by distillation, and ethyl acetate was added to the residue, followed by extraction with ethyl acetate. The ethyl acetate layer was separated and washed successively with 10% aqueous citric acid, the saturated aqueous solution of NaCl, the saturated aqueous solution of NaHCO$_3$ and the saturated aqueous solution of NaCl. After drying with Na$_2$SO$_4$, the solvent was removed. Colorless crystals were obtained by crystallization from an ether-petroleum ether.

Yield: 14.9 (87.2%)

Melting point: 119.0°–120.0° C., Rf1: 0.79, Rf2: 0.91 [α]$_D^{25}$ −50.2° (c=1.05, in DMF)

Elemental analysis: As C$_{25}$H$_{32}$N$_2$O$_6$S Calculated: C, 61.46; H, 6.60; N, 5.73 Found: C, 61.43; H, 6.63; N, 5.85

(3) Production of Boc-Asp(OBzl)-D-Thg(2)-Leu-OPac

In 30 ml of dioxane was dissolved 14.7 g (30.0 mmoles) of Boc-D-Thg(2)-Leu-OPac synthesized in (2), and 10N-HCl/dioxane (50 ml) was added thereto under ice cooling, followed by stirring for 15 minutes. The solvent was removed by evaporation under reduced pressure, and ether was added to the residue. The resulting precipitate was collected by filtration and dried. The precipitate was dissolved in DMF (160 ml) and the solution was cooled with ice. Then, diisopropylethylamine (5.30 ml, 30.36 mmoles) was added thereto. Boc-Asp(OBzl)-ONB [prepared from Boc-Asp(OBzl)-OH (9.68 g, 30 mmoles), HONB (5.91 g, 33.0 mmoles) and DCC (6.81 g, 33.0 mmoles)] was further added thereto, followed by stirring overnight. The resulting insoluble material was separated by filtration, followed by concentration. The residue was dissolved in ethyl acetate, and the solution was washed with water, 10% aqueous citric acid, the saturated aqueous solution of NaCl, the saturated aqueous solution of NaHCO$_3$ and the saturated aqueous solution of NaCl. After drying with Na$_2$SO$_4$, the solvent was removed by evaporation. Ether-petroleum ether was added to the residue to obtain a precipitate.

Yield: 20.31 g (97.6%)

Melting point: 67.0°–68.5° C., Rf1: 0.61, Rf2: 0.83 [α]$_D^{25}$ −52.0° (c=1.03, in DMF)

Elemental analysis: As C$_{36}$H$_{43}$N$_3$O$_9$S Calculated: C, 62.32; H, 6.25; N, 6.06 Found: C, 62.34; H, 6.36; N, 6.20

(4) Production of Boc-Asn(NHCH$_2$CH$_2$Ind)-AsP(OBzl)-D-Thg(2)-Leu-OPac

In 30 ml of dioxane was dissolved 20.1 g (29.0 mmoles) of Boc-Asp(OBzl)-D-Thg(2)-Leu-OPac synthesized in (3), and 10N-HCl/dioxane (150 ml) was added thereto under ice cooling, followed by stirring for 15 minutes. The solvent was removed by evaporation under reduced pressure, and ether was added to the residue. The resulting precipitate was collected by filtration and dried. The precipitate was dissolved in DMF (240 ml) and the solution was cooled with ice. Then, diisopropylethylamine (5.05 ml, 29.0 mmoles) was added thereto. Boc-Asn(CH$_2$CH$_2$-Ind)-ONB [prepared from Boc-Asn(NHCH$_2$CH$_2$ind)-OH {prepared from Boc-Asn(NHCH$_2$CH$_2$Ind)-OH.CHA (14.5 g, 30.45 mmoles)}, HONB (5.72 g, 31.9 mmoles) and DCC (6.58 g, 31.9 mmoles)] was further added thereto, followed by stirring overnight. The resulting insoluble material was separated by filtration, followed by concentration of the filtrate to obtain the residue. Ethyl acetate-ether (1:1) was added to the residue to obtain a precipitate.

Yield: 26.68 g (96.7%)

Melting point: 178.0°–180.5° C., Rf1: 0.38, Rf2: 0.77 [α]$_D^{25}$ −44.8° (c=1.03, in DMF)

Elemental analysis: As C$_{50}$H$_{58}$N$_6$O$_{11}$S Calculated: C, 63.14; H, 6.15; N, 8.84 Found: C, 62.85; H, 6.11; N, 8.80

(5) Production of Boc-D-Asp(OBzl)-Asn(NHCH$_2$CH$_2$Ind)-Asp(OBzl)-D-Thg(2)-Leu-OPac In 25 ml of dioxane was dissolved 24.7 g (26.0 mmoles) of Boc-Asn(CH$_2$CH$_2$-Ind)-Asp(OBzl)-D-Thg(2)-Leu-OPac synthesized in (4), and 10N-HCl/dioxane (130 ml) was added thereto under ice cooling, followed by stirring for 15 minutes. The solvent was removed by evaporation under reduced pressure, and ether was added to the residue. The resulting precipitate was collected by filtration and dried. The precipitate was dissolved in DMF (200 ml), and diisopropylethylamine (4.53 ml, 26.0 mmoles) was added thereto under ice cooling. Boc-D-Asp(OBzl)-ONB [prepared from Boc-D-Asp(OBzl)-OH (8.82 g, 27.3 mmoles), HONB (5.12 g, 28.6 mmoles) and DCC (5.90 g, 28.6 mmoles)] was further added thereto, followed by stirring overnight. The resulting insoluble material was separated by filtration, followed by concentration of the filtrate to obtain the residue. The residue was dissolved in ethyl acetate, and the solution was washed with water, 10% aqueous citric acid, the saturated aqueous solution of NaCl, the saturated aqueous solution of NaHCO$_3$ and the saturated aqueous solution of NaCl. After drying with Na$_2$SO$_4$, the solvent was removed by evaporation. Ethyl acetate-ether was added to the residue to obtain a precipitate.

Yield: 25.82 g (85.9%)

Melting point: 148.0°–150.0° C., Rf1: 0.54 Rf2: 0.78 $[\alpha]_D^{25}$ −38.9° (c=1.04, in DMF)

Elemental analysis: As C$_{61}$H$_{69}$N$_7$O$_{14}$S Calculated: C, 63.36; H, 6.01; N, 8.48 Found: C, 63.15; H, 6.00; N, 8.45

(6) Production of Boc-D-Trp-D-Asp(OBzl)-Asn(NHCH$_2$CH$_2$Ind)-Asp(OBzl)-D-Thg(2)-Leu-OPac In 22 ml of dioxane was added 25.44 g (22.0 mmoles) of Boc-D-Asp(OBzl)-Asn(NHCH$_2$CH$_2$Ind)-Asp(OBzl)-D-Thg(2)-Leu-OPac synthesized in (5), and 10N-HCl/dioxane (110 ml) was added thereto under ice cooling, followed by stirring for 15 minutes. The solvent was removed by evaporation under reduced pressure, and ether was added to the residue. The resulting precipitate was collected by filtration and dried. The precipitate was dissolved in DMF (200 ml), and the solution was cooled with ice. Then, diisopropylethylamine (3.83 ml, 22.0 mmoles) was added thereto. Boc-D-Trp-ONB [prepared from Boc-D-Trp-OH (6.70 g, 22.0 mmoles), HONB (4.34 g, 24.2 mmoles) and DCC (5.00 g, 24.2 mmoles)] was further added thereto, followed by stirring overnight. The resulting insoluble material was separated by filtration, followed by concentration of the filtrate to obtain the residue. The residue was dissolved in chloroform, and the solution was washed with water, 10% aqueous citric acid, the saturated aqueous solution of NaCl, the saturated aqueous solution of NaHCO$_3$ and the saturated aqueous solution of NaCl. After drying with Na$_2$SO$_4$, the solvent was removed by evaporation. The residue was purified by silica gel column chromatography (9.5 cm×50 cm, 0.5% methanol-chloroform). Ether-petroleum ether was added to the purified product to obtain a precipitate.

Yield: 20.10 g (68.0%)

Melting point: 172.0°–173.5° C., Rf1: 0.52, Rf2: 0.77 $[\alpha]_D^{25}$ −24.1° (c=1.05, in DMF)

Elemental analysis: As C$_{72}$H$_{79}$N$_9$O$_{15}$S Calculated: C, 64.41; H, 5.93; N, 9.39 Found: C, 64.35; H, 5.99; N, 9.22

(7) Production of Boc-D-Trp-D-Asp(OBzl)-Asn(NHCH$_2$CH$_2$Ind)-Asp(OBzl)-D-Thg(2)-Leu-OH In 500 ml of a 90% aqueous solution of acetic acid was dissolved 6.71 g (5.00 mmoles) of Boc-D-Trp-D-Asp(OBzl)-Asn(NHCH$_2$CH$_2$Ind)-Asp(OBzl)-D-Thg(2)-Leu-OPac synthesized in (6), and 16.33 g (250.0 mmoles) of zinc powder was added thereto, followed by stirring for 1 hour. The zinc powder was separated by filtration, and the filtrate was concentrated. The residue was dissolved in ethyl acetate, and the solution was washed with 10% aqueous citric acid and the saturated aqueous solution of NaCl. After drying with Na$_2$SO$_4$, the solvent was removed by evaporation. Ether was added to the residue to obtain a precipitate.

Yield: 6.00 g (98.0%)

Melting point: 120.0°–122.0° C. Rf1: 0.00, Rf2: 0.67 $[\alpha]_D^{25}$ −18.8° (c=1.03, in DMF)

Elemental analysis: As C$_{64}$H$_{73}$N$_9$O$_{14}$S Calculated: C, 62.78; H, 6.01; N, 10.30 Found: C, 62.66; H, 5.96; N, 10.06

(8) Production of cyclo[-D-Asp(OBzl)-Asn(NHCH$_2$CH$_2$Ind)-Asp(OBzl)-D-Thg(2)-Leu-D-Trp-]

In 80 ml of DMF was dissolved 5.82 g (4.75 mmoles) of Boc-D-Trp-D-Asp(OBzl)-Asn(NHCH$_2$CH$_2$Ind)-Asp(OBzl)-D-Thg(2)-Leu-OH synthesized in (7), and the solution was cooled with ice. Then, HONB (1.70 g, 9.50 mmoles) and DCC (1.96 g, 9.50 mmoles) were added thereto, followed by stirring overnight. The resulting insoluble material was separated by filtration, followed by concentration of the filtrate to obtain the residue. Then, ether-petroleum ether was added to the residue to separate out a precipitate, which was collected by filtration. The precipitate was dissolved in dioxane (5 ml), and 10N-HCl/dioxane (50 ml) was added thereto under ice cooling, followed by stirring for 5 minutes. After concentration of the filtrate to obtain the residue, ether was added to the residue. The resulting precipitate was collected by filtration and dried. The precipitate was dissolved in DMF (100 ml). The solution was added dropwise to 900 ml of DMF containing diisopropylethylamine (8.27 ml, 47.5 mmoles) for 30 minutes, followed by stirring overnight. The solvent was removed by evaporation, and distilled water was added to the residue. The resulting precipitate was collected by filtration. The precipitate was dissolved in DMF, followed by concentration of the filtrate to obtain the residue. Then, ether was added to the residue to separate out a precipitate, which was collected by filtration, washed with acetonitrile and dried.

Yield: 4.75 g (90.4%)

(9) Production of cyclo[-D-Asp-Asn(NHCH$_2$CH$_2$Ind)-Asp-D-Thg(2)-Leu-D-Trp-]

In 100 ml of DMF was dissolved 2.00 g (1.81 mmoles) of cyclo[-D-Asp(OBzl)-Asn(NHCH$_2$CH$_2$Ind)-Asp(OBzl)-D-Thg(2)-Leu-D-Trp-] synthesized in (8), and 1 g of charcoal was added thereto, followed by stirring. The charcoal was removed by filtration, and 1 g of palladium black was added to the filtrate. The mixture was stirred in a stream of hydrogen at room temperature for 6 hours. In addition, 1 g of palladium black was added, and the mixture was stirred in a stream of hydrogen at room temperature for 6 hours. The catalyst was removed by filtration, and the solvent was removed by evaporation under reduced pressure. Then, ether was added to obtain a precipitate.

Yield: 1.68 g (quant.)

Of this precipitate, 1.50 g was purified by reversed phase liquid chromatography [column: YMC-Pack R & D D-ODS-5B (3 cm×25 cm), solvent: 30%–40% acetonitrile (30 minutes)/H$_2$O (0.1% TFA)].

Yield: 1.11 g LSIMS (M+H$^+$)=926, (theoretical value)= 926

(10) Production of cyclo[-D-Asp-Asn(NHCH$_2$CH$_2$Ind)-Asp-D-Thg(2)-Leu-D-Trp-].2Na In 60 ml of acetonitrile was suspended 3.00 g (3.24 mmoles) of cyclo[-D-Asp-Asn(NHCH$_2$CH$_2$Ind)-Asp-D-Thg(2)-Leu-D-Trp-] synthesized in (9), and the suspension was added dropwise to 240 ml of an aqueous solution of sodium carbonate (343.4 mg, 3.24 mmoles). After stirring at room temperature for 15 minutes, the pH was adjusted to 7.0 with a 0.1M aqueous solution of sodium carbonate, followed by concentration under reduced pressure. The resulting product was dissolved in 100 ml of distilled water and subjected to lyophilization.

Yield: 2.80 g

EXAMPLES 15–52, 57–78, 83–87 and 91–96

In accordance with the processes of Examples 1–14 (A), the processes of Examples 53–56 and 88–90 (B) or the processes of Examples 79–82 (C), the following compounds were synthesized:

| Example No. | Compound | Process |
|---|---|---|
| 15 | Cyclo[—D—Asp—D—Ala—Asp—D—Leu—Leu—D—Trp—] LSIMS(M + H$^+$) = 714, (theoretical value) = 714 | (A) |
| 16 | Cyclo[—D—Asp—Asp—Asp—D—Leu—Leu—D—Trp—] LSIMS(M + H$^+$) = 758, (theoretical value) = 758 | (A) |
| 17 | Cyclo[—D—Asp—Val—Asp—D—Leu—Leu—D—Trp—] LSIMS(M + H$^+$) = 742, (theoretical value) = 742 | (A) |
| 18 | Cyclo[—D—Asp—Leu—Asp—D—Leu—Leu—D—Trp—] LSIMS(M + H$^+$) = 756, (theoretical value) = 756 | (A) |
| 19 | Cyclo[—D—Asp—Phe—Asp—D—Leu—Leu—D—Trp—] LSIMS(M + H$^+$) = 790, (theoretical value) = 790 | (A) |
| 20 | Cyclo[—D—Asp—Ser(Bzl)—Asp—D—Leu—Leu—D—Trp—] LSIMS(M + H$^+$) = 820, (theoretical value) = 820 | (A) |
| 21 | Cyclo[—D—Asp—Thr(Bzl)—Asp—D—Leu—Leu—D—Trp—] LSIMS(M + H$^+$) = 834, (theoretical value) = 834 | (A) |
| 22 | Cyclo[—D—Asp—Trp(For)—Asp—D—Leu—Leu—D—Trp—] LSIMS(M + H$^+$) = 857, (theoretical value) = 857 | (A) |
| 23 | Cyclo[—D—Asp—Nal(1)—Asp—D—Leu—Leu—D—Trp—] LSIMS(M + H$^+$) = 840, (theoretical value) = 840 | (A) |
| 24 | Cyclo[—D—Asp—D—Pro—Asp—D—Leu—Leu—D—Trp—] LSIMS(M + H$^+$) = 740, (theoretical value) = 740 | (A) |
| 25 | Cyclo[—D—Asp—Azc—Asp—D—Leu—Leu—D—Trp—] LSIMS(M + H$^+$) = 725, (theoretical value) = 725 | (C) |
| 26 | Cyclo[—D—Asp—Pip—Asp—D—Leu—Leu—D—Trp—] LSIMS(M + H$^+$) = 753, (theoretical value) = 753 | (C) |
| 27 | Cyclo[—D—Asp—D—Asp—Ala—D—Leu—Leu—D—Trp—] LSIMS(M + H$^+$) = 714, (theoretical value) = 714 | (A) |
| 28 | Cyclo[—D—Asp—D—Glu—Ala—D—Leu—Leu—D—Trp—] LSIMS(M + H$^+$) = 728, (theoretical value) = 728 | (A) |
| 29 | Cyclo[—D—Asp—Asp—D—Ala—D—Leu—Leu—D—Trp—] LSIMS(M + H$^+$) = 714, (theoretical value) = 714 | (A) |
| 30 | Cyclo[—D—Asp—Asp—Pro—D—Leu—Leu—D—Trp—] LSIMS(M + H$^+$) = 740, (theoretical value) = 740 | (A) |
| 31 | Cyclo[—D—Asp—Asp—D—Pro—D—Leu—Leu—D—Trp—] LSIMS(M + H$^+$) = 740, (theoretical value) = 740 | (A) |
| 32 | Cyclo[—D—Asp—Asp—Leu—D—Leu—Leu—D—Trp—] LSIMS(M + H$^+$) = 756, (theoretical value) = 756 | (A) |
| 33 | Cyclo[—D—Asp—Asp—Trp—D—Leu—Leu—D—Trp—] LSIMS(M + H$^+$) = 829, (theoretical value) = 829 | (A) |
| 34 | Cyclo[—D—Asp—Trp—Glu—D—Leu—Leu—D—Trp—] LSIMS(M + H$^+$) = 844, (theoretical value) = 844 | (C) |
| 35 | Cyclo[—D—Asp—Trp—Leu—D—Leu—Leu—D—Trp—] LSIMS(M + H$^+$) = 828, (theoretical value) = 828 | (C) |
| 36 | Cyclo[—D—Asp—Trp—Pro—D—Leu—Leu—D—Trp—] LSIMS(M + H$^+$) = 811, (theoretical value) = 811 | (C) |
| 37 | Cyclo[—D—Asp—Trp—Ser—D—Leu—Leu—D—Trp—] LSIMS(M + H$^+$) = 801, (theoretical value) = 801 | (C) |
| 38 | Cyclo[—D—Asp—Trp—Ser(Bzl)—D—Leu—Leu—D—Trp—] LSIMS(M + H$^+$) = 892, (theoretical value) = 892 | (C) |
| 39 | Cyclo[—D—Asp—Ala—Asp—D—tLeu—Leu—D—Trp—] LSIMS(M + H$^+$) = 714, (theoretical value) = 714 | (A) |
| 40 | Cyclo[—D—Glu—Ala—Gly—D—Leu—Leu—D—Trp—] LSIMS(M + H$^+$) = 670, (theoretical value) = 670 | (A) |
| 41 | Cyclo[—D—Glu—Ala—Asp—D—Leu—Leu—D—Trp—] LSIMS(M + H$^+$) = 728, (theoretical value) = 728 | (A) |
| 42 | Cyclo[—D—Asp—Trp—Asp—D—Leu—Leu—D—Trp(For)—] LSIMS(M + H$^+$) = 857, (theoretical value) = 857 | (A) |
| 43 | Cyclo[—D—Asp—Trp—Asp—D—Leu—Leu—D—Trp(Ac)—] LSIMS(M + H$^+$) = 871, (theoretical value) = 871 | (A) |
| 44 | Cyclo[—D—Asp—Trp—Asp—Acpc—Leu—D—Trp—] LSIMS(M + H$^+$) = 827, (theoretical value) = 827 | (B) |
| 45 | Cyclo[—D—Asp—Trp—Asp—D—Phg—Leu—D—Trp—] LSIMS(M + H$^+$) = 849, (theoretical value) = 849 | (B) |
| 46 | Cyclo[—D—Asp—Sar—Asp—D—Leu—Leu—D—Trp—] LSIMS(M + H$^+$) = 714, (theoretical value) = 714 | (A) |
| 47 | Cyclo[—D—Asp—N—MeLeu—Asp—D—Leu—Leu—D—Trp—] LSIMS(M + H$^+$) = 770, (theoretical value) = 770 | (A) |
| 48 | Cyclo[—D—Asp—N—MePhe—Asp—D—Leu—Leu—D—Trp—] LSIMS(M + H$^+$) = 804, (theoretical value) = 804 | (A) |
| 49 | Cyclo[—D—Asp—Trp—Asp—D—Thg(3)—Leu—D—Trp—] LSIMS(M + H$^+$) = 855, (theoretical value) = 855 | (B) |

-continued

| Example No. | Compound | Process |
|---|---|---|
| 50 | Cyclo[—D—Asp—Trp—Asp—D—Thi—Leu—D—Trp—]<br>LSIMS(M + H$^+$) = 869, (theoretical value) = 869 | (B) |
| 51 | Cyclo[—D—Asp—Trp—Asp—D—aIle—Leu—D—Trp—]<br>LSIMS(M + H$^+$) = 829, (theoretical value) = 829 | (B) |
| 52 | Cyclo[—D—Asp—Trp—Asp—D—Val—Leu—D—Trp—]<br>LSIMS(M + H$^+$) = 815, (theoretical value) = 815 | (B) |
| 57 | Cyclo[—D—Asp—Ala—Asp—D—Leu—Phe—D—Trp—]<br>LSIMS(M + H$^+$) = 748, (theoretical value) = 748 | (A) |
| 58 | Cyclo[—D—Asp—Ala—Asp—D—Leu—Trp—D—Trp—]<br>LSIMS(M + H$^+$) = 787, (theoretical value) = 787 | (A) |
| 59 | Cyclo[—D—Glu—Gly—Ala—D—Leu—Leu—D—Trp—]<br>LSIMS(M + H$^+$) = 670, (theoretical value) = 670 | (A) |
| 60 | Cyclo[—D—Asp—Trp—Asp—D—Phe—Leu—D—Trp—]<br>LSIMS(M + H$^+$) = 863, (theoretical value) = 863 | (B) |
| 61 | Cyclo[—D—Asp—Trp—Asp—Achx—Leu—D—Trp—]<br>LSIMS(M + H$^+$) = 841, (theoretical value) = 841 | (B) |
| 62 | Cyclo[—D—Asp—Gln(CH$_2$Ph)—Asp—D—Leu—Leu—D—Trp—]<br>LSIMS(M + H$^+$) = 861, (theoretical value) = 861 | (C) |
| 63 | Cyclo[—D—Asp—Gln(CH$_2$CH$_2$Ph)—Asp—D—Leu—Leu—D—Trp—]<br>LSIMS(M + H$^+$) = 875, (theoretical value) = 875 | (C) |
| 64 | Cyclo[—D—Asp—Gln(CH$_2$CH$_2$—Ind)—Asp—D—Leu—Leu—D—Trp—]<br>LSIMS(M + H$^+$) = 914, (theoretical value) = 914 | (C) |
| 65 | Cyclo[—D—Asp—Arg(Tos)—Asp—D—Leu—Leu—D—Trp—]<br>LSIMS(M + H$^+$) = 953, (theoretical value) = 953 | (C) |
| 66 | Cyclo[—D—Asp—Lys(Mtr)—Asp—D—Leu—Leu—D—Trp—]<br>LSIMS(M + H$^+$) = 983, (theoretical value) = 983 | (C) |
| 67 | Cyclo[—D—Asp—N—MeTrp—Asp—D—Leu—Leu—D—Trp—]<br>LSIMS(M + H$^+$) = 843, (theoretical value) = 843 | (A) |
| 68 | Cyclo[—D—Asp—Asn(Me.CH$_2$CH$_2$Ph)—Asp—D—Leu—Leu—D—Trp—]<br>LSIMS(M + H$^+$) = 875, (theoretical value) = 875 | (C) |
| 69 | Cyclo[—D—Asp—Asn(CH$_2$CHMePh)—Asp—D—Leu—Leu—D—Trp—]<br>LSIMS(M + H$^+$) = 875, (theoretical value) = 875 | (C) |
| 70 | Cyclo[—D—Asp—Asp(R1)—Asp—D—Leu—Leu—D—Trp—]<br>LSIMS(M + H$^+$) = 902, (theoretical value) = 902 | (C) |
| 71 | Cyclo[—D—Asp—Asp(R2)—Asp—D—Leu—Leu—D—Trp—]<br>LSIMS(M + H$^+$) = 901, (theoretical value) = 901 | (C) |
| 72 | Cyclo[—D—Asp—Asp(R3)—Asp—D—Leu—Leu—D—Trp—]<br>LSIMS(M + H$^+$) = 859, (theoretical value) = 859 | (C) |
| 73 | Cyclo[—D—Asp—Asp(R4)—Asp—D—Leu—Leu—D—Trp—]<br>LSIMS(M + H$^+$) = 873, (theoretical value) = 873 | (C) |
| 74 | Cyclo[—D—Asp—Asp(R5)—Asp—D—Leu—Leu—D—Trp—]<br>LSIMS(M + H$^+$) = 887, (theoretical value) = 887 | (C) |
| 75 | Cyclo[—D—Asp—Asp(R6)—Asp—D—Leu—Leu—D—Trp—]<br>LSIMS(M + H$^+$) = 868, (theoretical value) = 868 | (C) |
| 76 | Cyclo[—D—Asp—Glu(R3)—Asp—D—Leu—Leu—D—Trp—]<br>LSIMS(M + H$^+$) = 873, (theoretical value) = 873 | (C) |
| 77 | Cyclo[—D—Asp—Glu(R4)—Asp—D—Leu—Leu—D—Trp—]<br>LSIMS(M + H$^+$) = 887, (theoretical value) = 887 | (C) |
| 78 | Cyclo[—D—Asp—Glu(R5)—Asp—D—Leu—Leu—D—Trp—]<br>LSIMS(M + H$^+$) = 901, (theoretical value) = 901 | (C) |
| 83 | Cyclo[—D—Asp—His—Asp—D—Leu—Leu—D—Trp—]<br>LSIMS(M + H$^+$) = 780, (theoretical value) = 780 | (C) |
| 84 | Cyclo[—D—Asp—His(Bom)—Asp—D—Leu—Leu—D—Trp—]<br>LSIMS(M + H$^+$) = 900, (theoretical value) = 900 | (C) |
| 85 | Cyclo[—D—Asp—His(Bzl)—Asp—D—Leu—Leu—D—Trp—]<br>LSIMS(M + H$^+$) = 870, (theoretical value) = 870 | (C) |
| 86 | Cyclo[—D—Asp—D,L-Tic—Asp—D—Leu—Leu—D—Trp—]<br>LSIMS(M + H$^+$) = 802, (theoretical value) = 802 | (C) |
| 87 | Cyclo[—D—Asp—Tpr—Asp—D—Leu—Leu—D—Trp—]<br>LSIMS(M + H$^+$) = 758, (theoretical value) = 758 | (C) |
| 91 | Cyclo[—D—Asp—Asp(Trp—NHEt)—Asp—D—Leu—Leu—D—Trp—]<br>LSIMS(M + H$^+$) = 971, (theoretical value) = 971 | (C) |
| 92 | Cyclo[—D—Asp—Asp(Trp—NHBzl)—Asp—D—Leu—Leu—D—Trp—]<br>LSIMS(M + H$^+$) = 1033, (theoretical value) = 1033 | (C) |
| 93 | Cyclo[—D—Asp—Asp(D—Trp—NHBzl)—Asp—D—Leu—Leu—D—Trp—]<br>LSIMS(M + H$^+$) = 1033, (theoretical value) = 1033 | (C) |
| 94 | Cyclo[—D—Asp—Asp(Trp—NHCH$_2$CH$_2$Ph)—Asp—D—Leu—Leu—D—Trp—]<br>LSIMS(M + H$^+$) = 1047, (theoretical value) = 1047 | (C) |
| 95 | Cyclo[—D—Asp—Trp—Asp—D—Leu—Leu—D—Trp(Me)—]<br>LSIMS(M + H$^+$) = 843, (theoretical value) = 843 | (A) |
| 96 | Cyclo[—D—Asp—Asp(R1)—Asp—D—Thg(2)—Leu—D—Trp—]<br>LSIMS(M + H$^+$) = 928, (theoretical value) = 928 | (A) |

EXAMPLES 97–203

In accordance with any one of the processes (A), (B) and (C) mentioned above, the following compounds can be synthesized:

| Example No. | Compound |
|---|---|
| 97  | Cyclo[—D—Asp—Asn(CH$_2$CH$_2$—Ind)—Asp—D—Phg—Leu—D—Trp—] |
| 98  | Cyclo[—D—Asp—Asn(CH$_2$CH$_2$—Ind)—Asp—D—Thg(3)—Leu—D—Trp—] |
| 99  | Cyclo[—D—Asp—Asn(CH$_2$CH$_2$—Ind)—Asp—Acbu—Leu—D—Trp—] |
| 100 | Cyclo[—D—Asp—Asn(CH$_2$CH$_2$—Ind)—Asp—Acpe—Leu—D—Trp—] |
| 101 | Cyclo[—D—Asp—Asn(CH$_2$CH$_2$—Ind)—Asp—Achx—Leu—D—Trp—] |
| 102 | Cyclo[—D—Asp—Asn(CH$_2$CH$_2$—Ind)—Asp—Achp—Leu—D—Trp—] |
| 103 | Cyclo[—D—Asp—Asn(CH$_2$CH$_2$—Ind)—Asp—D—Thg(2)—Leu—D—Trp(Me)—] |
| 104 | Cyclo[—D—Asp—Asn(CH$_2$CH$_2$—Ind)—Asp—D—Thg(2)—Leu—D—Trp(For)—] |
| 105 | Cyclo[—D—Cta—Trp—Asp—D—Val—Leu—D—Trp—] |
| 106 | Cyclo[—D—Cta—Trp—Asp—D—Leu—Leu—D—Trp—] |
| 107 | Cyclo[—D—Cta—Trp—Asp—D—Thg(2)—Leu—D—Trp—] |
| 108 | Cyclo[—D—Cta—Trp—Asp—D—Thg(3)—Leu—D—Trp—] |
| 109 | Cyclo[—D—Cta—Asn(CH$_2$CH$_2$—Ind)—Asp—D—Val—Leu—D—Trp—] |
| 110 | Cyclo[—D—Cta—Asn(CH$_2$CH$_2$—Ind)—Asp—D—Leu—Leu—D—Trp—] |
| 111 | Cyclo[—D—Cta—Asn(CH$_2$CH$_2$—Ind)—Asp—D—Thg(2)—Leu—D—Trp—] |
| 112 | Cyclo[—D—Cta—Asn(CH$_2$CH$_2$—Ind)—Asp—D—Thg(3)—Leu—D—Trp—] |
| 113 | Cyclo[—D—Cta—Asn(CH$_2$CH$_2$—Ind)—Asp—D—Thg(2)—Leu—D—Trp(Me)—] |
| 114 | Cyclo[—D—Cta—Asn(CH$_2$CH$_2$—Ind)—Asp—D—Thg(2)—Leu—D—Trp(For)—] |
| 115 | Cyclo[—D—Asp—Gln(CH$_2$Ph)—Asp—D—Thg(3)—Leu—D—Trp—] |
| 116 | Cyclo[—D—Asp—Gln(CH$_2$Ph)—Asp—D—Phg—Leu—D—Trp—] |
| 117 | Cyclo[—D—Asp—Gln(CH$_2$Ph)—Asp—D—Leu—Leu—D—Trp—] |
| 118 | Cyclo[—D—Asp—Gln(CH$_2$Ph)—Asp—D—Val—Leu—D—Trp—] |
| 119 | Cyclo[—D—Asp—Gln(CH$_2$Ph)—Asp—D—aIle—Leu—D—Trp—] |
| 120 | Cyclo[—D—Asp—Gln(CH$_2$Ph)—Asp—D—tLeu—Leu—D—Trp—] |
| 121 | Cyclo[—D—Asp—Gln(CH$_2$Ph)—Asp—D—Thg(2)—Leu—D—Trp(Me)—] |
| 122 | Cyclo[—D—Asp—Gln(CH$_2$Ph)—Asp—D—Thg(3)—Leu—D—Trp(Me)—] |
| 123 | Cyclo[—D—Asp—Gln(CH$_2$Ph)—Asp—D—Thg(2)—Leu—D—Trp(For)—] |
| 124 | Cyclo[—D—Asp—Gln(CH$_2$Ph)—Asp—D—Thg(3)—Leu—D—Trp(For)—] |
| 125 | Cyclo[—D—Asp—Gln(CH$_2$CH$_2$Ph)—Asp—D—Thg(2)—Leu—D—Trp—] |
| 126 | Cyclo[—D—Asp—Gln(CH$_2$CH$_2$Ph)—Asp—D—Thg(3)—Leu—D—Trp—] |
| 127 | Cyclo[—D—Asp—Gln(CH$_2$CH$_2$—Ind)—Asp—D—Thg(2)—Leu—D—Trp—] |
| 128 | Cyclo[—D—Asp—Gln(CH$_2$CH$_2$—Ind)—Asp—D—Thg(3)—Leu—D—Trp—] |
| 129 | Cyclo[—D—Cta—Gln(CH$_2$Ph)—Asp—D—Thg(2)—Leu—D—Trp—] |
| 130 | Cyclo[—D—Cta—Gln(CH$_2$Ph)—Asp—D—Thg(3)—Leu—D—Trp—] |
| 131 | Cyclo[—D—Cta—Gln(CH$_2$CH$_2$Ph)—Asp—D—Thg(2)—Leu—D—Trp—] |
| 132 | Cyclo[—D—Cta—Gln(CH$_2$CH$_2$Ph)—Asp—D—Thg(3)—Leu—D—Trp—] |
| 133 | Cyclo[—D—Cta—Gln(CH$_2$CH$_2$—Ind)—Asp—D—Thg(2)—Leu—D—Trp—] |
| 134 | Cyclo[—D—Cta—Gln(CH$_2$CH$_2$—Ind)—Asp—D—Thg(3)—Leu—D—Trp—] |
| 135 | Cyclo[—D—Asp—Asn(CH$_2$CH$_2$—Ind)—Asp—D—Val—Leu—D—Trp—] |
| 136 | Cyclo[—D—Asp—Asp(R7)—Asp—D—Thg(2)—Leu—D—Trp—] |
| 137 | Cyclo[—D—Asp—Asp(R8)—Asp—D—Thg(2)—Leu—D—Trp—] |
| 138 | Cyclo[—D—Asp—Asp(R9)—Asp—D—Thg(2)—Leu—D—Trp—] |
| 139 | Cyclo[—D—Asp—Asp(R10)—Asp—D—Thg(2)—Leu—D—Trp—] |
| 140 | Cyclo[—D—Asp—Asp(R11)—Asp—D—Thg(2)—Leu—D—Trp—] |
| 141 | Cyclo[—D—Asp—Asp(R12)—Asp—D—Thg(2)—Leu—D—Trp—] |
| 142 | Cyclo[—D—Asp—Asp(R13)—Asp—D—Thg(2)—Leu—D—Trp—] |
| 143 | Cyclo[—D—Asp—Asp(R14)—Asp—D—Thg(2)—Leu—D—Trp—] |
| 144 | Cyclo[—D—Asp—Asp(R15)—Asp—D—Thg(2)—Leu—D—Trp—] |
| 145 | Cyclo[—D—Asp—Asp(R16)—Asp—D—Thg(2)—Leu—D—Trp—] |
| 146 | Cyclo[—D—Cta—Asp(R1)—Asp—D—Thg(2)—Leu—D—Trp—] |
| 147 | Cyclo[—D—Cta—Asp(R7)—Asp—D—Thg(2)—Leu—D—Trp—] |
| 148 | Cyclo[—D—Cta—Asp(R8)—Asp—D—Thg(2)—Leu—D—Trp—] |
| 149 | Cyclo[—D—Cta—Asp(R9)—Asp—D—Thg(2)—Leu—D—Trp—] |
| 150 | Cyclo[—D—Cta—Asp(R10)—Asp—D—Thg(2)—Leu—D—Trp—] |
| 151 | Cyclo[—D—Cta—Asp(R11)—Asp—D—Thg(2)—Leu—D—Trp—] |
| 152 | Cyclo[—D—Cta—Asp(R12)—Asp—D—Thg(2)—Leu—D—Trp—] |
| 153 | Cyclo[—D—Cta—Asp(R13)—Asp—D—Thg(2)—Leu—D—Trp—] |
| 154 | Cyclo[—D—Cta—Asp(R14)—Asp—D—Thg(2)—Leu—D—Trp—] |
| 155 | Cyclo[—D—Cta—Asp(R15)—Asp—D—Thg(2)—Leu—D—Trp—] |
| 156 | Cyclo[—D—Cta—Asp(R16)—Asp—D—Thg(2)—Leu—D—Trp—] |
| 157 | Cyclo[—D—Asp—Asp(R1)—Asp—D—Cpg—Leu—D—Trp—] |
| 158 | Cyclo[—D—Asp—Asp(R7)—Asp—D—Cpg—Leu—D—Trp—] |
| 159 | Cyclo[—D—Asp—Asp(R8)—Asp—D—Cpg—Leu—D—Trp—] |
| 160 | Cyclo[—D—Asp—Asp(R9)—Asp—D—Cpg—Leu—D—Trp—] |
| 161 | Cyclo[—D—Asp—Asp(R10)—Asp—D—Cpg—Leu—D—Trp—] |
| 162 | Cyclo[—D—Asp—Asp(R11)—Asp—D—Cpg—Leu—D—Trp—] |
| 163 | Cyclo[—D—Asp—Asp(R12)—Asp—D—Cpg—Leu—D—Trp—] |
| 164 | Cyclo[—D—Asp—Asp(R13)—Asp—D—Cpg—Leu—D—Trp—] |
| 165 | Cyclo[—D—Asp—Asp(R14)—Asp—D—Cpg—Leu—D—Trp—] |
| 166 | Cyclo[—D—Asp—Asp(R15)—Asp—D—Cpg—Leu—D—Trp—] |
| 167 | Cyclo[—D—Asp—Asp(R16)—Asp—D—Cpg—Leu—D—Trp—] |

-continued

| Example No. | Compound |
|---|---|
| 168 | Cyclo[—D—Cta—Asp(R1)—Asp—D—Cpg—Leu—D—Trp—] |
| 169 | Cyclo[—D—Cta—Asp(R7)—Asp—D—Cpg—Leu—D—Trp—] |
| 170 | Cyclo[—D—Cta—Asp(R8)—Asp—D—Cpg—Leu—D—Trp—] |
| 171 | Cyclo[—D—Cta—Asp(R9)—Asp—D—Cpg—Leu—D—Trp—] |
| 172 | Cyclo[—D—Cta—Asp(R10)—Asp—D—Cpg—Leu—D—Trp—] |
| 173 | Cyclo[—D—Cta—Asp(R11)—Asp—D—Cpg—Leu—D—Trp—] |
| 174 | Cyclo[—D—Cta—Asp(R12)—Asp—D—Cpg—Leu—D—Trp—] |
| 175 | Cyclo[—D—Cta—Asp(R13)—Asp—D—Cpg—Leu—D—Trp—] |
| 176 | Cyclo[—D—Cta—Asp(R14)—Asp—D—Cpg—Leu—D—Trp—] |
| 177 | Cyclo[—D—Cta—Asp(R15)—Asp—D—Cpg—Leu—D—Trp—] |
| 178 | Cyclo[—D—Cta—Asp(R16)—Asp—D—Cpg—Leu—D—Trp—] |
| 179 | Cyclo[—D—Asp—Asp(R7)—Asp—D—Leu—Leu—D—Trp—] |
| 180 | Cyclo[—D—Asp—Asp(R8)—Asp—D—Leu—Leu—D—Trp—] |
| 181 | Cyclo[—D—Asp—Asp(R9)—Asp—D—Leu—Leu—D—Trp—] |
| 182 | Cyclo[—D—Asp—Asp(R10)—Asp—D—Leu—Leu—D—Trp—] |
| 183 | Cyclo[—D—Asp—Asp(R11)—Asp—D—Leu—Leu—D—Trp—] |
| 184 | Cyclo[—D—Asp—Asp(R12)—Asp—D—Leu—Leu—D—Trp—] |
| 185 | Cyclo[—D—Asp—Asp(R13)—Asp—D—Leu—Leu—D—Trp—] |
| 186 | Cyclo[—D—Asp—Asp(R14)—Asp—D—Leu—Leu—D—Trp—] |
| 187 | Cyclo[—D—Asp—Asp(R15)—Asp—D—Leu—Leu—D—Trp—] |
| 188 | Cyclo[—D—Asp—Asp(R16)—Asp—D—Leu—Leu—D—Trp—] |
| 189 | Cyclo[—D—Cta—Asp(R1)—Asp—D—Leu—Leu—D—Trp—] |
| 190 | Cyclo[—D—Cta—Asp(R7)—Asp—D—Leu—Leu—D—Trp—] |
| 191 | Cyclo[—D—Cta—Asp(R8)—Asp—D—Leu—Leu—D—Trp—] |
| 192 | Cyclo[—D—Cta—Asp(R9)—Asp—D—Leu—Leu—D—Trp—] |
| 193 | Cyclo[—D—Cta—Asp(R10)—Asp—D—Leu—Leu—D—Trp—] |
| 194 | Cyclo[—D—Cta—Asp(R11)—Asp—D—Leu—Leu—D—Trp—] |
| 195 | Cyclo[—D—Cta—Asp(R12)—Asp—D—Leu—Leu—D—Trp—] |
| 196 | Cyclo[—D—Cta—Asp(R13)—Asp—D—Leu—Leu—D—Trp—] |
| 197 | Cyclo[—D—Cta—Asp(R14)—Asp—D—Leu—Leu—D—Trp—] |
| 198 | Cyclo[—D—Cta—Asp(R15)—Asp—D—Leu—Leu—D—Trp—] |
| 199 | Cyclo[—D—Cta—Asp(R16)—Asp—D—Leu—Leu—D—Trp—] |
| 200 | Cyclo[—D—Asp—Asp(R1)—Asp—D—Thi—Leu—D—Trp—] |
| 201 | Cyclo[—D—Asp—Asp(R1)—Asp—D—Phe—Leu—D—Trp—] |
| 202 | Cyclo[—D—Cta—Asp(R1)—Asp—D—Thi—Leu—D—Trp—] |
| 203 | Cyclo[—D—Cta—Asp(R1)—Asp—D—Phe—Leu—D—Trp—] |

In the formulae, R1 to R16 represent the following groups:

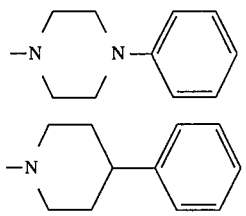 $R_1$

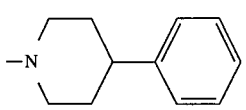 $R_2$

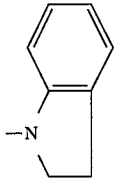 $R_3$

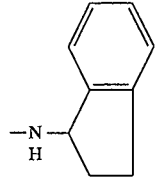 $R_4$

-continued

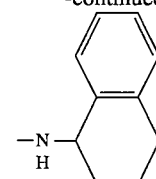 $R_5$

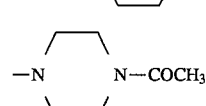 $R_6$

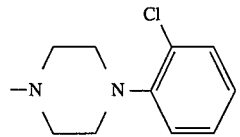 $R_7$

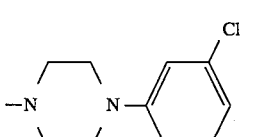 $R_8$

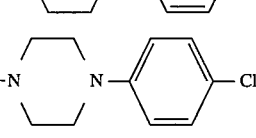 $R_9$

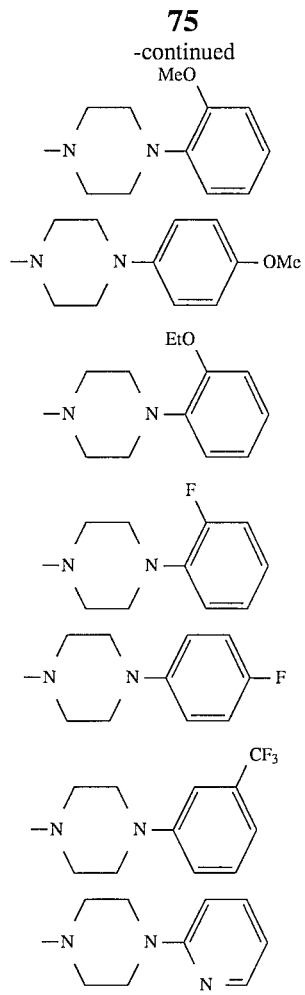

Experimental Example 1

Assay of Affinity for Receptor (1) . . . Binding Activity on $ET_A$ Receptor

A membrane fraction prepared from the porcine heart was diluted to 0.15 mg/ml by using a buffer solution for assay, and 100 μl of the resulting suspension of the membrane fraction was poured into each assay tube to use for assay. To this suspension of the membrane fraction was added 2 μl of 5 nM $^{125}$I-labeled endothelin-1 solution. Further, 3 μl of a test peptide solution was added thereto, followed by incubation at a temperature of 25° C. for 1 hour. Then, the resulting suspension was diluted with 900 μl of the buffer solution for assay cooled with ice, and thereafter separated into a supernatant and a precipitate by centrifugation at 12,000×g for 10 minutes. Cell membranes and an endothelin receptor A ($ET_A$) embedded therein were contained in the precipitate, and radioactive iodine-labeled endothelin combined with the receptor was also recovered in the precipitate. Accordingly, the amount of radioactive iodine-labeled endothelin combined with the endothelin receptor A ($ET_A$) was determined by measuring the amount of radioactive iodine contained in the precipitate with a gamma-ray counter. Results are as shown in Table 1 given below. The cyclic pentapeptide described in Japanese Patent Application No. 2-413828/1990, cyclo[-D-Glu-Ala-D-alle-Leu-D-Trp-], was used as a control compound. The numerical value of $ET_A$ shown in Table 1 is the value of specific activity, taking the binding activity of this cyclic pentapeptide on the receptor A as 1.0. The binding activity ($IC_{50}$) of this cyclic pentapeptide on the $ET_A$ receptor is $2\times10^{-6}$M.

Experimental Example 2

Assay of Affinity for Receptor (2) . . . Binding Activity on $ET_B$ Receptor *1

A membrane fraction prepared from the bovine brain was diluted to 0.15 mg/ml by using a buffer solution for assay, and 100 μl of the resulting suspension of the membrane fraction was poured into each assay tube to use for assay. To this suspension of the membrane fraction was added 2 μl of 5 nM $^{125}$I labeled endothelin-1 solution. Further, 3 μl of a test peptide solution was added thereto, followed by incubation at a temperature of 25° C. for 1 hour. Then, the resulting suspension was diluted with 900 μl of the buffer solution for assay cooled with ice, and thereafter separated into a supernatant and a precipitate by centrifugation at 12,000×g for 10 minutes. Cell membranes and an endothelin receptor B ($ET_B$) embedded therein were contained in the precipitate, and radioactive iodine-labeled endothelin bound to the receptor was also recovered in the precipitate. Accordingly, the amount of radioactive iodine-labeled endothelin bound to the endothelin receptor B ($ET_B$) was determined by measuring the amount of radioactive iodine contained in the precipitate with a gamma-ray counter. Results are as shown in Table 1 given below. The numerical value of $ET_B$ shown in Table 1 is the value of specific activity, taking the binding activity of the compound of Example 8 on the receptor B as 100. The binding activity ($IC_{50}$) of the compound of Example 8 on the $ET_B$ receptor is $3\times10^{-6}$M. According to the same assay, the value of specific activity of the pentapeptide described in European Patent Publication No. 436,189, cyclo[-D-Asp-Pro-D-val-Leu-D-Trp-], was less than 5, and that of the above-mentioned cyclic pentapeptide described in Japanese Patent Application No. 2-413328/1990, cyclo[-D-Glu-Ala-D-alle-Leu-D-Trp-], was less than 1.

Experimental Example 2'

$ET_B$ Radio Receptor Assay *2

In the endothelin radio receptor assay, guinea pigs' kidneys were used. Guinea pigs (Std Hartrey, male 250 g, Japan SLC Ltd.) were made to have a cerebral concussion and sacrificed by bleeding from carotid arteries to pick up the kidneys and removed fat therefrom to prepare the kidneys. The obtained kidneys were sliced and homogenized by politron homogenizer in 20 ml of 50 mM Tris-HCl buffer [pH 7.4; 20 mM NaHCO$_3$, 0.1 mM PMSF (Phenylmethylsulfonyl Fluoride), 1 mM EDTA (Ethylenediaminetetraacetic acid)] per one kidney. The homogenized kidney was applied to a centrifugation at 1,000×g for 15 minutes and the supernatant was further applied to a centrifugation for 20 minutes at 30,000×g. The resulting precipitate was twice washed with 50 mM Tris-HCl buffer (pH 7.4) containing 0.1 mM PMSF, 1 mM EDTA. The resultant was stored at −80 ° C. as a crude receptor membrane fraction and was used as the suspension in the following buffer when necessary.

740 Bq of $^{125}$I-endothelin-1 (81.4 TBq/mmol, Du Pont, USA) as a radio ligand, the crude membrane fraction (2.1 μg protein) and samples were added to the following buffer. The reaction was performed at 37° C., for 90 minutes in 0.2 ml of the buffer [50 mM Tris-HCl buffer (pH 7.4) containing 0.1 mM PMSF, 1 mM EDTA, 0.2% bovine serum albumin].

The reaction was stopped by fast filtration on a glass filter (GF/B, Wattman, USA) by Cell Harvestor (290 PHD, Cambridge-Technology, Great Britain), and the filter was three times washed with 50 mM Tris-HCl buffer (pH 7.4). Radio activity remained on the filter was assayed by a gamma counter.

The results are shown in Table 1.

Experimental Example 3

Assay of Affinity for Receptor (3) . . . Binding Inhibiting Activity on NK2 Receptor The method of Paul L. M. Van Giersbergen et al. [*Proc. Natl. Acad. Sci. U.S.A.*, 88, 1661 (1991) was modified for this assay. The membrane fraction containing the receptor was prepared from the inner wall of the bovine third stomach (purchased from Kyoto Chuo Chikusan Fukuseibutsu Oroshi Kyoukai).

The inner wall of the bovine third stomach stored at −80° C. was cut to 1 cm×1 cm or less, and disrupted in 3 liters/kg of 50 mM Tris-HCl buffer (pH 7.4) supplemented with 120 mM sodium chloride, 5 mM potassium chloride, 0.02% BSA and 5% sucrose, using a polytron homogenizer (Kinematika, Germany). Then, the disrupted product was centrifuged at 1,000×g for 10 minutes. The supernatant was further centrifuged at 45,000×g for 20 minutes. The precipitate was suspended in 200 ml of 50 mM Tris-HCl buffer (pH 7.4) supplemented with 300 mM potassium chloride, 10 mM ethylenediaminetetraacetic acid, 0.1 mM phenylmethylsulfonium fluoride and 0.02% BSA, and gently stirred under ice cooling for 60 minutes. The suspension was centrifuged at 45,000×g for 20 minutes. The precipitate was washed with 200 ml of 50 mM Tris-HCl buffer (pH 7.4), and stored in the frozen state at −40° C. as a receptor sample.

This sample was suspended in a reaction buffer solution [50 mM Tris-HCl buffer (pH 7.4), 0.02% bovine serum albumin and 4 mM manganese chloride] so as to give a protein concentration of 0.7 mg/ml, and 100 μl thereof was used for reaction. A test sample and $^{125}$I-NKA (0.61 KBq, $^{125}$I-neurokinin A, 81.4 TBq/mmol, Du Pont/NEN Research Products, U.S.A.) were also added, and reacted in 0.2 ml of the reaction buffer solution at 25° C. for 3 hours. The reaction mixture was rapidly filtered through a glass filter (GF/B, Whatman, U.S.A.) using a cell harvester (Type 290PHD, Cambridge Technology Inc.) to terminate the reaction, and washed 3 times with 250 μl of 50 mM Tris-HCl buffer (pH 7.4) supplemented with 0.02% bovine serum albumin. The radioactivity left on the filter was measured with a gamma-ray counter. Results are shown in Table 1 as the binding inhibiting activity ($IC_{50}$, unit: μM) on the NK2 receptor.

TABLE 1

| Example No. | Compound | Binding Activity on ET Receptor (R. act.) | | | Binding Inhibiting Activity on NK2 Receptor ($IC_{50}$, μM) |
|---|---|---|---|---|---|
| | | $ET_A$ | $ET_B$*1 | $ET_B$*2 | |
| 1 | Cyclo[—D—Asp—Ala—Asp—D—Leu—Leu—D—Trp—] | 9.7 | 13 | 2.0 | |
| 2 | Cyclo[—D—Asp—Ala—D—Asp—D—Leu—Leu—D—Trp—] | 3.7 | | 3.1 | |
| 3 | Cyclo[—D—Asp—Ala—Glu—D—Leu—Leu—D—Trp—] | 7.9 | | 23 | |
| 4 | Cyclo[—D—Asp—Ala—D—Glu—D—Leu—Leu—D—Trp—] | 2.3 | | 1.4 | |
| 5 | Cyclo[—D—Asp—Gly—Ala—D—Leu—Leu—D—Trp—] | 1.3 | | — | |
| 6 | Cyclo[—D—Asp—Asp—Ala—D—Leu—Leu—D—Trp—] | 6.0 | | 7.1 | |
| 7 | Cyclo[—D—Asp—Glu—Ala—D—Leu—Leu—D—Trp—] | 6.5 | | 7.1 | |
| 8 | Cyclo[—D—Asp—Trp—Asp—D—Leu—Leu—D—Trp—] | 76 | 100 | 100 | 6.4 |
| 9 | Cyclo[—D—Asp—Pro—Asp—D—Leu—Leu—D—Trp—] | 56 | 140 | 67 | |
| 10 | Cyclo[—D—Asp—Asn($CH_2$Ph)—Asp—D—Leu—Leu—D—Trp—] | 43 | 26 | 24 | |
| 11 | Cyclo[—D—Asp—Asn($CH_2CH_2$Ph)—Asp—D—Leu—Leu—D—Trp—] | 93 | 42 | 44 | |
| 12 | Cyclo[—D—Asp—Asn($CH_2CH_2$—Ind)—Asp—D—Leu—Leu—D—Trp—] | 220 | 230 | 150 | |
| 13 | Cyclo[—D—Asp—Hyp(Bzl)—Asp—D—Leu—Leu—D—Trp—] | 83 | 85 | 140 | |
| 14 | Cyclo[—D—Asp—Hyp—Asp—D—Leu—Leu—D—Trp—] | 70 | 160 | 120 | |
| 15 | Cyclo[—D—Asp—D—Ala—Asp—D—Leu—Leu—D—Trp—] | 5.7 | | 7.7 | |
| 16 | Cyclo[—D—Asp—Asp—Asp—D—Leu—Leu—D—Trp—] | 10 | 14 | 34 | |
| 17 | Cyclo[—D—Asp—Val—Asp—D—Leu—Leu—D—Trp—] | 3.7 | | 22 | |
| 18 | Cyclo[—D—Asp—Leu—Asp—D—Leu—Leu—D—Trp—] | 13 | | 2.2 | |
| 19 | Cyclo[—D—Asp—Phe—Asp—D—Leu—Leu—D—Trp—] | 8.3 | | 7.1 | |
| 20 | Cyclo[—D—Asp—Ser(Bzl)—Asp—D—Leu—Leu—D—Trp—] | 14 | | 13 | |
| 21 | Cyclo[—D—Asp—Thr(Bzl)—Asp—D—Leu—Leu—D—Trp—] | 4.3 | | 5.0 | |
| 22 | Cyclo[—D—Asp—Trp(For)—Asp—D—Leu—Leu—D—Trp—] | 8.3 | 6.7 | 15 | |
| 23 | Cyclo[—D—Asp—Nal(1)—Asp—D—Leu—Leu—D—Trp—] | 8.3 | 11 | 7.7 | 2.1 |
| 24 | Cyclo[—D—Asp—D—Pro—Asp—D—Leu—Leu—D—Trp—] | 1.7 | | — | |
| 25 | Cyclo[—D—Asp—Azc—Asp—D—Leu—Leu—D—Trp—] | 30 | 25 | 57 | |
| 26 | Cyclo[—D—Asp—Pip—Asp—D—Leu—Leu—D—Trp—] | 25 | 38 | 73 | |
| 27 | Cyclo[—D—Asp—D—Asp—Ala—D—Leu—Leu—D—Trp—] | 5.7 | | 4.8 | |
| 28 | Cyclo[—D—Asp—D—Glu—Ala—D—Leu—Leu—D—Trp—] | 5.7 | | 5.3 | |
| 29 | Cyclo[—D—Asp—Asp—D—Ala—D—Leu—Leu—D—Trp—] | 2.6 | | 2.4 | |
| 30 | Cyclo[—D—Asp—Asp—Pro—D—Leu—Leu—D—Trp—] | 4.4 | | 9.1 | |
| 31 | Cyclo[—D—Asp—Asp—D—Pro—D—Leu—Leu—D—Trp—] | 2.6 | | 1.0 | |
| 32 | Cyclo[—D—Asp—Asp—Leu—D—Leu—Leu—D—Trp—] | 4.0 | | 7.7 | 2.6 |
| 33 | Cyclo[—D—Asp—Asp—Trp—D—Leu—Leu—D—Trp—] | 2.9 | | 5.6 | 0.35 |
| 34 | Cyclo[—D—Asp—Trp—Glu—D—Leu—Leu—D—Trp—] | 20 | 77 | 44 | 7.4 |
| 35 | Cyclo[—D—Asp—Trp—Leu—D—Leu—Leu—D—Trp—] | 9.1 | 52 | 24 | 0.052 |
| 36 | Cyclo[—D—Asp—Trp—Pro—D—Leu—Leu—D—Trp—] | 17 | 40 | 42 | 1.1 |
| 37 | Cyclo[—D—Asp—Trp—Ser—D—Leu—Leu—D—Trp—] | 24 | 22 | 18 | 0.28 |
| 38 | Cyclo[—D—Asp—Trp—Ser(Bzl)—D—Leu—Leu—D—Trp—] | 13 | 66 | 170 | 0.070 |
| 39 | Cyclo[—D—Asp—Ala—Asp—D—tLeu—Leu—D—Trp—] | 6.8 | 59 | 53 | |
| 40 | Cyclo[—D—Glu—Ala—Gly—D—Leu—Leu—D—Trp—] | 1.4 | | | |
| 41 | Cyclo[—D—Glu—Ala—Asp—D—Leu—Leu—D—Trp—] | 2.1 | | 26 | |
| 42 | Cyclo[—D—Asp—Trp—Asp—D—Leu—Leu—D—Trp(For)—] | 150 | 100 | 150 | |
| 43 | Cyclo[—D—Asp—Trp—Asp—D—Leu—Leu—D—Trp(Ac)—] | 8.2 | 120 | 250 | |
| 44 | Cyclo[—D—Asp—Trp—Asp—Acpe—Leu—D—Trp—] | 34 | | 11 | |
| 45 | Cyclo[—D—Asp—Trp—Asp—D—Phg—Leu—D—Trp—] | 87 | 74 | 180 | |
| 46 | Cyclo[—D—Asp—Sar—Asp—D—Leu—Leu—D—Trp—] | 8.1 | | 75 | |

TABLE 1-continued

| Example No. | Compound | Binding Activity on ET Receptor (R. act.) | | | Binding Inhibiting Activity on NK2 Receptor (IC$_{50}$, μM) |
|---|---|---|---|---|---|
| | | ET$_A$ | ET$_B$*1 | ET$_B$*2 | |
| 47 | Cyclo[—D—Asp—N-MeLeu—Asp—D—Leu—Leu—D—Trp—] | 6.8 | | 17 | |
| 48 | Cyclo[—D—Asp—N-MePhe—Asp—D—Leu—Leu—D—Trp—] | 2.7 | | 13 | |
| 49 | Cyclo[—D—Asp—Trp—Asp—D—Thg(3)—Leu—D—Trp—] | 270 | 74 | 75 | |
| 50 | Cyclo[—D—Asp—Trp—Asp—D—Thi—Leu—D—Trp—] | 4 | 350 | 57 | |
| 51 | Cyclo[—D—Asp—Trp—Asp—D—aIle—Leu—D—Trp—] | 100 | 210 | 290 | |
| 52 | Cyclo[—D—Asp—Trp—Asp—D—Val—Leu—D—Trp—] | 75 | 240 | 100 | |
| 53 | Cyclo[—D—Asp—Trp—Asp—D—tLeu—Leu—D—Trp—] | 64 | | 460 | |
| 54 | Cyclo[—D—Asp—Trp—Asp—D—γMeLeu—Leu—D—Trp—] | 99 | | 1000 | |
| 55 | Cyclo[—D—Asp—Trp—Asp—D—Thg(2)—Leu—D—Trp—] | 340 | | 120 | |
| 56 | Cyclo[—D—Asp—Trp—Asp—Acbu—Leu—D—Trp—] | 51 | | 4.3 | |
| 57 | Cyclo[—D—Asp—Ala—Asp—D—Leu—Phe—D—Trp—] | | | 2.0 | |
| 58 | Cyclo[—D—Asp—Ala—Asp—D—Leu—Trp—D—Trp—] | 0.7 | 6.7 | 22 | |
| 59 | Cyclo[—D—Glu—Gly—Ala—D—Leu—Leu—D—Trp—] | | | | |
| 60 | Cyclo[—D—Asp—Trp—Asp—D—Phe—Leu—D—Trp—] | 1 | 210 | 44 | |
| 61 | Cyclo[—D—Asp—Trp—Asp—Achx—Leu—D—Trp—] | 39 | | 52 | |
| 62 | Cyclo[—D—Asp—Gln(CH$_2$Ph)—Asp—D—Leu—Leu—D—Trp—] | 170 | | 120 | |
| 63 | Cyclo[—D—Asp—Gln(CH$_2$CH$_2$Ph)—Asp—D—Leu—Leu—D—Trp—] | 130 | | 340 | |
| 64 | Cyclo[—D—Asp—Gln(CH$_2$CH$_2$—Ind)—Asp—D—Leu—Leu—D—Trp—] | 120 | | 270 | |
| 65 | Cyclo[—D—Asp—Arg(Tos)—Asp—D—Leu—Leu—D—Trp—] | 20 | | 63 | |
| 66 | Cyclo[—D—Asp—Lys(Mtr)—Asp—D—Leu—Leu—D—Trp—] | 51 | | 120 | |
| 67 | Cyclo[—D—Asp—N-MeTrp—Asp—D—Leu—Leu—D—Trp—] | 9.1 | | 30 | |
| 68 | Cyclo[—D—Asp—Asn(Me.CH$_2$CH$_2$Ph)—Asp—D—Leu—Leu—D—Trp—] | 24 | | 52 | |
| 69 | Cyclo[—D—Asp—Asn(CH$_2$CHMePh)—Asp—D—Leu—Leu—D—Trp—] | 140 | | 60 | |
| 70 | Cyclo[—D—Asp—Asp(R1)—Asp—D—Leu—Leu—D—Trp—] | 360 | 1500 | 2600 | |
| 71 | Cyclo[—D—Asp—Asp(R2)—Asp—D—Leu—Leu—D—Trp—] | 160 | | 1000 | |
| 72 | Cyclo[—D—Asp—Asp(R3)—Asp—D—Leu—Leu—D—Trp—] | 45 | | 100 | |
| 73 | Cyclo[—D—Asp—Asp(R4)—Asp—D—Leu—Leu—D—Trp—] | 80 | | 40 | |
| 74 | Cyclo[—D—Asp—Asp(R5)—Asp—D—Leu—Leu—D—Trp—] | 37 | | 31 | |
| 75 | Cyclo[—D—Asp—Asp(R6)—Asp—D—Leu—Leu—D—Trp—] | 9 | | 33 | |
| 76 | Cyclo[—D—Asp—Glu(R3)—Asp—D—Leu—Leu—D—Trp—] | 17 | | 57 | 10 |
| 77 | Cyclo[—D—Asp—Glu(R4)—Asp—D—Leu—Leu—D—Trp—] | 66 | | 100 | |
| 78 | Cyclo[—D—Asp—Glu(R5)—Asp—D—Leu—Leu—D—Trp—] | 120 | | 130 | |
| 79 | Cyclo[—D—Asp—Orn(COPh)—Asp—D—Leu—Leu—D—Trp—] | 26 | | 71 | |
| 80 | Cyclo[—D—Asp—Orn(COCH$_2$Ph)—Asp—D—Leu—Leu—D—Trp—] | 260 | | 380 | |
| 81 | Cyclo[—D—Asp—Orn(COCH$_2$CH$_2$Ph)—Asp—D—Leu—Leu—D—Trp—] | 68 | | 160 | |
| 82 | Cyclo[—D—Asp—Orn(COCH$_2$—Ind)—Asp—D—Leu—Leu—D—Trp—] | 240 | | 500 | |
| 83 | Cyclo[—D—Asp—His—Asp—D—Leu—Trp—D—Trp—] | 15 | | 43 | |
| 84 | Cyclo[—D—Asp—His(Bom)—Asp—D—Leu—Leu—D—Trp—] | 20 | | 80 | |
| 85 | Cyclo[—D—Asp—His(Bzl)—Asp—D—Leu—Leu—D—Trp—] | 19 | | 43 | |
| 86 | Cyclo[—D—Asp—D,L-Tic—Asp—D—Leu—Leu—D—Trp—] | 38 | | 240 | |
| 87 | Cyclo[—D—Asp—Tpr—Asp—D—Leu—Leu—D—Trp—] | 93 | | 380 | |
| 88 | Cyclo[—D—Asp—Hyp(Bzl)—Asp—D—Thg(2)—Leu—D—Trp—] | 650 | 200 | 210 | |
| 89 | Cyclo[—D—Asp—Glu(Bzl)—Asp—D—Thg(2)—Leu—D—Trp—] | 750 | 45 | 71 | |
| 90 | Cyclo[—D—Asp—Asn(CH$_2$CH$_2$Ind)—Asp—D—Thg(2)—Leu—D—Trp—] | 810 | 590 | 280 | |
| 91 | Cyclo[—D—Asp—Asp(Trp—NHET)—Asp—D—Leu—Leu—D—Trp—] | 130 | | 200 | |
| 92 | Cyclo[—D—Asp—Asp(Trp—NHBzl)—Asp—D—Leu—Leu—D—Trp—] | 95 | | 260 | 4.0 |
| 93 | Cyclo[—D—Asp—Asp(D—Trp—NHBzl)—Asp—D—Leu—Leu—D—Trp—] | 110 | | 270 | |
| 94 | Cyclo[—D—Asp—Asp(Trp—NHCH$_2$CH$_2$Ph)—Asp—D—Leu—Leu—D—Trp—] | 120 | | 140 | 5.8 |
| 95 | Cyclo[—D—Asp—Trp—Asp—D—Leu—Leu—D—Trp(Me)—] | 110 | | 330 | |
| 96 | Cyclo[—D—Asp—Asp(R1)—Asp—D—Thg(2)—Leu—D—Trp—] | 980 | 1800 | | |

What is claimed is:

1. A cyclic peptide having endothelin receptor antagonistic activity represented by formula [I] or a pharmaceutically acceptable salt thereof:

$$\boxed{\text{A}-\text{X}-\text{Y}-\text{B}-\text{C}-\text{D}} \quad [\text{I}]$$

wherein A is D-aspartic acid, X is aspartic acid β-4-phenylpiperazineamide, Y is aspartic acid, B is D-2-thienylglycine, C is leucine and D is D-tryptophan.

* * * * *